US008486464B2

(12) United States Patent
Yan et al.

(10) Patent No.: US 8,486,464 B2
(45) Date of Patent: *Jul. 16, 2013

(54) HERBAL COMPOSITION FOR ANGINA PECTORIS, METHOD TO PREPARE SAME AND USES THEREOF

(75) Inventors: Xijun Yan, Tianjin (CN); Naifeng Wu, Tianjin (CN); Zhixin Guo, Tianjin (CN); Zhengliang Ye, Tianjin (CN); Yan Liu, Tianjin (CN)

(73) Assignee: Tasly Pharmaceutical Group Co. Ltd., Tianjin (CN)

( * ) Notice: Subject to any disclaimer, the term of this patent is extended or adjusted under 35 U.S.C. 154(b) by 0 days.

This patent is subject to a terminal disclaimer.

(21) Appl. No.: 10/210,548

(22) Filed: Jul. 31, 2002

(65) Prior Publication Data

US 2003/0152651 A1 Aug. 14, 2003

Related U.S. Application Data

(63) Continuation-in-part of application No. PCT/US01/49396, filed on Dec. 18, 2001.

(60) Provisional application No. 60/258,057, filed on Dec. 22, 2000.

(30) Foreign Application Priority Data

Nov. 9, 2001 (CN) .................................. 01 1 36155
Dec. 21, 2001 (TW) .............................. 90132075 A

(51) Int. Cl.
*A61K 36/537* (2006.01)
*A61K 36/258* (2006.01)
*A01N 25/34* (2006.01)
*C07C 35/00* (2006.01)

(52) U.S. Cl.
USPC ........... 424/746; 424/728; 424/408; 424/773; 568/820

(58) Field of Classification Search
USPC .......... 424/734, 728, 745, 773, 443; 514/866, 514/894, 783; 510/104
See application file for complete search history.

(56) References Cited

U.S. PATENT DOCUMENTS

| | | | |
|---|---|---|---|
| 4,755,504 A * | 7/1988 | Liu | |
| 4,999,343 A * | 3/1991 | Liu | |
| 5,288,485 A | 2/1994 | Kikuta et al. | |
| 5,401,502 A | 3/1995 | Wunderlich et al. | |
| 5,433,957 A | 7/1995 | Kikuta et al. | |
| 5,589,182 A | 12/1996 | Tashiro et al. | |
| 5,776,463 A | 7/1998 | Arginteanu | |
| 7,396,545 B2 * | 7/2008 | Cheng et al. | |
| 2005/0037094 A1 | 2/2005 | Yan et al. | |

FOREIGN PATENT DOCUMENTS

| | | | |
|---|---|---|---|
| CN | 1100657 | | 3/1995 |
| CN | 1101556 A | * | 4/1995 |
| CN | 1185963 A | * | 7/1998 |
| CN | 1041494 C | * | 1/1999 |
| CN | 1249943 A | | 8/1999 |
| CN | 1055630 C | * | 8/2000 |
| CN | 1325725 A | | 5/2001 |
| CN | 1348815 A | | 5/2002 |
| DE | 1467767 A | * | 12/1968 |
| JP | 06211713 A | * | 8/1994 |
| KR | 990034156 A | | 3/2001 |
| KR | 000058932 A | | 4/2002 |
| WO | WO 02/058625 A3 | | 8/2002 |

OTHER PUBLICATIONS

Pan, X. et al., Zhongguo Yaolixue Yu Dulixue Zazhi (1993), 7(2), 141-144. Inhibitory effects of total saponins extracted for Panax ginseng, Panax quinquefolium and Panax notoginseng on platelet function and thrombosis in rats.*
Fang, K.-H., et al. Yaoxue Xuebao (1958), 6: 380-4. Study on the preparation of potassium antimony tartrate pills by the drop method. Abstract.*
Wolff, H. L. Apoth. Ztg. (1930), 45: 22-4. Preparation of stable digitalis pills. Abstract.*
STN Search Results, (Jun. 2005).*
Yuan, J-P et al. J. Agric. Food Chem. 1998, 46, 2651-2654. Simultaneous Determination of Rosmarinic Acid, Lithospermic Acid B, and Related Phenolics in Salvia miltiorrhiza by HPLC.*
PCT International Search Report for Yan, et al, Int'l Application No. PCT/IB03/03774, Filed Jul. 31, 2002, Dated Dec. 15, 2003.
Chinese Traditional Patent Medicine. vol. 23, No. 5, May 2001, LuoXiao-jian et al., "A Brief Account of the Study on Fufangdashen Tablets", pp. 371-373.
Chinese Pharmaceutical Patent Affair, vol. 14, No. 6, Jun. 2000. Sun Yikun et al., "Study on the Standard Specification and Investigation on Quality of Compound Danshen Tablet", pp. 383-385.
Chinese Drugs of Plant Origin, 749-750 (1992).
European Search Report for Tianjin Tasly Pharmaceutical Co., Ltd., China, European App'l No. EP 03 017260.5, Filed Jul. 30, 2003. Dated Dec. 5, 2003.
Singaporean Search Report and Written Opinion for Tianjin Tasly Pharmaceutical Co., Ltd., China, Singaporean Application No. 200304274-4, Filed Jul. 31, 2003. Dated Mar. 24, 2005.
Yang, G.Y. and Wang, Wei Clinical studies on treatment of coronary heart disease with *Valeriana officinalis* var *latifolia*. Chin J Integr Med, 14(9): 540-2 (1994) [Exhibit 4].
Wu, Y. et al. Clinical study on Xintongkang capsule in treating angina pectoris of coronary heart disease. Chin J Integr Med, 10(7):395-8 (1990) [Exhibit 5].
Liu, K.Y. et al. Clinical observation on treatment of 45 angina pectoris patients of coronary heart disease with taponin. Chin J Integr Med, 15(11):649-51 (1995) [Exhibit 6].

(Continued)

*Primary Examiner* — Michele C. Flood
(74) *Attorney, Agent, or Firm* — Finnegan, Henderson, Farabow, Garrett & Dunner LLP

(57) ABSTRACT

This invention provides compositions comprising extracts of Radix Salviae Miltiorrhizae, Radix Notoginseng and Borneol. Said compositions comprise notoginsenoside $R_1$ and ginsenoside $R_{g1}$ which are active components for therapeutic applications. This invention also provides a method of preparation of the said compositions and a method of identification and determination of the amount of individual effective components of said compositions. Finally, this invention provides various uses of the compositions.

1 Claim, 3 Drawing Sheets

OTHER PUBLICATIONS

Figure 1:
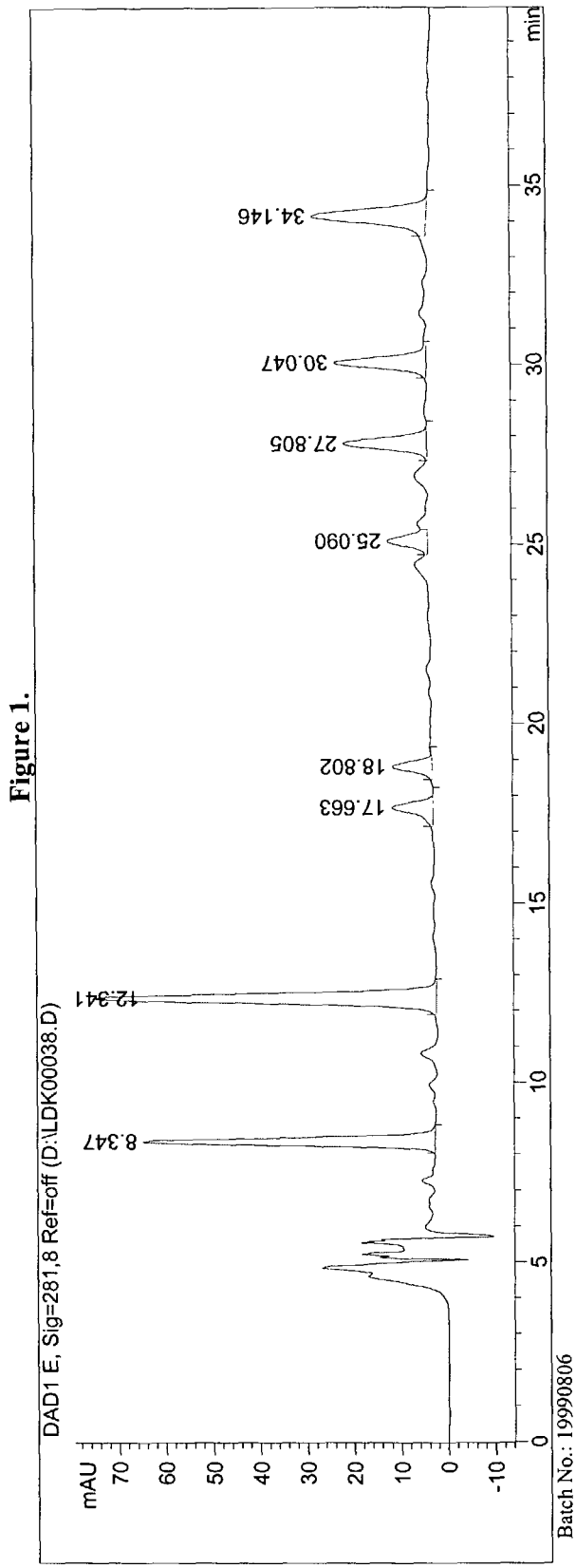

Hu, J.X. et al. Clinical and experimental study of shenshao tongguan pian in treating angina pectoris of CHD (coronary heart disease). Chin J Integr Med, 10(10):596-9 (1990) [Exhibit 7].

Li, Y. et al. Effects of Kuo-guan granule on plasma zinc, copper and erythrocyte GSH-Px (glutathione peroxidase) in patients with angina pectoris. Chin J Integr Med, 10(6):348-50 (1990) [Exhibit 8].

Wang, B. et al. Clinical observation on 406 cases of angina pectoris in coronary heart disease treated with saponin of *Tribulus terrestris*. Chin J Integr Med, 10(2):85-7 (1990) [Exhibit 9].

Jin, C. et al. Effect of *Astragalus membranaceus* on erythrocyte sodium content and sodium transport in the coronary heart disease. Chin J Integr Med, 11(11):651-3 (1991) [Exhibit 10].

Jiang, H.W. et al. Clinical study in treating qi-deficiency and blood-stasis syndrome of angina pectoris with qi xue granule. Chin J Integr Med, 12(11):663-5 (1992) [Exhibit 11].

Wang, X.F. et al. Clinical observation of wenxin decoction in treating 82 patients with spontaneous angina pectoris. Chin J Integr Med, 16(4):201-3 (1996) [Exhibit 12].

Lei, Z.Y. et al. Action of *Astragalus membranaceus* on left ventricular function of angina pectoris. Chin J Integr Med, 14(4):199-202 (1994) [Exhibit 13].

Chen, K. et al. Clinical study on the effect of shuxuening tablet in treatment of coronary heart disease. Chin J Integr Med, 16(1):24-6 (1996) [Exhibit 14].

Zhang, X.L. et al. Preliminary exploration on rose shu-xin oral liquid in treating angina pectoris of CHD. Chin J Integr Med, 12 (7) : 414-6 (1992) [Exhibit 15].

Li, Y.Y. Clinical and experimental studies on the effect of xue mai tong on coronary heart disease. Chin J Integr Med, 9(2):79-81 (1989) [Exhibit 16].

Cai, P.Y. et al. A clinical study of hehuantang in treating coronary heart disease. Chin J Integr Med, 16(4):204-6 (1996) [Exhibit 17].

Lin, Q.C., comp. A clinical study of guan mai le in the treatment of coronary heart disease. Chin J Integr Med, 9(5):280-2 (1989) [Exhibit 18].

Li, S. Q. et al. Clinical observation on treatment of ischemic heart disease with *Astragalus menbranaceus*. Chin J Integr Med, 15(2):77-80 (1995) [Exhibit 19].

Lu, B.J. et al. Effect of sheng mai san on lipid peroxidation in acute myocardial infarction patients, Chin J Integr Med, 14(12):712-4 (1994) [Exhibit 20].

Wang, S. et al. Effects of Codonopsis pilosulae on the synthesis of thromboxane A2 and prostacyclin, Chin J Integr Med, 10(7):391-4 (1990) [Exhibit 21].

The State Pharmacopoeia Commission of P.R. China, comp. Fufang Danshen Pian. Pharmacopoeia of the People's Republic of China. English Edition 2000. vol. 1, 280-81 [Exhibit 22].

Zhu, H.G. et al. Clinical study on xinkening in treating asymptomatic myocardial ischemia in coronary heart disease. Chin J Integr Med, 14(4):213-5 (1994) [Exhibit 23].

Jiang W. et al. Effects of "Danshensu" and other two water-soluble components of *Salvia miltiorrhiza* on dog ischemic myocardium and isolated pig coronary artery. Acta Acad Med Prim Shanghai, 9: 13-19 (1982) [Exhibit 24].

Sun, X.M. et al. Studies on a new pharmacological action of anextract of Den-shen (*Salvia miltiorrhiza*). Chin Med Herb, 22:20-23 (1991) [Exhibit 25].

Chen, Z.H. et al. Studies on effects of "Danshensu" on experimental microcirculatory disturbances and plasma lactic acid concentrations. Acta Acad Med Shanghai, 14(1):25-29 (1987) [Exhibit 26].

Shi, L. et al. Effects of total saponins of *Panax notoginseng* on increasing $PGI_2$ in carotid artery and decreasing $TXA_2$ in blood platelets. Acta Pharmcol Sin, 11(1):29-32 (1990) [Exhibit 27].

Xu, W. and Wang Z.R. Effect of menthol and borneol on the distribution of sulfadiazine sodium and Evan's blue in the rat and mouse brain. Pharmacol Chin Med Clin, 6:31-33 (1995) [Exhibit 28].

Chen, T.F. et al. Enhancement of absorption of tetramethylpyrazine by synthetic borneol. Acta Pharmacol Sin, 11(1):42-44 (1990) [Exhibit 29].

Li, X. et al. Protective effects of *Panax notoginseng* saponins on experimental myocardial injury induced by ischemia and reperfusion in rat. Acta Pharmacol Sin, 11(1):26-29 (1990) [Exhibit 30].

Pan, J.G. et al. Chemical Studies on Essential oils from six *Artemisia* Species. Chin J Chin Mater Med, 17:741-46 (1992) [Exhibit 31].

Wu, Y.Z. et al. On mechanism of effects of *Radix Silviae miltiorrhizae* in promoting blood circulation and removing blood stasis. Acta Nanjing Univ Trad Chin Mater Med, 11:35-6 (1995) [Exhibit 32].

Li, C.Z. et al. Experimental study on the Anti-coagulative action of Danshensu. Chin J Integr Med, 3: 297-9 (1983) [Exhibit 33].

Li, C.Z. et al. Experimental studies on the mechanism of inhibition from thrombus formation by *Silviae miltiorrhizae* bunge in vitro. Acta Acad Med Prim Shanghai, 6:145-9 (1979) [Exhibit 34].

Cheng Y.Y. et al. Effect of *Silvia miltiorrhiza* on the cardial ischemia in rats induced by ligation. Chin J Integr Med, 12:424-6 (1992) [Exhibit 35].

Xing, Z.Q. et al. Effect of *Salvia miltiorrhiza* on serum lipid peroxide, superoxide dismutase of the patients with coronary heart disease. Chin J Integr Med, 16(5):287-9 [Exhibit 36], (1996).

Chang, Y.Z. et al. Protective effect of DS-182 on the $H^+$—ATPase activity of rat myocardial mitochondria against free radical damage. Chin J of Path, 7(5): 449-52 (1991) [Exhibit 37].

Han, C. et al. The protective effects of redix *Salviae miltiorrhizae* on the ischemic and post-ischemic reperfusion injury of the heart. Chin J of Path, 7(4): 337-41 (1991) [Exhibit 38].

Wu, H.Z. et al. In vitro inhibitory effect of 764-3 on human platelet aggregation and release reaction, Chin J of Hematology, 15(9):458-60 (1994) [Exhibit 39].

Li, H.T. and Shi, L. Effects of total saponins of *Panax notoginseng* on $Ca^{2+}$ influx into myocardial cells. Acta Pharmacol Sin, 11(3):213-7 (1990) [Exhibit 40].

Hu, Y.J. et al. Effects of artificial cultured *Panax notoginseng* on cardiovascular system. Chin J Chin Mater Med, 17(6):361-3 (1992) [Exhibit 41].

Xu, Q. et al. Studies on blood-lipid decreasing action of total saponins of *Panax notoginseng* (Burk.) F.H. Chen. Chin J Chin Mater Med, 18(6): 367-8 (1992) [Exhibit 42].

Jiang W. et al. Some pharmacologic effects of the 'styrax pill for coronary disease' and the pharmacological basis of a simplified styrax-borneol preparation. Acta Pharmaceutica Sin, 14(11):665-61 (1979) [Exhibit 43].

Supplementary Partial European Search Report for Tianjin Tasly Pharmaceutical Co., Ltd., China, European Application No. EP01994322, Filed Jul. 4, 2003. Dated Jul. 22, 2004.

Li R., et al., Quantitative Determination of Total Tanshinone in *Salvia miltiorrhiza* Tablet Compound, Yiyao Gongye—Pharmaceutical Industry, Shanghai, CN; vol. 17, No. 11 1986, pp. 513-514, XP002954785.

Ni K, et al., Determination of Active Components of *Salvia miltiorrhiza* and Notoginseng in Compound *Salvia miltiorrhiza* Tablets by TLC—Densitometry, Yaowu Fenxi Zazhi—Chinese Journal of Pharmaceutical Analysis, Zhongguo Yaoxuehui, Beijing, CN, vol. 9, No. 2, 1989, pp. 74-77, XP002954784.

Liu Y., et al., Evaluation of Radix *Salviae miltiorrhizae* and Its Preparationi, Database Accession No. NLM2085402, XP002262545, Mar. 1999;15(3): 159-162.

Anonymous: Internet Article, "Online", XP002262543, "URL:http://www.carbotrading.com/Products/Medicine/JZ016.htm" Nov. 18, 2003.

Anonymous: Internet Article, "Online", XP002262544, "URL:http://www.craneherb.com/Products/product001513>" Nov. 18, 2003.

International Search Report for WO 02/058625 A3, for Tianjin Tasly Pharmaceutical Co., Ltd., China; "Herbal Composition for Angina Pectoris, Method to Prepare Same and Uses Thereof" Published Aug. 1, 2002.

Preliminary Amendment filed Jul. 30, 2004 in related U.S. Appl. No. 10/903,110.

* cited by examiner

HERBAL COMPOSITION FOR ANGINA PECTORIS, METHOD TO PREPARE SAME AND USES THEREOF

This application is a continuation-in-part of International Patent Application No. PCT/US01/49396, filed Dec. 18, 2001 which claims benefit of U.S. Ser. No. 60/258,057, filed Dec. 22, 2000, the content of which are incorporated here into this application.

Throughout this application, various publications are referenced and the disclosures of these publications are hereby incorporated by reference into this application in order to more fully describe the state of the art as known to the skilled therein as of the date of the invention described and claimed herein.

BACKGROUND OF THE INVENTION

Chronic stable angina pectoris is due to transit myocardial ischemia. Aspirin, nitrates, beta-adrenoceptor blocking drugs, and calcium channel blocking drugs used alone or in combination with one another are the commonly used drugs for angina pectoris.

Aspirin as an antithrombotic agent is a symptomatic treatment for chronic stable angina pectoris.

Nitrates are used to treat an anginal episode and can be successfully used in prophylaxis by patients with predictable symptoms. With all nitrates, troublesome headache can prevent their use in certain susceptible individuals.

Beta-adrenoceptor blocking drugs, although established as a cornerstone in the treatment of angina, are specifically contraindicated in patients with obstructive airways diseases and severe ventricular dysfunction, and relatively contraindicated in diabetes and in those with peripheral vascular disease, bradycardia or heart block.

Calcium antagonists are certainly effective in angina, achieving their effects by smooth muscle relaxation in the coronary arteries and peripheral circulation, increasing myocardial supply and reducing myocardial work.

Although there is progress in drug combination therapy in angina, which most patients begin treatment with nitrates and a beta-adrenoceptor blocking drug or a calcium antagonist, there is a need of drug for chronic stable angina pectoris which is very effective, can be taken for a long period of time and has very low toxicity.

In view of the problems of relating to the above mentioned drugs, notable efforts have been made to apply herbal Medicine as an alternative to the standard treatment of chronic stable angina pectoris. Traditional Chinese Medicine (TCM) has contributed much in this respect.

U.S. Pat. Nos. 5,288,485 and 5,433,957 refer to an extract from *Hypericum erectum thunb* for curing or preventing diseases caused by disorder in blood circulation such as angina pectoris.

U.S. Pat. No. 5,776,463 refers to an oral pharmaceutical composition containing petals of borage or extract of borage petals for the prevention and treatment of stress which is associated with circulatory heart diseases including angina.

In addition to *Hypericum erectum thunb* and borage petals, many other herbal plants have also been used to treat angina. One such plant is *Valeriana officinalis latifolia*. Yang G Y et al (1994) Reported that 82 patients with angina pectoris had been treated with *Valeriana officinalis latifolia*, among whom ST-T ischemic changes appeared on ECG in 50 cases before treatment. Its total effective rate for simple angina (without detectable ischemic findings) was 87.80%; the angina with ischemic findings, 88.00%. In addition, it was discovered that *Valeriana officinalis latifolia* could lower plasma lipids as well. No toxic actions to liver, kidney, and hemopoietic tissue, have been found. (1) Wu Y (1990) reported that in a setting of 267 patients with angina pectoris, 93.3% of the patients treated with xintongkang capsule was effective.

Another herbal preparation called Shenshao tongguan pian was used in treating angina pectoris. In 1990, Hu J X et al. Reported that the Shenshao tongguan pian is composed chiefly of saponin from the stem and leaves of Ginseng and Radix *Paeoniae alba*, etc. The total effective rate for treating angina pectoris was 94.71%. And the ECG improvement rate was 63.38%. In addition, laboratory examination also revealed that Shenshao tongguan pian could promote the left ventricular output, lower the blood viscosity and inhibit the aggregation of blood platelet. Both acute and chronic toxicity tests showed that Shenshao tongguan pian has no toxicity or side effects.

Kuo-guan granule is another herbal preparation for angina pectoris. Li Y et al. (1990) reported that the changes of the plasma zinc, copper and erythrocyte glutathione peroxidase were measured by atomic absorption spectrometry and DTNB color development in 31 patients suffering from coronary heart disease with angina pectoris before and after taking Kuo-Guan granule for one month. The results indicated that the plasma zinc and erythrocyte glutathione peroxidase were lower and copper was higher in the patients than the normal control group before treatment ($P<0.01$), the plasma zinc and erythrocyte glutathione peroxidase increased and copper decreased after treatment ($P<0.01$). These suggest that therapeutic mechanism of Kuo-Guan granule for coronary heart disease with angina pectoris may relate to its regulation on trace elements disturbance in body.

Saponin of *Tribulus terrestris* was another herbal composition for treating angina pectoris.

Fufang Danshen Pian is a folk prescription of Dan Shen Tablet which indicate for treating chronic stable angina pectoris due to coronary artery ischemia and has been officially listed in the editions of Chinese Pharmacopoeia since 1977 and applied to clinical use for decades.

Fufang Danshen Pian contains multiple active extracts of botanical including Danshen (Radix Salviae Miltiorrhizae), and Sanchi (Radix Notoginseng). Both of the botanical were first documented in Shen Nong Ben Cao Jing (Shen-nong's Herbal Pharmacopoeia) completed in 200. Fufang Danshen Pian also contains synthetic borneol, a version of a natural borneol (Bingpian). Natural borneol was first documented in Tang Ben Cao (Herbal Pharmacopoeia of the Tang Dynasty) compiled around 659.

Li Cheng-zhu et al (1979) reported in (Acta Acad Med Prim Shanghai) on an experimental study of thrombotic inhibition effect of Radix Silviae Miltiorrhizae. Effects on in vitro thrombosis, functions of platelet and coagulation, fibrinolysis were observed in rabbits. After injection of Radix Silviae Miltiorrhizae, 3 links were found to play an important role in inhibition of in vitro thrombosis: (1) inhibition of platelet function; (2) inhibition of coagulation function; and (3) promote fibrinolysis. Of which, the former two mechanisms function more intensely. The results conform to those in the treatment of thrombotic diseases, especially arterial thrombotic diseases.

Chiang W T et al (1982) reported in (Acta Acad Med Prim Shanghai) the effects of "Danshensu" and other two water-soluble components of *Salvia miltiorrhiza* on dog ischemic myocardium and isolated pig coronary artery. The effect of 3 new water-soluble components i.e. Danshensu (DS-182, D(+)-3,4-dihydroxyphenyl lactic acid), protocathu-aldehyde (PCAD) and an impure diterpene acid (DS-187) isolated from Salvia miltiorrhiza bunge, were compared with those of dipyridamole. Results revealed (1) in mice, DS-182 gave significant protection against hypoxia, whereas PCAD was ineffective; (2) DS-182 could nullify the pituitrin-induced electrocardiographic ischemic ST-T elevation but had no influence on the reduced heart rate. DS-187, PCAD and dipyridamole only showed incomplete protection; (3) in the acutely infarcted dog model prepared by ligation of the anterior descending branch of the left coronary artery, the benefits achieved by intravenous injection of DS-182 proved superior to DS-187 and PCAD in respect to the left ventricular function, left ventricular peak systolic pressure (LVPSP) and left ventricular end diastolic pressure (LVEDP). PCAD, on the contrary, produced adverse effects on LVPSP and LVEDP. Intravenously administered dipyridamole, though it did not change LVEDP, suppressed LVPSP significantly with marked hypotensive effect. All these components of Salvia and dipyridamole significantly reduced the ultimate myocardial infarct size (N-BT assessment); Ds-182 was most effective, dipyridamole and DS-187 the next, while PCAD the least; (4) in the isolated perfused pig coronary artery preparation, DS-182 significantly reduced the resistance of the coronary vessel, whereas either DS-187, PCAD or sodium Tanshinone II-A sulfonate (DS-201), another component of Salvia, increased it. The constrictory action of morphine and propranolol on the isolated coronary artery preparation was antagonized by the prior administration of DS-182. All of these suggested that Danshensu might be the main active principle of *Salvia miltiorrhiza* in treating ischemic heart disease and that its concomitant use with propranolol or morphine would be beneficial.

Li Cheng-zhu et al (1983) reported in (Chin J Integr Med) the anti-coagulation effect of Radix Silviae Miltiorrhizae. Danshensu is a water-soluble monomer extracted from Radix Silviae Miltiorrhizae. It is also the main ingredient of commercially sold Injection Radix Silviae Miltiorrhizae. The present study proved that Danshensu inhibits thrombosis in vitro, aggregation of platelet (induced by ADP), and internal and external coagulation systems; diminishes the number of platelets and promotes the degradation of fibrin or fibrinogen. The effects peaked 30 minutes after a single injection of 20 mg/kg in rabbits, lasted for 1 hour, and recovered gradually. 4.5 hours after injection, all recovered to normal but thrombosis test in vitro. Chen Zhanghua (1987) reported in Acta Acad Med Prim Shanghai on effects of "Danshensu" on experimental microcirculatory disturbances and plasm lactic acid concentrations. Natural Danshensu is a water soluble monomer extracted from Radix Salviae Miltiorrhizae (RSM). Microcirculatory disturbances in rabbits were induced by intravenous injection of high molecular weight dextran. Natural Danshensu (dosage 4-6 mg/kg) markedly increased the number of capillary vessels in the bulbar conjunctiva, and also decreased the concentration of plasm lactic acid in the rabbits. Mesenteric microcirculatory disorders were produced by local noradrenaline (4 g) drip in mice. Natural Danshensu dilated the arteries and accelerated the speed of blood flow, thus eliminating microcirculatory blood stasis. In our experiments, effects of synthetic Danshensu were observed concomitantly. The results showed that there was no significant difference between natural and synthetic Danshensu in relieving microcirculatory disturbances.

Sun Xi-ming et al (1991) reported a new pharmacological action of an extract of Danshen (*Salvia miltiorrhiza*). The paper reports that an extract of Danshen (*Salvia miltiorrhiza*) which contains the sodium salts of D(+)-(3,4-dihydroxy phenyl) lactic acid was found to possess a new pharmacological action of decreasing the biosynthesis of cholesterol in cells and anti-lipoprotein oxidation, by cell cultural studies. When compared with the control, its electrophoretic migration rate was markedly lowered and MDA content and cytotoxicity decreased obviously. These results indicated that salts of D(+)-(3,4-dihydroxy phenyl) lactic acid may be effective in the prevention and treatment of atherosclerosis.

Zheng Ruo-xuan et al (1992) reported in (Chin J Integr Med) the preservation effect of Radix Silviae Miltiorrhizae on myocardial ischemia induced by coronary ligation in mice. Obvious preservation effect on acute myocardial ischemia in mice by coronary ligation could be obtained after i.p. water-extract of Radix Silviae Miltiorrhizae (5 g crude drug/kg). S-T segment elevation on ECG due to myocardial ischemia in the treatment group was much lower, ischemic size of the left ventricle was smaller and the survival rate was higher when compared with the control.

Wu Yao-zhong et al (1995) reported in (Acta Nanjing Univ Trad Chin Mater Med) on effects of Radix Silviae Miltiorrhizae in promoting blood circulation by removing blood stasis. Pharmacological research of Radix Silviae Miltiorrhizae is common. However, rheological studies on Radix Silviae Miltiorrhizae by assessing PGI2, ET, and TXA2 produced by platelet are seldom. Influence of Radix Silviae Miltiorrhizae on thrombosis, changes of PT, KPTT, FG, ESR and HCT, and aggregation of platelet in rabbits are evaluated in the present study. Conclusions are that Radix Silviae Miltiorrhizae reduces the synthesis of TXA2 and decreases the effects of enhancement of platelet aggregation and thrombosis.

Shi Lin et al (1990) reported in (Acta Pharmcol Sin) on the effects of total saponins of Panax Notoginseng on increasing $PGI_2$ in carotid artery and decreasing TXA2 in blood platelet. Total saponins of Panax notoginseng (PNS) were given orally 100 mg/(kg·day) to rabbit for 8 wk. Aortic atherosclerotic plaque formation was restrained as compared that of to the control group. Radioimmunoassay was used to investigate the effects of PNS on the contents of prostacyclin in carotid artery and thromboxane A2 in rats' blood platelet. Oral administration of PNS 25, 50, 100 mg/(kg·day) for 10 days caused an increase of prostacyclin in carotid artery and a decrease of thromboxane A2 in blood platelet as compared with the control group. These results showed that the anti-atherosclerotic action of PNS may be a result of the correction of the imbalance between prostacyclin and thromboxane A2.

Li Xing et al (1990) reported in (Acta Pharmacol Sin) the Protective effects of Panax Notoginseng saponin on experimental myocardial injury induced by ischemia and reperfusion in rats. Effects of total saponin of Panax Notoginseng (PNS) and purified ginsenoids $R_{b1}$ and $Rg_1$ from PNS on myocardial injury induced by cardiac ischemia and reperfusion were studied using rat hearts in situ and in vitro. In pentobarbital-anesthetized rats, PNS pretreatment (100 and 200 mg/kg) provided significant reduction in myocardial infarcted size after left descending coronary artery ligation (40 min) and reperfusion (120 min) in comparison with the control. PNS 12.5 and 25 mg/L, $R_{b1}$ 10 mg/L and $R_{g1}$ 110 mg/L significantly decreased cardiac CPK release, attenuated myocardial $Ca^{++}$ accumulation, reduced malondialdehyde (MDA) production and prevented reduction of superoxide dismutase (SOD) activity in comparison with the control in perfused isolated rat, hearts with global ischemia (40 min) and reperfusion (15 min) The results showed that PNS, $R_{b1}$ and $R_{g1}$ prevented cardiac ischemia and the action was considered to be related to the inhibition of lipid peroxidation.

Huang Cong et al (1991) reported in (Chin Bull Pharmacol) the effects of Panax Notoginseng Saponin on myocardial ischemia and reperfusion injury in conscious rabbits. The effects of Panax Notoginseng saponin (PNGS) on myocardial ischemia and reperfusion injury in conscious rabbits were studied with observation of changes in electrocardiogram (ECG), the activities of creatine phosphokinase (CPK) and lactate dehydrogenase (LD) and the size of ischemic area. PNGS at the dose of 50 mg/kg and 100 mg/kg significantly reduced the size of myocardial ischemic area. These results suggested that PNGS have the protective effects on myocardial ischemia and reperfusion injury.

Mo Qi-xian et al (1987) reported in (Propriet Trad Chin Med Res) the dynamics of $^3$H-Borneol. In order to highlight the mechanism of inducing resuscitation of Borneol aromaticity, dynamics of 3H-Borneol were conducted by intraveneous injection and oral administration. The results revealed that the half-life time was 2.8 min after a single intravenous injection of 3H-Borneol. It suggested that the drug distributed rapidly to the relevent organs and tissues after administration and produced prompt effect. In vivo distribution concentrated on organs and tissues which are abundant in blood flow, such as heart, lung, liver, kidney and brain, etc. This provided clinical application certain theoratical basis. Since the diminishing half-lifetime was 5.3 hours after oral administration of the drug, this suggested that oral Borneol could not lead to accumulation, but poor bioavail-ability. Further studies should be taken to discusse the relationship with drug dose and dosage form.

Chen Tie-feng et al (1990) reported in (Acta Pharmacol Sin) the enhancement of absorption of tetramethylpyrazine by synthetic borneol. Sprague-Dawley rats were given ig tetramethylpyrazine phosphate (TMP) 5 mg/kg with or without previous borneol 5 mg/kg. The plasm TMP concentrations were analysed by GC method, and the data were treated by NONLIN program. The Cmax were 931 and 562 ng/ml, respectively, ($p<0.01$); while the AUC were 68849 and 37174, respectively, ($P<0.05$). It is suggested that the borneol enhances the absorption of the TMP but not in elimination.

Xu Wei et al (1995) reported in (Pharmacol Chin Med Clin) the effect of menthol and borneol on the distribution of sulfadiazine sodium and Evan's blue in the rat and mouse brain. Menthol (1.5 g/kg, ig) and Borneol (1.5 g/kg) prolonged the sulfadiazine sodium distribution half-life $t_{1/2}$ in rats. The above dosage of menthol and borneol given orally also increased the concentration of sulfadiazine sodium in the rat brain. Menthol (ig 0.5 g/kg for 3 days) and borneol (ig 0.5 g/kg for 3 days) promoted the concentration of Evan's blue in the mouse brain, but the value of concentration was significantly lower than that of the mice suffering from the ischemia-reperfusion injury. The results suggested that the menthol and borneol could enhanced the sulfadiazine sodium transfer in brain-blood barrier with no damage to brain-blood barier.

In the United States, coronary atherosclerotic heart disease is the commonest cause of cardiovascular disability and death.

Atherosclerosis is an arterial disorder characterized by yellowish plaques of cholesterol, lipids, and cellular debris in the inner layers of the walls of large and medium-size arteries. The condition begins as a fatty streak and gradually builds to a fibrous plaque or atheromatous lesion. The blood vessel walls become thick, fibrotic, and calcified. The artery lumen narrows. Many atherosclerotic plaques remain stable or progress gradually. Others may rupture resulting in hemorrhage, platelet activation, and thus intravascular thrombosis. Coronary thrombosis causes partial or complete vessel occlusion, impairs blood flow, thus leads to unstable angina or myocardial infarction. Alternately, the ruptured plaques may become restabilized, often more severe stenosis.

Exercise and mental stresses increase myocardial oxygen demand. Under normal physiological condition, increased myocardial oxygen demand is met by the arterioles dilating thus increasing blood flow. In the presence of atherosclerosis, the arterioles may dilate maximally to meet basic demand. Such dilated arterioles may be unable to meet the increased myocardial oxygen demand. When oxygen demand exceeds oxygen supply, the ischemia of myocardium occurs. Alternately, severe vessel occlusions may limit blood flow thus cause myocardial ischemia. Clinical manifestations of transient myocardial ischemia is angina pectoris which is a paroxysmal thoracic pain, frequently spread to the arms, particularly to the left arm, with or without accompanied by a feeling of suffocating and impending death.

Angina pectoris is subdivided in to two: stable and unstable. Stable angina pectoris is caused by the increased myocardial oxygen demand in most cases. Stable angina thus attacks in the predictable frequency and duration upon provocation which increases myocardial oxygen requirements such as exercise, mental stress, etc. In contrast, unstable angina pectoris attacks without provocation and usually caused by decreased oxygen supply to myocardium. Plaque disruption, platelet plugging, and coronary thrombosis decrease oxygen supply to myocardium.

Angina pectoris is treated with various drugs, surgical procedure, coronary artery bypass graft, balloon-angioplasty, stent placement, etc. Therapy for stable angina pectoris is primarily to minimize myocardial oxygen demand as well as a preventive measure. Therapy for the acute syndrome unstable angina pectoris is primarily to inhibit platelet activation and thrombolysis.

Current therapeutic agents for chronic stable angina pectoris are nitroglycerine, other nitrates, calcium channel blockers, and beta-adrenergic receptor blockers. These drugs, administered alone or in combination with other drugs, alleviate or prevent rather than cure angina.

When angina attacks, nitroglycerine is administered sublingually to alleviate symptoms. Nitroglycerine is also applied to prevent anginal attacks caused by exertion and stress. Nitrates are applied to prevent angina attacks. Nitroglycerine and nitrates mediate their effect primarily by relaxing vascular smooth muscle, reducing myocardial activity, and thus reducing myocardial oxygen demand. The side effects are throbbing headache, dizziness, weakness, orthostatic hypotension, tachycardia, etc.

Beta-adrenergic receptor blockers such as propranolol are applied to prevent angina pectoris by reducing myocardial oxygen requirements during exertion and stress. The major contraindications are bronchospastic disease, bradyarrhythmias, and overt heart failure. In individuals with asthma and other forms of airway obstruction, beta-blockers may worsen their condition.

Calcium antagonists are applied to prevent angina pectoris by reducing the oxygen demand of myocardium. Myocardium is dependent on calcium influx for normal functions. By inhibiting calcium influx, calcium antagonists may relax smooth muscle of the blood vessel, decrease myocardium activity, reduce oxygen demand by myocardium, and thus prevent angina pectoris. Calcium antagonists have adverse side effects. The mild side effects are flushing, edema, dizziness, nausea, etc. Excessive inhibition of calcium influx to myocardium may cause severe side effects such as cardiac arrest, bradycardia, artrioventricular block, congestive heart failure, etc. Combined with beta-adrenergic drugs, the side effects of calcium antagonists are often augmented.

In China, Panax Notoginseng and Radix Salviae Miltorrhizae have been used for treating cardiovascular disease since 200 AD (Shen-nong's Herbal Pharmacopoeia). Panax Notoginseng has been used for treating angina pectoris. Radix Salviae Miltiorrhizae has been used for promoting blood circulation and dispersing blood stasis. Numerous preclinical and clinical studies demonstrate the efficacy and safety of Panax Notoginseng and Radix Salviae Miltiorrhizae.

Traditional Chinese medicine is the mixture of several herbs requiring decoction. A modified form of Chinese medicine for treating coronary heart disease is Dan Shen tablet. Dan Shen tablet is a large unctuous ball, often as large as 1 cM in diameter. Dan Shen tablets are made of the extract of Radix Salviae Miltiorrhizae, powder of Panax Notoginseng and synthetic borneol, have been listed in the Chinese Pharmacopoeia since 1977, and have been used to treat cardiovascular disease for decades.

The disclosed Danshen pill (DSP) or called cardiotonic pill is a generation Chinese medicine for coronary heart diseases. Chinese medicine consists of various herbs which vary from prescription to prescription in regard to the type of herbs as well as the proportion of herbs. To control the quality, DSP is manufactured with the standardized formula. The therapeutic components of DSP are the water-soluble extracts of Radix Salviae Miltiorrhizae 10-30% and sometimes, approximately 20%, the water-soluble extracts of Panax Notoginseng (2-6%), and borneol (1-3%). Furthermore, to alleviate angina quickly, DSP has been manufactured as a small pill which can be dissolved immediately upon sublingual administration, delivered to myocardium quickly, and thus alleviate angina fast.

DSP has been proven to be nontoxic and effective for the prevention and treatment of cardiovascular disease caused by coronary artery ischemia in preclinical and clinical studies. Furthermore, the superior efficacy of DSP to Dan Shen tablets for treating coronary arterial disease has been demonstrated in preclinical as well as in clinical studies.

DSP has been listed in the Supplement Edition of Chinese Pharmacopoeia since 1998, approved by the Chinese Ministry of Health, marketed as a drug in China since 1993, and used by more than five million people.

SUMMARY OF THE INVENTION

The disclosed Dan Shen Pill (DSP) is a generation of Chinese medicine for treating coronary heart disease manufactured with the standardized formula. DSP comprises the standardized amount of the extracts of Panax Notoginseng, the extracts of Radix Salviae Miltorrhizae, and Borneol.

Panax Notoginseng is included to alleviate and to prevent angina. Radix Salviae Miltorrhizae is included to inhibit platelet activation, to prevent coronary thrombosis, and thus to promote blood circulation. Borneol is included for the effective delivery of therapeutic components to myocardium.

DSP is manufactured as a small pill, approximately 25 mg, which can be dissolved immediately upon sublingual administration and thus to mediate its therapeutic effects quickly. The efficacy of DSP alleviating and preventing angina has been proven in preclinical and clinical studies.

This invention discloses a dropping machine by which DSP or other small size pills can be manufactured.

This invention discloses a method of controlling the quality of medicaments by identifying and quantitating the therapeutic components in medicaments applying analytical techniques, such as thin layer chromatography, high performance liquid chromatography, etc.

DETAILED DESCRIPTION OF THE FIGURES

FIG. 1. Batch No. 19990806
FIG. 2. Batch No. 19990815
FIG. 3. Batch No. 19990823

The position of fingerprint peaks: Group I consisting of peak 1 and 2 (retention time ranging from 7 to 15 min); Group It consisting of peak 3 and 4 (retention time ranging from 15 to 20 min); Group III consisting of peak 5, 6, 7 and 8 (retention time ranging from 20 to 40 min). From whole sight, the abundance of peaks in the group I is largest, and that the height of peak 1 is close to the peak 2. The peaks in the group II stand side by side, posses same heights almost and the abundance is very small. The group III is composed of 4 peaks, and their height increase step by step. These three groups compose the representative fingerprint of Compound Danshen Dripping pills.

DETAILED DESCRIPTION OF THE INVENTION

This invention provides a method for identifying Sodium Danshensu and protocatechuic aldehyde in a herbal composition capable of treating chronic stable angina pectoris by thin layer chromatography comprising the steps of (a) preparing the assay: (i) dissolvinjg an appropriate amount of the said composition in methanol, (ii) contacting an appropriate amount of the solution onto a silicon G gel plate containing 0.5% CMC-Na, (iii) developing the plate with a developing solution consisting of Chloroform, acetone and methane acid in the ratio of 10:4:1.6, (iv) drying and fumigating the plate with ammonia and laying the plate up for 15 minutes, (v) checking the plate under ultraviolet light, the spot representing the said composition should be at the corresponding position of the standards and show the same color; and (b) using Sodium Danshensu and protocatechuic aldehyde as the standards.

This invention also provides a method for identifying gypenoside of an herbal composition capable of treating chronic stable angina pectoris by thin layer chromatography comprising the steps of (a) preparing the assay: (i) dissolving an appropriate amount of the said composition in ammonia solvent, (ii) applying the dissolved composition into the macroporous adsorption resin column; the speed is 0.5/minute, (iii) washing the macroporous adsorption resin column and eluting the macroporous adsorption resin column with methanol, (iv) collecting the eluant, (v) contacting the eluant onto a silicon G gel plate containing 0.5% CMC-Na, (vi) developing the plate with 10 ml developing solution, (vii) after being dried and sprayed with 10% ethanol sulfate, the plate is baked at 105° C. for several minutes, (viii) checking the plate under normal light, the spot representing the said composition should be at the corresponding position of the standards and show the same color; and (b) using total gypenoside, Saponin R1 and ginsenoside Rg1 as the standards.

This invention further provides a method for identifying a herbal composition capable of treating chronic stable angina pectoris comprising the steps of (a) preparing the assay: (i) dissolving a suitable amount of Dan Shen Dropping Pellet composition in internal standard para-aminobenzonic acid solvent, (ii) diluting the solution with methanol and centrifuging, (iii) collecting the supernatant; (b) using Danshensu and protocatechuic aldehyde as the standards; (c) performing the HPLC assay; and (d) calculating according to the internal standard method.

In addition, this invention provides a composition comprising the product that when subjected to the above method produces 8 peaks as shown in FIG. 1 and produces a fingerprint as tabulated here

| Peak No. | Retention Time | Relative Retention Time | Appearance Probability | Area | Area Ratio | Area Ratio Range |
| --- | --- | --- | --- | --- | --- | --- |
| 1 | 8.289 | 0.672 | 100% | 1034.276 | 0.572 | 0.572 ± 0.096 |
| 2 | 12.343 | 1.000 | 100% | 1817.065 | 1.000 | 1.000 ± 0.000 |
| 3 | 17.493 | 1.417 | 100% | 376.547 | 0.208 | 0.208 ± 0.040 |
| 4 | 18.664 | 1.512 | 100% | 328.011 | 0.181 | 0.181 ± 0.059 |
| 5 | 24.883 | 2.016 | 100% | 486.626 | 0.267 | 0.267 ± 0.097 |
| 6 | 27.586 | 2.235 | 100% | 525.432 | 0.289 | 0.289 ± 0.052 |
| 7 | 29.714 | 2.407 | 100% | 940.963 | 0.516 | 0.516 ± 0.125 |
| 8 | 34.030 | 2.757 | 100% | 1547.495 | 0.850 | 0.850 ± 0.163 |

The invention provides an herbal composition capable of treating chronic stable angina pectoris comprising about 0.14 to about 0.18 mg Danshensu per pill. This invention also provided the above composition comprising more than 12.12 μg sanchinoside R1 per pill and more than 56.26 μg ginsenoside Rg1 per pill. This invention further provides the above composition comprising about 10-30% water soluble phenolic acid components from Radix Salviae Miltorrhizae, 2-6% extract of saponin from Radix Notoginseng, and about 1-3% borneol with pharmaceutically suitable carriers.

The present invention provides a method for obtaining an herbal composition capable of treating chronic stable angina pectoris comprising the steps of (a) Applying Radix Salviae Miltorrhizae into the multifunction extraction tank; add water until it is 15-20 cm over the herb (about 5-7 times the quantity of the herb); heat them up to boiling with steam, while the inside air pressure should be controlled in between 0.04-0.06 mPa; keeping the tank in boiling condition. Boiling twice, first for 2 hours and then for 1.5 hours. The extract is filtrated at the bottom of the extraction tank through a 100-mesh net into a stock tank, the remaining is discarded; (b) Transferring the solution from the stock tank into a vacuum tank. The steam is controlled at below 0.05 mPa. In the mean time, adjust the vacuum to 0.076~−0.088 mPa to keep the tank in boiling condition. The solution is concentrated to about the solution volume (Liter) to the herb quantity (kilogram) in the ratio of 1:1; (c) Filtering and adding 95% ethanol to the solution with slow stirring until the ethanol concentration of the solution reaches 70% measured by ethanol gravimeter for 24 hours; (d) Opening the tank, transferring the supernate of the ethanol precipitated solution through 100 mesh net into a vacuum concentration tank, adjusting the air input to 0.04-0.06 mPa and the vacuum to −0.076~−0.088 mPa to keep the tank boiling but bumping and recovering the ethanol to the herb solution to about the solution volume (Liter) to the herb quantity (kilogram) in the ratio of 1:1; (e) Loading the solution from step (d) into the pre-treated polyamide chromatography with the loading volume 5 ml/gram polyamide and washing the column with 3 volume times water, eluting the column with 5-10 times 95% ethanol; and (f) Recovering the ethanol as in the step d to concentrate the eluant to the density of 1.33-1.35.

The present invention also provides a method for obtaining an herbal composition capable of treating chronic stable angina pectoris comprising steps of (a) applying Radix Notoginseng into the multi-function extraction tank; add water until it is 15-20 cm over the herb (about 5-7 times the quantity of the herb; heat up to boiling with steam, while the inside air pressure should be controlled in between 0.04-0.06 MPa; keeping the tank in boiling condition, boiling twice, first for 2 hours and then for 1.5 hours, filtering the extract at the bottom of the extraction tank through a 100 mesh net into a stock tank, and discarding the remainder; (b) Macroporous adsorption resin: (i) Pre-treatment of macroporous adsorption resin: After being soaked in 95% ethanol for 24 hours, non-polarity macroporous adsorption resin ZTC-1, With particle size 0.3-1.2 mm and average aperture 130-300 A, is filled into a column. Wash the column with ethanol and equal volume of water until the eluant is clear with equal volume of water; or after washing the column with 0.1-1 mol/L NaOH or HCL, wash the column with water until the eluant has no ethanol smell or is close to pH neutral, (ii) Loading the extract of Radix Notoginseng from Step (a), 1 g/1 g resin with flow rate at 0.5-5 cm/cm²/min, washing the column until the eluant is clear, Eluting with 70% ethanol. The flow rate is 0.5-5 cm/cm²/min. Collect the eluant, (iii) Recovery resin. Wash the column with 95% ethanol until the eluant is without color and clear after adding equal volume of water. Then wash the column with water until there is no ethanol smell; and (c) Applying the 75% ethanol eluant through 100 mesh net to a vacuum concentration tank, adjusting the air input to 0.04-0.06 mPa and the vacuum to −0.076~−0.088 mPa to keep the tank boiling but bumping. Recover the ethanol until the density of the eluant reaches 1.33-1.35., thereby obtaining the extract of Notoginseng saponin.

In addition, the present invention provide a method for obtaining the dropping pellets of a herbal composition capable of treating chronic stable angina pectoris comprising the steps of (a) Mixing the Unctuous of the Radix Salviae Miltorrhizae and saponin from Radix Notoginseng, boneol and poly 6000 in the melting tank by stirring to homogenize the mixture, heating it to 80-85° C. by steaming, melting the mixture for 30-40 minutes until there are no lump particles in the melted mixture; (b) Transferring the melted mixture to the dropping pot of the dropping machine where the temperature is about 89-93° C.; The cooling solution is liquid paraffin of which the temperature is lower than 8° C.; The inner diameter of the dropping head is 1.7 mm, and the outer diameter of the dropping head is 2.4 mm. The distance between the drug liquid and the dropping head is 5-6 cm; the distance between the dropping head and the cooling solution is 26-31 cm. The depth of the cooling solution is about 1 meter; The dropping speed is 60-80 pellets/min; and (c) Take the dropping pellets from the cooling oil and put them into a centrifuge for de-oilization; The speed is 800-1100 r/min for 15 minutes, thereby producing dropping pellets.

The present invention also provides the method above, wherein the macroporous resins are packed in columns. The present invention also provides the method above, wherein the chromatographic material is selected from porous polymer, silicon gel, aluminum oxide, polyamide, activated charcoal, cellulose or sephadex in addition to macroporous resin (model D101). The present invention further provides the method above, wherein the chromatographic column eluate is concentrated at reduced pressure under 60° C. to a relative density of 1.33-1.35.

This invention provides an herbal composition, capable of treating chronic stable angina pectoris, of which the outward appearance is in a homogeneous round ball shape in the same red-brown or brown-black color with aromatic smell, bitter taste. This also invention provides the composition above, of which the weight difference is about +15% within the range between 21.25-28.75 mg (average pellet weight is 0.02500 g, RED=0.21); the density is 1.13-1.40 mg/mm$^3$; and the diameter of the pellet is 0.33-0.34 cm, RED=3.42.

This invention provides the composition comprising the product produced by the above methods. This invention also provides a pharmaceutical composition comprising an effective amount of the composition above and a pharmaceutically acceptable carrier. This invention further provide the formulation above, wherein the formulation is a pill, capsule, granule, tablet, suspension, injection, syrup, or tincture.

This invention provides a method for treating stable angina pectoris in a subject by administering to the subject an effective amount of the above pharmaceutical compositions. This invention also provides a method for improving ischemic electrocardiogram by administering to the subject an effective amount of the above pharmaceutical compositions. This invention further provides a method for relieving angina pectoris by administering to the subject an effective amount of the above pharmaceutical compositions. In addition, this invention provides a method for reducing the usage of nitroglycerin by administering to the subject an effective amount of the above pharmaceutical compositions.

The present invention provides a method for relieving palpitation by administering to the subject an effective amount of the above pharmaceutical compositions. The present invention also provides a method for decreasing cholesterol and triglyceride level in blood for a subject with abnormal blood-lipid by administering to the subject an effective amount of the above pharmaceutical compositions. The present invention further provides a method for decreasing platelet aggregation in blood by administering to the subject an effective amount of the above pharmaceutical compositions. In addition, the present invention also provides a method for improving exercise tolerance and extending exercise duration, interval between exercise initiation and angina occurrence and interval between exercise initiation and 1 mm. decrease of ST segment by administering to the subject an effective amount of the above pharmaceutical compositions.

This invention provides a method for treating angina pectoris of various kinds and degrees induced by coronary heart diseases by administering to the subject an effective amount of the above pharmaceutical compositions. This invention also provides a method for antioxidizing and clearing free radicals by administering to the subject an effective amount of the above pharmaceutical compositions. This invention further provides a method for treating brain injury caused by oxygen free radical-induced lipid peroxidation by administering to the subject an effective amount of the above pharmaceutical compositions. In addition, This invention provides a method for treating hepatic injury caused by oxygen free radical-induced lipid peroxidation by caused by oxygen free radical-induced lipid peroxidation by administering to the subject an effective amount of the above pharmaceutical compositions.

This invention provides a method for treating chronic heart disease caused by oxygen free radical-induced lipid peroxidation by administering to the subject an effective amount of the above pharmaceutical compositions. This invention also provides a method for treating coronary heart disease caused by oxygen free radical-induced lipid peroxidation by administering to the subject an effective amount of the above pharmaceutical compositions. This invention further provides a method for treating essential hypertension by administering to the subject an effective amount of the above pharmaceutical compositions.

The present invention provides a composition of the medicament Dan Shen Pill (DSP) comprising (a) extracts of Radix Salviae Miltorrhizae, water-soluble extracts of *Panax ginseng*, and Borneol; (b) Radix Salviae Miltorrhizae, Notoginseng, borneol, and carriers; and (c) Radix Salviae Miltorrhizae, Panax Notoginseng, borneol, and pharmaceutical carriers.

The present invention provides the use of DSP for (a) treating coronary heart disease; (b) treating coronary heart disease in conjunction with other drugs; (c) primary prevention of coronary heart disease; (d) primary prevention of coronary heart disease in conjunction with other drugs; (e) secondary prevention of coronary heart disease; (f) secondary prevention of coronary heart disease in conjunction with other drugs; (g) reducing glycerine intake by angina patients; and (h) reducing serum cholesterol level.

The present invention further provides a method for controlling the quality of medicaments by standarizing the composition and the concentration of therapeutic substances in a medicament by analyzing and identifying therapeutic components using analytical techniques comprising the steps of (a) fractionating a medicament using analytical techniques; and (b) identifying and quantitating therapeutic substances contained in a medicament by comparing with the analytical profile of the relevant purified substances as standard.

The present invention further provides a dropping machine for manufacturing a small-sized medicament, which can be readily dissolved thus readily delivered to organs, comprising the parts of (a) a dropping pot of which temperature is 60-100° C.; (b) liquid paraffin cooling solution of which temperature is lower than 8° C.; (c) a dropping head with 1.8 mm inner diameter and 2.35 mm outer diameter; (d) a dropping head distanced from the surface of cooling solution by approximately 15 cm; (e) a dropping head distanced form the cooling solution by approximately 0.5-1.5 M; and (f) a dropping head with the speed of over 30 pellets per minute.

This invention provides a method of treating and preventing cardiovascular diseases with a composition, wherein said composition comprises 1-10% Panax Notoginseng extracts. This invention also provides a method of treating and preventing cardiovascular diseases with a composition, wherein said composition comprises 5-40% Radix Salviae Miltorrhizae extracts. This invention further provides the method above, wherein said composition comprises 1-5% Borneol additionally. In addition, this invention provides the method above, wherein said composition further comprises 1-5% Borneol. And this invention provides the method above, wherein said composition comprises 1-5% Borneol additionally.

This invention provides a method of treating and preventing cardiovascular disease coronary heart disease comprising the step of administering an effective amount above to the subject. This invention also provides a method for treating and preventing cardiovascular disease comprising the step of administering an effective amount above in conjunction with other drugs to the subject. This invention further provides a method of reducing nitroglycerin intake, wherein said method comprising the step of administering an effective amount above. In addition, this invention provides a method for reducing serum cholesterol level, wherein said method comprising the step of administering an effective amount of claim above.

The present invention provides a method of determining whether pharmaceutical compositions are capable of treating and preventing cardiovascular disease, wherein said method comprising the steps of (a) fractionating pharmaceutical compositions by high performance liquid chromatography (HPLC); (b) comparing the retention time of the fractions of pharmaceutical compositions with the retention time of saponin R1, saponin Rg1 and saponin Re; and (c) determining if pharmaceutical compositions contain fractions of which retention time is equivalent to the retention time of saponin Ri, saponin Rg, and saponin Re.

The present invention also provides a method of determining if pharmaceutical compositions are capable of treating and preventing cardiovascular disease, wherein said comprising the steps of (a) fractionating a pharmaceutical composition by thin layer chromatography (TLC); (b) comparing the position and color of the fractions of pharmaceutical compositions with the position and color of 3,4-dihydroxyphenyl lactic acid and protocatechuic aldehyde; and (c) determining if pharmaceutical compositions contain the fractions of which position and color are equivalent to the position and the color of 3,4-dihydroxyphenyl lactic acid and protocatechuic aldehyde.

Finally, the present invention provides a method of determining if pharmaceutical compositions capable of treating and preventing cardiovascular diseases, herein said method comprising the steps of (a) treating heart muscles with or without pharmaceutical compositions; (b) comparing the rate of calcium influx in heart muscles treated without and with pharmaceutical compositions; and (c) determining if pharmaceutical compositions reduced the calcium influx to hear muscles.

This invention discloses a composition of the medicament Dan Shen Pill (DSP) comprising:
(a) water-soluble extracts of Radix Salviae Miltorrhizae, water-soluble extracts of Panax Notoginseng, and synthetic Borneol;
(b) Radix Salviae Miltorrhizae, Notoginseng, borneol, and carriers; and
(c) Radix Salviae Miltorrhizae, Panax Notoginseng, borneol, and pharmaceutical carriers.

In an embodiment of the above medicament, Radix Salviae Miltorrhizae and Panax Notoginseng are employed as they are used in China for treating coronary heart disease since 200 AD. Panax Notoginseng has been used to treat angina and Radix Salviae Miltorrhizae has been used to promote blood circulation. Borneol is employed to facilitate the fast delivery of therapeutic components to target organs. Natunal Borneol has been used in China since 600 AD. As Borneol is almost extinct, DSP comprises synthetic borneol.

This invention provides the use of DSP for:
(a) treating coronary heart disease;
(b) treating coronary heart disease in conjunction with other drugs;
(c) primary prevention of coronary heart disease;
(d) primary prevention of coronary heart disease in conjunction with other drugs;
(e) secondary prevention of coronary heart disease;
(f) secondary prevention of coronary heart disease in conjunction with other drugs; and
(g) reducing nitrates intake by angina patients; and
(h) reducing serum cholesterol level.

In an embodiment of DSP, the indication is for coronary artherosclerotic disease such as, but not limited, to alleviate angina pectoris, to prevent angina pectoris caused by exertion and stress, and to promote blood circulation by inhibiting platelet aggregation thus to preventing coronary thrombus formation. DSP can be applied to reduce nitroglycerine intake which is frequently used to alleviate and to prevent angina. DSP can be also applied to reduce plasma cholesterol level thus to prevent the formation of new atherosclerosis lesions. Atherosclerosis is often initiated by cholesterol streak deposited on vessel walls.

This inventions discloses a method for controlling the quality of medicaments by standarizing the composition and the concentration of therapeutic substances in a medicament by analyzing and identifying therapeutic components using analytical techniques comprising the steps of:
(a) fractionating a medicament using analytical techniques; and
(b) identifying and quantitating therapeutic substances contained in a medicament by comparing with the analytical profile of the relevant purified substances as standard.

In an embodiment of the above invention, examples of analytical techniques are thin-layer chromatography, high performance liquid chromatography, and others. The purified standard of therapeutic components are the major identified active components in medicaments. For example, the purified standards of active components for DSP are, but not limited to, saponins, phenolic acid such as Danshensu, borneol, etc. Active components in DSP are identified by comparing the position of DSP fractions such as retention time in high performance liquid chromatography or the position and the color of DSP fractions in thin-layer chromatography, etc. with the characteristic of purified standards. Active components of DSP is quantitated by comparing the size of active fractions of DSP with the size of the known amount of standards. For example, the amount of saponin contained in DSP is determined by comparing with the standard curve of the known amount of purified saponin.

In another embodiment, DSP comprises 5-40% water-soluble phenolic acid of Radix Salviae Miltorrhizae, 1-10% water soluble saponin of Panax Notoginseng, and 1-5% borneol.

In another embodiment, DSP comprises 10-30% water-soluble phenolic acid of Radix Salviae Miltorrhizae, 2-6% water soluble saponin of Panax Notoginseng, and 1-3% borneol.

This invention discloses a dropping machine for manufacturing a small-sized medicament, which can be readily dissolved thus readily delivered to organs, comprising the parts of:
(a) a dropping pot of which temperature ranges 60-100; more preferably 89-93° C.;
(b) liquid paraffin cooling solution of which temperature is lower than 8° C.;
(c) a dropping head with 1.8 mm inner diameter and 2.35 outer diameter;
(d) a dropping head distanced from the surface of cooling solution by approximately 15 m; and In an embodiment of the use of the above machine is to manufacture small-sized pills which can be dissolved immediately upon administration.

In another embodiment, the size of small pills are:
(a) 0.33-0.34 cm in diameter;
(b) 21.25-28.75 mg in weight; and
(c) 1.13-1.40 mg/mm$^3$ in density.

This invention provides a composition comprising extracts from the following herbal materials in weight proportion: Radix Salviae Miltorrhizae 48%~97%; Panax Notoginseng 2%~50%; and Borneol 0.2%~3%.

In an embodiment, the weight proportions are: Radix Salviae Miltorrhizae 63.0%~94%; Panax Notoginseng 4.0%~35.0%; and Borneol 0.5%~2.0%.

In another embodiment, the weight proportions are: Radix Salviae Miltorrhizae 75.2%~90%; Panax Notoginseng 9%~23.5%; and Borneol 0.5%~1.3%.

In a further embodiment, the weight proportions are: Radix Salviae Miltorrhizae 82.87%; Panax Notoginseng 16.21%; and Borneol 0.92%.

The extraction of these herbal materials has been exemplified below. Other extraction methods may be employed. The biological activity of the resulting composition containing the extracts can compare with the extracts described herein. Accordingly, it is the intention of this disclosure to include other enabling extraction technologies.

The present invention provides a pharmaceutical composition comprising the above composition and a pharmaceutically acceptable carrier.

For the purposes of this invention, "pharmaceutically acceptable carriers" means any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, etc. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

The present invention provides a pharmaceutical composition for treating coronary heart disease and angina pectoris comprising effective amount of extracts of Radix Salviae Miltorrhizae, Panax Notoginseng and Borneol. The present invention also provides the composition above wherein the Borneol is synthetic. The present invention further provides the composition above comprising effective amount of the composition from the above steps. In addition, the present invention provides a method for treating a subject with coronary heart disease comprising administering to the subject the pharmaceutical composition above and the method above wherein the subject is a human.

The invention provides a method for producing a composition of Radix Salviae Miltorrhizae, Panax Notoginseng and Borneol comprising steps of (a) obtaining appropriate amount of smashed Radix Salviae Miltorrhizae and Panax Notoginseng; (b) extracting the obtained Radix Salviae Miltorrhizae, Panax Notoginseng in hot aqueous reflux; (c) combining the extracts to form a combined extract; (d) concentrating the combined extract to perform alcohol precipitation to obtain a supernatant; (e) eliminating the alcohol of the supernatant to obtain a concentrated extract; (f) mixing the concentrated extract from step e with appropriate amount of borneol, thereby producing the composition of Radix Salviae Miltorizae, Panax Notoginseng and Borneol.

As used herein, the alcohol includes but is not limited to other alcohol appropriate for organic extraction. In a preferred embodiment, the alcohol is an ethanol.

The present invention also provides the method above wherein step b the temperature is between about 60 to about 100□. The present invention further provides the method above wherein step c, the extracts are filtered before combination.

In addition, the present invention provides the method above wherein step the ratio of the volume of the concentrated extract to the weight of inputting herbal materials being 1 liter: 0.7~1.3 kg. And the present invention provides the method above wherein step d the final concentration of ethanol is about 50-85%, wherein step d the final ethanol concentration is about 69-71%.

This invention provides the method above wherein step d the ethanol precipitation is performed for 4-24 hours, and wherein step d the ethanol precipitation for 8-12 hours. This invention also provides the method above, wherein the supernatant obtained in step d is filtered prior to the elimination of the alcohol. This invention further provides the method above wherein step e the concentrated extract is to form a plaster of about 1.15-1.45 in relative density. In addition, this invention provides the method above wherein step e the concentrated extract is to form a plaster of about 1.32-1.40 in relative density. And, this invention provides the method above wherein the borneol is synthetic.

This invention provides the method above further comprising packing the produced composition into the form of a powder, syrup, tea, tincture, injection, topical solution, capsule, pill, granule, tablet, nebula, suppository microcapsule or other pharmaceutically acceptable forms.

This invention also provides the method above wherein the formation of the pill comprising steps of (i) mixing the concentrated extract plaster from step e, borneol and other ingredients; (ii) heating to melt mixture and transfer it to a pill maker; (iii) pouring the melted mixture into paraffin oil at a low temperature; (iv) removing the paraffin oil; and (v) selecting the pills.

The present invention provides a method above wherein the other ingredient is a pharmaceutically acceptable carrier. The present invention also provides a method above wherein the other ingredient is Polyethylene glycol-6000 with a freezing point of about 53~58□. The present invention further provides a method above wherein the other ingredient is Polyethylene glycol-6000 and the amount added is 2-6 times in weight of the concentrated extract and borneol. In addition, the present invention provides a method above wherein the Polyethylene glycol-6000 added is 3 times in weight of the concentrated extract and borneol.

This invention provides a method above wherein the temperature for melting the mixture is about 60-100□. This invention also provides a method above wherein the temperature for melting the mixture is about 85-90□. This invention further provides a method above wherein the temperature of paraffin oil is about 0-10□. In addition, this invention provides a method above wherein the temperature of paraffin oil is about 5-10□. And, this invention provides a method above wherein the temperature of paraffin oil is about 7-8 □.

This invention provides a method above wherein the weight of the pills are measured in about 5-50 mg/pill and 1.95-4.29 mm in diameter. This invention also provides a method above wherein the weight of the pills are measured in 25±15% mg/pill and 3.34±15% mm in diameter.

The present invention provides the composition produced by steps of method above. The present invention also provides a pharmaceutical composition comprising the composition above and a pharmaceutically acceptable carrier. The present invention further provides the pharmaceutical composition above wherein the Borneol is synthetic. In addition, the present invention provides the pharmaceutical composition above for treating coronary heart disease. And, the present invention provides the pharmaceutical composition above for treating angina pectoris.

The present invention provides a method for increasing blood volume in coronary artery, relaxing the smooth muscles of blood vessels, improving the peripheral circulation, raising the oxygen content in veins, or significantly improving the acute myocardial ischemia or myocardial infarction in a subject comprising administering to the subject an effective amount of the composition above.

The present invention also provides a method for protecting the cells from damage by hypoxia, anoxia, deoxygenation or re-oxygenation by contacting said cells with effective amount of the composition above.

The present invention further provides a method for protecting the cells from damage by hypoxia, anoxia, deoxygenation or re-oxygenation in a subject comprising administering to the subject an effective amount of the composition above.

This invention provides a method for protecting cells suffering from myocardial ischemia by contacting said cells with effective amount of the composition above. This invention also provides a method for protecting cells suffering from myocardial ischemia in a subject comprising administering to the subject an effective amount of the composition above. This invention further provides a method for improving micro-circulation in a subject comprising administering to the subject an effective amount of the composition above. In addition, this invention provides a method for preventing arrhythmia in a subject comprising administering to the subject an effective amount of the composition above.

This invention provides a method for preventing platelets aggregation, thrombosis and dissolve fibrin in a subject comprising administering to the subject an effective amount of the composition above. This invention also provides a method for lowering blood viscosity, adjusting the blood cholesterol or preventing atherosclerosis in a subject comprising administering to the subject an effective amount of the composition above. This invention further provides a method for raising the tolerance to hypoxia, anoxia, preventing the oxidation of lipoprotein or removing the harmful free radicals in a subject comprising administering to the subject an effective amount of the composition above. In addition, this invention provides a method for lowering plasma ET content, significantly improve the liver, kidneys and pancreas functions in a subject comprising administering to the subject an effective amount of the composition above.

This invention provides a method for preventing the occurrence or development of blood vessel or nerve diseases in a subject comprising administering to the subject an effective amount of the composition above. This invention also provides a method for enhancing the immune system in a subject comprising administering to the subject an effective amount of the composition above. This invention further provides a method for regulating the vascular nervous balance in a subject comprising administering to the subject an effective amount of the composition above. In addition, this invention provides a method for preventing and treatment cardiovascular and cerebrovascular diseases, kidney disease, liver disease, pneumonia, lung or heart disease, pancreatitis, diabetes, vertebral disease, optic vessels disease, optic nerves disease, eccentric headache, chronic stomachitis, dizziness, bone diseases, altitude diseases, common elderly diseases in a subject comprising administering to the subject an effective amount of the composition above.

This invention provides a method for treating stable angina pectoris, unstable angina pectoris, aged angina pectoris, non-symptomatic myocardial ischemia, different types of coronary heart diseases or angina pectoris diseases in a subject comprising administering to the subject an effective amount of the composition above. This invention also provides a method for treating arrhythmia, enlargement of left ventricle, myocarditis, myocardial infarction or cerebral infraction in a subject comprising administering to the subject an effective amount of the composition above. This invention further provides a method for rapidly relieving coronary heart disease or angina pectoris in 3-10 minutes when it is taken sublingually in a subject comprising administering to the subject an effective amount of the composition above. In addition, this invention provides a method for treating hyperlipidaemia, high blood viscosity syndrome or high blood pressure in a subject comprising administering to the subject an effective amount of the composition above.

This invention provides a method for treating coronary heart disease and high blood pressure, coronary heart disease and hyperlipidaemia, coronary heart disease, enlargement of left ventricles and coronary heart disease or arrhythmia in a subject comprising administering to the subject an effective amount of the composition above. This invention also provides a method for treating diseases caused by micro-circulation disorder in a subject comprising administering to the subject an effective amount of the composition above. This invention further provides a method for treating stroke, cerebral infarction, cerebral bleeding and other cerebral diseases in a subject comprising administering to the subject an effective amount of the composition above. In addition, this invention provides a method for treating hepatitis B, chronic liver fibrosis, liver fibrosis, active liver cirrosis, liver cirrosis in compensation period and other related diseases in a subject comprising administering to the subject an effective amount of the composition above.

This invention provides a method for treating kidney syndrome and its conjunctive diseases in a subject comprising administering to the subject an effective amount of the composition above. This invention also provides a method for treating diabetes or its conjunctive diseases in a subject comprising administering to the subject an effective amount of the composition above. This invention also provides a method for treating cyanosis-typed optic vessels diseases such as venal blockage in retina, central optic artery blockage in retina, high blood pressure optic atherosclerosis in retina, diabetic retinopathy, cento-neuropathy, cento-osmotic neuropathy, ischemic neuropathy, optic neuritis or optic nervous dystrophy in a subject comprising administering to the subject an effective amount of the composition above. This invention further provides a method for treating dizziness caused by cerebral-arterial ischemia, Meniere's disease, high blood pressure, coronary heart disease in a subject comprising administering to the subject an effective amount of the composition above. In addition, this invention provides a method for enhancing the immune system in a subject comprising administering to the subject an effective amount of the composition above.

This invention provides a method for regulating the vascular nervous balance in a subject comprising administering to the subject an effective amount of the composition above. This invention also provides a method for treating detrimental death of epicondylus medialis, femoral end necrosis, twisted joint, ligament damage, fracture and proliferation of bone cells in a subject comprising administering to the subject an effective amount of the composition above. This invention further provides a method for treating bronchitis in children in a subject comprising administering to the subject an effective amount of the composition above. In addition, this invention provides a method for treating hypoxia or anoxia in a subject comprising administering to the subject an effective amount of the composition above. And finally, this invention provides a method for treating Alzhemier's Disease in a subject comprising administering to the subject an effective amount of the composition above.

Experimental Details
First Series of Experiments
Manufacturing of Dan Shen Pill (DSP)

DSP is a small pill, approximately 25 mg, of which therapeutic components comprise water-soluble extracts of Notoginseng, water soluble extracts of Salviae, and synthetic borneol.

For manufacturing DSP, Notoginseng and Salviae are extracted separately with hot water in circulating systems and filtered. The filtrates are condensed under decompressed conditions, filtered and precipitated. The concentrates are refined using resin columns and concentrated under decompressed conditions. The refined water-soluble extracts thus obtained were mixed with synthetic Borneol and pharmaceutical carriers. The mixture is made to a small pill using a special dropping machine. The quality of DSP is controlled by standarizing the quantity as well as the proportion of its major therapeutic components Saponon, phenolic acid such as Danshensu and Borneol. Thin-layer chromatography, high performance liquid chromatography, fingerprinting and other analytical techniques are used to identify and quantitate therapeutic components in DSP.

Manufacturing of DSP

1. Extraction of water-soluble components of Panax Notoginseng
   (a) Dilution of herbs with 5-7 times of water.
   (b) Extraction of water-soluble components of Panax Notoginseng by boiling in a tank with the air pressure between 0.04-0.06 mPa for 2 hours.
   (c) Repeat extraction under the same condition for 1.5 hours.
   (d) Filtration of the extraction with 100-mesh net.
   (e) Refine the filtrate using macroporous adsorption resin eluting with ethanol.
   (g) Concentration of the eluted extracts under decompressed condition with the air input to 0.04-0.06 mPa and the vacuum to −0.076~−0.088 mPa until the density is 1.33-1.35.

2. Extraction of water-soluble components of Radix Salviae Miltorrhizae
   (a) Dilution of herbs with 5-7 times of water.
   (b) Extraction of water-soluble components of Radix Salviae Miltorrhizae by boiling in a tank with the air pressure between 0.04-0.06 mPa for 2 hours.
   (c) Repeat extraction under the same condition for 1.5 hours.
   (d) Filtration of the extraction with 100-mesh net.
   (e) Concentration of the filtrates under decompressed conditions with the vacuum pressure is −0.076~−0.088 mPa until one Kg initial herb becomes one liter.
   (f) Precipitation of the concentrates with ethanol.
   (g) Filtration of the ethanol precipitates solution through 100-mesh net.
   (h) Concentration of the filtrates under decompressed conditions with input air pressure is 0.04-0.06 mPa and the vacuum pressure is 0.076~−0.088 mPa.
   (i) Refine the concentrates by polyamide chromatography eluting with ethanol.
   (j) Concentrate the refined extracts to the density of 1.33-1.35.

3. DSP production
   (a) Mix the extracts of Panax Notoginseng, the extracts of Radix Salviae Miltorrhizae, synthetic boneol and polyethylene glycol 6000 at the ratio of 4.0:20.6:1.9:79.5.
   (b) Melting the mixture.
   (c) Manufacturing the melted mixture to DSP using the dropping machine with the following characteristics: the temperature of dropping pot is constantly 89-93° C., the cooling solution is liquid paraffin of which the temperature is lower than 8° C., the inner diameter of the dropping head is 1.8 mm, the outer diameter of the dropping head is 2.4 mm, the distance between the dropping head and the surface of cooling solution is 15 cm.
   (d) Centrifugation of the pills at 800-1100 rpm for 15 minutes to remove oils.

Quality Control of DSP

DSP contains the identified therapeutic components protocatechuic aldehyde and saponin as well as various other components. The contents of these compounds in herbs vary from lot to lot of herbs. To standarize the contents of therapeutic components in DSP and thus to control the quality of DSP, a method to identify and to quantitate therapeutic agents in medicaments has been developed. An example of the procedures comprises:

(a) Dissolve 30 DSPs in 3 ml methanol and ultrasonicate for 10 minutes.
(b) Centrifugation for 5 minutes.
(c) Fractionate the supernatant using standard analytical techniques using thin layer chromatography, high performance liquid chromatography, etc.
(d) Identification of the therapeutic components of DSP such as Sodium Danshensu, protocatechuic aldehyde, saponin, etc. by comparing DSP fractions with the relevant purified standards in regard to the position, size and color.
(e) Identifying and quantitating therapeutic components in DSP by comparing the position, size, and color of DSP fractions with the position, size and color of the relevant purified standards.
(f) Identifying therapeutic components in DSP by comparing the relative retention time and relative area of peaks in fingerprints with the relative retention time and relative area of peaks in standard fingerprint.

TLC Identification of DSP

A method for identifying Sodium Danshensu and protocatechuic aldehyde of a herbal composition capable of treating chronic stable angina pectoris by thin layer chromatography comprising the steps of:

a) preparing the assay comprising the steps of:
   i. putting 30 pellets of the said composition in 3 ml methanol and dissolve by ultrasonation for 10 minutes to form a solution;
   ii. centrifuging the solution for 5 minutes and collect the supernatant;
   iii. contacting 10 ul the solution onto a silicon G gel plate containing 0.5% CMC-Na;
   iv. developing the plate with a developing solution comsisting of Chloroform, acetone and methane acid in the ratio of 10:4:1.6;
   v. drying and fumigating the plate with ammonia and laying the plate up for 15 minutes;
   vi. checking the plate under ultraviolet light, the spot representing the said composition should be at the corresponding position of the standards and show the same color.
b). using Sodium Danshensu and protocatechuic aldehyde as the standards.

A method for identifying gypenoside of a herbal composition capable of treating chronic stable angina pectoris by thin layer chromatography comprising the steps of:

a) preparing the assay comprising the steps of:
  i. Put 30 pellets of the said composition in 5 ml ammonia solvent and dissolve by ultrasonation to form a solution;
  ii. Put the said solution into the macroporous adsorption resin column; the speed is 0.5/minute;
  iii. After washing the macroporous adsorption resin column with 20 ml distilled water, the macroporous adsorption resin column is eluted with 2 ml methanol solution;
  iv. collecting the eluant;
  v. contacting 10 ul said eluant onto a silicon G gel plate containing 0.5% CMC-Na;
  vi. developing the plate with 10 ml developing solution which is a lower layer clarificant of the solution of Chloroform, acetone and water in the ratio of 6:3:1 after 2 hours at 10°C;
  vii. After being dried and sprayed with 10% ethanol sulfate, the plate is baked at 105°C for several minutes;
  viii. Check the plate under normal light, the spot representing the said composition should be at the corresponding position of the standards and show the same color.

b). using total gypenoside, Saponin R1 and ginsenoside Rg1 as the standards.

Fingerprints of Cardiotonic Pill

1. Preparation of Fingerprints (1) Chromatographic System and System Suitability Alkyl silan-linking silico-18 was used as the stationary phase, and the mixture of A and B as mobile phase. A was methanol and B was the mixture of water—"N,N-dimethylformamide"—glacial acetic acid (100:45:4). The concentration of A changes from 5% to 30% when time of gradient elution elapses from 0 to 25 minutes. The detective wavelength was set at 281 nm. The number of theoretical plates of the column was not less than 2000 when calculated with the peak of Danshensu.

(2) Apparatus and Reagents
Chromatograph: HP 1100 Liquid Chromatograph
Detector: HP VWD-stile ultraviolet detector
Column: Alltech Company 5u, 250×4.6 mm, ODS column
Pre-column: Alltech Company, Alltima $C_{18}$ 5 u pre-column
Temperature of the column: 30° C.

(3) Preparation of the Control Sample
Salvianic acid B, Danshensu and protocatechuic aldehyde were dissolved respectively in methanol to produce three control solutions each ml containing 50 μg, 40 μg and 10 μg correspondingly.

(4) Preparation of the Test Sample
Put 10 pills of Cardiotonic Pill into a 25 ml measuring flask, add 20 ml of methanol, ultrasonicate for 20 minutes, allow to cool, dilute the solution to the scale-line with methanol, centrifugate and take the supernate as the test solution.

(5) Procedure
Accurately inject 10 μl each of the control solutions and the test solution, respectively, into the column, record the chromatograph chart and calculate the content.

2. Fingerprints of Different Batches of Cardiotonic Pill

Twenty batches of Cardiotonic Pill samples were tested with the above-described method, and statistical data is shown as Table 1, Table 2 and Table 3. These data revealed that Cardiotonic Pill had specific fingerprint of its own and the fingerprints contained eight common peaks, that is, these peaks should exist simultaneously in each batch of DSP. Taking protocatechuic aldehyde peak as reference peak, whose relative retention time was 1, the average value of relative retention time of the eight peaks was 0.672, 1.000, 1.417, 1.512, 2.016, 2.235, 2.407, 2.757. The values of relative retention time and relative area of the eight peaks were very stable, and among the eight common peaks, peak No. 1 was Danshensu, peak No. 2 protocatechuic aldehyde and peak No. 7 Salvianic acid B, and the ratio of relative area value was 0.476-0.668:1:0.391-0.641, respectively.

Figure 2:
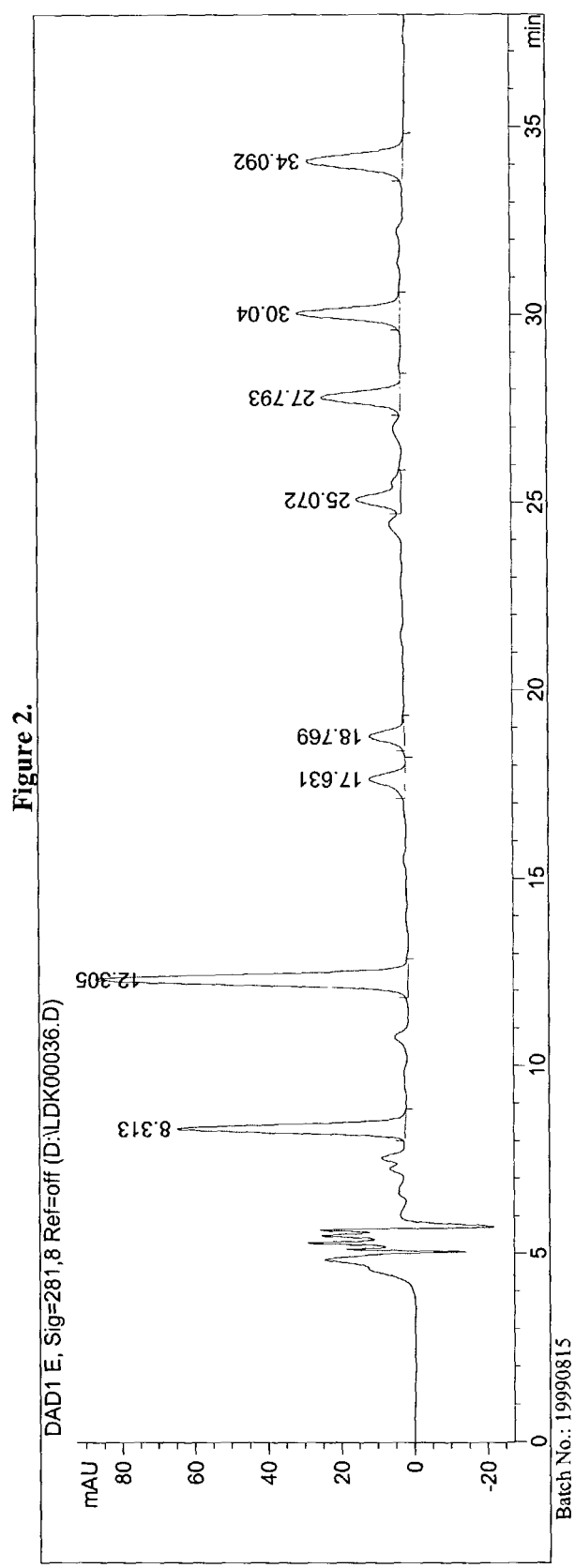
Figure 3:
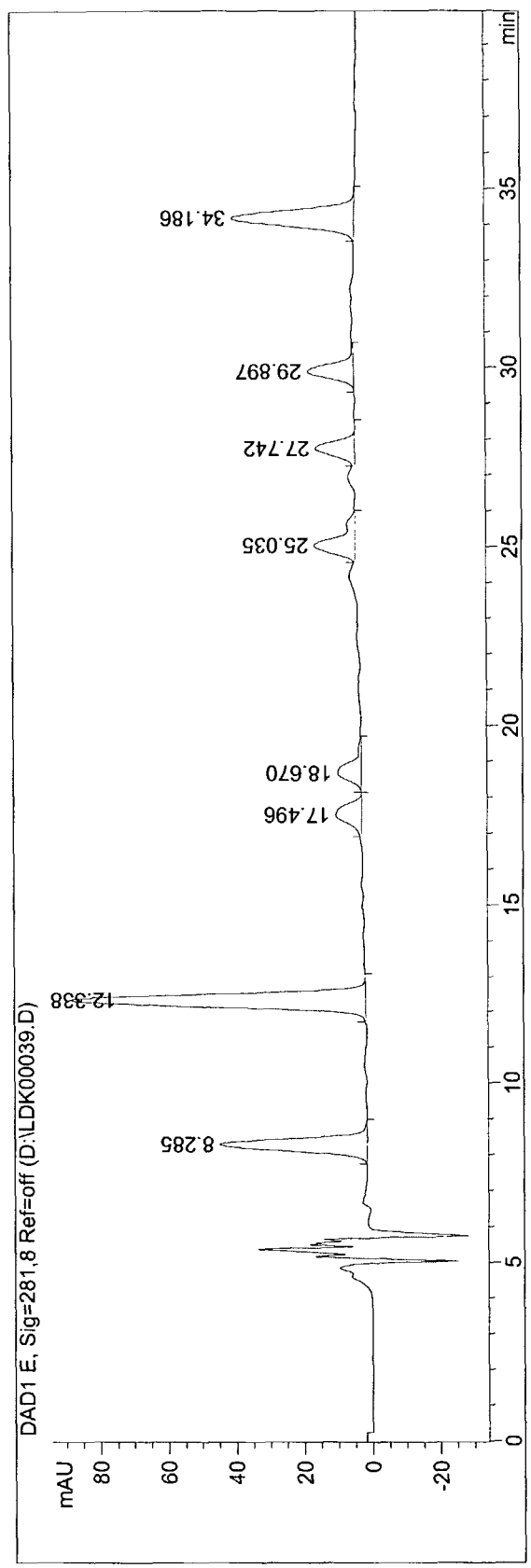

Fingerprints of three batches of Cardiotonic Pill are also provided as FIGS. 1 through 3.

TABLE 1

The peak retention time & relative retention time of 20 batches of DSP

| | Common Peaks | | | | | | | |
|---|---|---|---|---|---|---|---|---|
| | Peak No. 1 | | Peak No. 2 | | Peak No. 3 | | Peak No. 4 | |
| Batch No. | Retention time | Relative retention time | Retention time | Relative retention time | Retention time | Relative retention time | Retention time | Relative retention time |
| 19990806 | 8.347 | 0.676 | 12.341 | 1.000 | 17.662 | 1.431 | 18.802 | 1.524 |
| 19990815 | 8.313 | 0.676 | 12.305 | 1.000 | 17.631 | 1.433 | 18.769 | 1.525 |
| 19990823 | 8.285 | 0.672 | 12.338 | 1.000 | 17.498 | 1.418 | 18.673 | 1.513 |
| 19990921 | 8.302 | 0.672 | 12.350 | 1.000 | 17.553 | 1.421 | 18.739 | 1.517 |
| 19990928 | 8.299 | 0.672 | 12.352 | 1.000 | 17.549 | 1.421 | 18.727 | 1.516 |
| 19991014 | 8.290 | 0.672 | 12.344 | 1.000 | 17.496 | 1.417 | 18.677 | 1.513 |
| 19991026 | 8.295 | 0.672 | 12.337 | 1.000 | 17.513 | 1.420 | 18.673 | 1.514 |
| 19991109 | 8.286 | 0.672 | 12.329 | 1.000 | 17.477 | 1.418 | 18.642 | 1.512 |
| 19991127 | 8.291 | 0.672 | 12.341 | 1.000 | 17.502 | 1.418 | 18.660 | 1.512 |
| 19991205 | 8.291 | 0.672 | 12.340 | 1.000 | 17.500 | 1.418 | 18.659 | 1.512 |
| 20000106 | 8.287 | 0.672 | 12.338 | 1.000 | 17.503 | 1.419 | 18.664 | 1.513 |
| 20000216 | 8.294 | 0.671 | 12.352 | 1.000 | 17.536 | 1.420 | 18.687 | 1.513 |
| 20000323 | 8.256 | 0.670 | 12.329 | 1.000 | 17.402 | 1.411 | 18.606 | 1.509 |
| 20000406 | 8.272 | 0.670 | 12.349 | 1.000 | 17.428 | 1.411 | 18.628 | 1.508 |
| 20000422 | 8.274 | 0.670 | 12.348 | 1.000 | 17.425 | 1.411 | 18.609 | 1.507 |
| 20000513 | 8.276 | 0.670 | 12.350 | 1.000 | 17.439 | 1.412 | 18.611 | 1.507 |
| 20000606 | 8.273 | 0.670 | 12.347 | 1.000 | 17.421 | 1.411 | 18.597 | 1.506 |
| 20000726 | 8.283 | 0.670 | 12.356 | 1.000 | 17.413 | 1.409 | 18.598 | 1.505 |
| 20000728 | 8.287 | 0.670 | 12.368 | 1.000 | 17.487 | 1.414 | 18.653 | 1.508 |
| 20000804 | 8.274 | 0.670 | 12.351 | 1.000 | 17.434 | 1.412 | 18.597 | 1.506 |

TABLE 1-continued

The peak retention time & relative retention time of 20 batches of DSP

| | | | | | | | | |
|---|---|---|---|---|---|---|---|---|
| Average value | 8.289 | 0.672 | 12.343 | 1.000 | 17.493 | 1.417 | 18.664 | 1.512 |
| RSD % | 0.225 | 0.266 | 0.104 | 0.000 | 0.398 | 0.447 | 0.313 | 0.362 |

Common Peaks

| | Peak No. 5 | | Peak No. 6 | | Peak No. 7 | | Peak No. 8 | |
|---|---|---|---|---|---|---|---|---|
| Batch No. | Retention time | Relative retention time | Retention time | Relative retention time | Retention time | Relative retention time | Retention time | Relative retention time |
| 19990806 | 25.090 | 2.033 | 27.805 | 2.253 | 30.047 | 2.435 | 34.146 | 2.767 |
| 19990815 | 25.072 | 2.038 | 27.793 | 2.259 | 30.046 | 2.442 | 34.092 | 2.771 |
| 19990823 | 25.034 | 2.029 | 27.742 | 2.249 | 29.897 | 2.423 | 34.186 | 2.771 |
| 19990921 | 25.005 | 2.025 | 27.715 | 2.244 | 29.875 | 2.419 | 34.155 | 2.766 |
| 19990928 | 24.968 | 2.021 | 27.661 | 2.239 | 29.804 | 2.413 | 34.070 | 2.758 |
| 19991014 | 24.903 | 2.017 | 27.604 | 2.236 | 29.743 | 2.410 | 34.019 | 2.756 |
| 19991026 | 24.889 | 2.017 | 27.600 | 2.237 | 29.747 | 2.411 | 34.017 | 2.757 |
| 19991109 | 24.852 | 2.016 | 27.571 | 2.236 | 29.722 | 2.411 | 34.014 | 2.759 |
| 19991127 | 24.882 | 2.016 | 27.594 | 2.236 | 29.737 | 2.410 | 34.026 | 2.757 |
| 19991205 | 24.862 | 2.015 | 27.569 | 2.234 | 29.708 | 2.407 | 34.007 | 2.756 |
| 20000106 | 24.867 | 2.015 | 27.576 | 2.235 | 29.721 | 2.409 | 34.026 | 2.758 |
| 20000216 | 24.887 | 2.015 | 27.590 | 2.234 | 29.730 | 2.407 | 34.066 | 2.758 |
| 20000323 | 24.869 | 2.017 | 27.561 | 2.235 | 29.644 | 2.404 | 34.067 | 2.763 |
| 20000406 | 24.843 | 2.012 | 27.534 | 2.230 | 29.613 | 2.398 | 34.012 | 2.754 |
| 20000422 | 24.799 | 2.008 | 27.493 | 2.227 | 29.572 | 2.395 | 33.975 | 2.751 |
| 20000513 | 24.791 | 2.007 | 27.479 | 2.225 | 29.553 | 2.393 | 33.944 | 2.749 |
| 20000606 | 24.755 | 2.005 | 27.451 | 2.223 | 29.524 | 2.391 | 33.918 | 2.747 |
| 20000726 | 24.744 | 2.003 | 27.440 | 2.221 | 29.513 | 2.389 | 33.925 | 2.746 |
| 20000728 | 24.807 | 2.006 | 27.500 | 2.223 | 29.573 | 2.391 | 34.001 | 2.749 |
| 20000804 | 24.746 | 2.004 | 27.441 | 2.222 | 29.515 | 2.390 | 33.941 | 2.748 |
| Average value | 24.883 | 2.016 | 27.586 | 2.235 | 29.714 | 2.407 | 34.030 | 2.757 |
| RSD % | 0.416 | 0.476 | 0.399 | 0.463 | 0.540 | 0.606 | 0.219 | 0.273 |

TABLE 2

The peak area value & area ratio of 20 batches of DSP

| | Common Peaks | | | | | | | |
|---|---|---|---|---|---|---|---|---|
| | Peak No. 1 | | Peak No. 2 | | Peak No. 3 | | Peak No. 4 | |
| Batch No. | Area | Area ratio | Area | Area ratio | Area | Area ratio | Area | Area ratio |
| 19990806 | 1044.800 | 0.668 | 1563.800 | 1.000 | 269.790 | 0.173 | 240.540 | 0.154 |
| 19990815 | 834.300 | 0.576 | 1448.900 | 1.000 | 359.860 | 0.248 | 347.080 | 0.240 |
| 19990823 | 1036.100 | 0.576 | 1800.300 | 1.000 | 409.060 | 0.227 | 334.160 | 0.186 |
| 19990921 | 980.840 | 0.568 | 1726.000 | 1.000 | 379.050 | 0.220 | 317.920 | 0.184 |
| 19990928 | 1068.000 | 0.549 | 1943.800 | 1.000 | 397.230 | 0.204 | 329.450 | 0.169 |
| 19991014 | 984.660 | 0.589 | 1670.700 | 1.000 | 353.250 | 0.211 | 297.610 | 0.178 |
| 19991026 | 978.100 | 0.556 | 1758.900 | 1.000 | 348.520 | 0.198 | 282.550 | 0.161 |
| 19991109 | 974.320 | 0.603 | 1617.100 | 1.000 | 334.350 | 0.207 | 275.060 | 0.170 |
| 19991127 | 1053.800 | 0.565 | 1865.300 | 1.000 | 413.960 | 0.222 | 327.640 | 0.176 |
| 19991205 | 1089.600 | 0.564 | 1931.200 | 1.000 | 391.970 | 0.203 | 334.240 | 0.173 |
| 20000106 | 1130.800 | 0.571 | 1979.800 | 1.000 | 408.490 | 0.206 | 347.890 | 0.176 |
| 20000216 | 1114.900 | 0.548 | 2034.600 | 1.000 | 419.800 | 0.206 | 426.030 | 0.209 |
| 20000323 | 1080.000 | 0.599 | 1801.900 | 1.000 | 323.240 | 0.179 | 294.760 | 0.164 |
| 20000406 | 1132.600 | 0.583 | 1943.200 | 1.000 | 431.080 | 0.222 | 374.840 | 0.193 |
| 20000422 | 1124.400 | 0.508 | 2212.300 | 1.000 | 378.160 | 0.171 | 356.690 | 0.161 |
| 20000513 | 1088.200 | 0.564 | 1928.200 | 1.000 | 390.250 | 0.202 | 331.510 | 0.172 |
| 20000606 | 1033.200 | 0.575 | 1796.300 | 1.000 | 408.200 | 0.227 | 333.210 | 0.185 |
| 20000726 | 985.250 | 0.569 | 1730.200 | 1.000 | 382.510 | 0.221 | 322.210 | 0.186 |
| 20000728 | 1120.320 | 0.521 | 2148.500 | 1.000 | 410.920 | 0.191 | 385.540 | 0.179 |
| 20000804 | 831.320 | 0.577 | 1440.300 | 1.000 | 321.250 | 0.223 | 301.280 | 0.209 |
| Average value | 1034.276 | 0.572 | 1817.065 | 1.000 | 376.547 | 0.208 | 328.011 | 0.181 |
| RSD % | 8.486 | 5.612 | 11.452 | 0.000 | 10.914 | 9.354 | 12.553 | 11.003 |

TABLE 2-continued

The peak area value & area ratio of 20 batches of DSP

| | Common Peaks | | | | | | | |
|---|---|---|---|---|---|---|---|---|
| | Peak No. 5 | | Peak No. 6 | | Peak No. 7 | | Peak No. 8 | |
| Batch No. | Area | Area ratio | Area | Area ratio | Area | Area ratio | Area | Area ratio |
| 19990806 | 266.040 | 0.170 | 583.830 | 0.373 | 1001.800 | 0.641 | 1568.000 | 1.003 |
| 19990815 | 340.390 | 0.235 | 348.490 | 0.241 | 600.210 | 0.414 | 994.740 | 0.687 |
| 19990823 | 486.430 | 0.270 | 495.600 | 0.275 | 823.430 | 0.457 | 1632.800 | 0.907 |
| 19990921 | 498.570 | 0.289 | 479.530 | 0.278 | 875.440 | 0.507 | 1518.700 | 0.880 |
| 19990928 | 514.290 | 0.265 | 595.650 | 0.306 | 1092.700 | 0.562 | 1828.100 | 0.940 |
| 19991014 | 504.860 | 0.302 | 504.900 | 0.302 | 879.420 | 0.526 | 1378.000 | 0.825 |
| 19991026 | 451.380 | 0.257 | 416.600 | 0.237 | 800.660 | 0.455 | 1303.700 | 0.741 |
| 19991109 | 477.390 | 0.295 | 491.810 | 0.304 | 836.830 | 0.517 | 1302.800 | 0.806 |
| 19991127 | 499.750 | 0.268 | 521.160 | 0.279 | 1047.200 | 0.561 | 1643.800 | 0.881 |
| 19991205 | 468.210 | 0.242 | 521.600 | 0.270 | 890.080 | 0.461 | 1659.100 | 0.859 |
| 20000106 | 512.040 | 0.259 | 519.150 | 0.262 | 891.890 | 0.450 | 1747.000 | 0.882 |
| 20000216 | 570.720 | 0.281 | 521.100 | 0.256 | 1232.200 | 0.606 | 1767.500 | 0.869 |
| 20000323 | 562.520 | 0.312 | 602.060 | 0.334 | 1041.600 | 0.578 | 1544.700 | 0.857 |
| 20000406 | 609.180 | 0.313 | 655.030 | 0.337 | 1166.600 | 0.600 | 1642.400 | 0.845 |
| 20000422 | 574.650 | 0.260 | 692.970 | 0.313 | 1189.700 | 0.538 | 1758.300 | 0.795 |
| 20000513 | 466.050 | 0.242 | 518.200 | 0.269 | 886.300 | 0.460 | 1750.200 | 0.908 |
| 20000606 | 485.200 | 0.270 | 492.920 | 0.274 | 821.520 | 0.457 | 1613.200 | 0.898 |
| 20000726 | 502.350 | 0.290 | 483.060 | 0.279 | 880.210 | 0.509 | 1523.200 | 0.880 |
| 20000728 | 621.250 | 0.289 | 672.250 | 0.313 | 1178.200 | 0.548 | 1692.300 | 0.788 |
| 20000804 | 321.240 | 0.223 | 392.720 | 0.273 | 683.270 | 0.474 | 1081.360 | 0.751 |
| Average value | 486.626 | 0.267 | 525.432 | 0.289 | 940.963 | 0.516 | 1547.495 | 0.850 |
| RSD % | 18.592 | 12.698 | 16.851 | 11.766 | 18.292 | 12.061 | 14.739 | 8.647 |

TABLE 3

The statistical data of eight peaks derived from fingerprints of 20 batches of DSP

| Peak No. | Retention Time | Relative Retention Time | Appearance Probability | Area | Area Ratio | Area Ratio Range |
|---|---|---|---|---|---|---|
| 1 | 8.289 | 0.672 | 100% | 1034.276 | 0.572 | 0.572 ± 0.096 |
| 2 | 12.343 | 1.000 | 100% | 1817.065 | 1.000 | 1.000 ± 0.000 |
| 3 | 17.493 | 1.417 | 100% | 376.547 | 0.208 | 0.208 ± 0.040 |
| 4 | 18.664 | 1.512 | 100% | 328.011 | 0.181 | 0.181 ± 0.059 |
| 5 | 24.883 | 2.016 | 100% | 486.626 | 0.267 | 0.267 ± 0.097 |
| 6 | 27.586 | 2.235 | 100% | 525.432 | 0.289 | 0.289 ± 0.052 |
| 7 | 29.714 | 2.407 | 100% | 940.963 | 0.516 | 0.516 ± 0.125 |
| 8 | 34.030 | 2.757 | 100% | 1547.495 | 0.850 | 0.850 ± 0.163 |

Quantitative Analysis of Danshensu in DSP

Chromatography and systemic adaptive conditions, apparatus and reagents:

1. Preparation of Fingerprints (1) The Parameters of Chromatogram & System Adjustment.

Alkyl silan-linking silico-18 was used as filling material, and water-acetonitrile-glacial acetic acid (87:12:1) as mobile phase. Detective wave length was set at 281 nm. The number of theoretical plate should not be less than 2500 when calculated with the peak of Danshensu, and the degree of separation should meet the requirements.

(2) Apparatus & Reagents

Chromatograph: HP 1100 Liquid Chromatograph

Detector: HP VWD-stile ultraviolet detector

Column: Alltech Company 5u, 250×4.6 mm, ODS column

Pre-column: Alltech Company, Alltima C18 5 u pre-column

Temperature of the column: 30° C.

Acetonitrile: chromatographically pure, Tianjin Siyou Biomedical & Technical Co. Ltd.

Glacial acetic acid: analytically pure, Tianjin Tianhe Reagent Company.

(3) Preparation of the Control Sample.

Use 25.0 mg of sodium salvianic acid and 5.0 mg of protocatechuic aldehyde as the control samples: Weigh both of the samples accurately and put them into the 50 ml measuring flasks. Add mobile phase to dissolve them and dilute the solutions up to the scale-line of the flasks, shake them thoroughly and save them as the stock solutions. Weigh a little amount of paraaminobenzoic acid accurately, dissolve it as a solution of 0.2 mg/ml with the mobile phase and take it as the internal standard stock solution. Pipit proper amounts of sodium salvianic acid A, protocatechuic aldehyde and internal standard solutions whit their volumes accurately read, dilute them with the mobile phase to prepare a solution that contained 50 ug of sodium salvianic acid A, 10 ug of protocatechuic aldehyde and 80 ug of paraaminobenzoic acid. The prepared solution was taken as the control solution.

(4) Preparation of the Test Sample.

Take 10 pills of Cardiotonic Pill and 1 ml of internal standard stock solution, put them into a 25 ml measuring flask, dissolve them with mobile phase, and dilute the solution to the scale-line. Take 10 ml of the control and the test sample solutions, respectively, make the injection and record the chromatograph chart.

Preparation of the control solution: Take and weigh accurately 25.0 mg of sodium tanshinol, and put it into a measuring flask. Add the mobile phase, and dissolve and dilute it to the scale. Shake the solution up, and keep it as the control stock solution. Weigh para-aminobenzoic acid accurately and dilute it into a 0.2 mg/ml solution with the mobile phase. Keep the solution as the internal standard stock solution. Take appropriate doses of the control stock solution and the internal standard stock solution, and make them into the control solution comprising 50 μg of sodium tanshinol and 80 μg of para-aminobenzoic acid per milliliter.

Preparation of the test solution: Take 10 pills of this article and 1 ml of the internal stock solution. Put them in a 25 ml measuring flask, dissolve them to the scale and make them into the test solution.

Take 10l of the control solution and 10l of the test solution respectively, take down the fingerprints and calculate the results.

The herbal composition comprising DSP should contains 0.14-0.18 mg Danshensu per pill.

Quantitative Analysis of Ginsenoside Rg1 and Sanchinoside R1 in DSP (1) Chromatographic System and System Suitability Alkyl silan-linking silico-18 was used as the stationary phase, and the mixture of water and acetonitrile as mobile phase. The concentration of acetonitrile was 25% from 0 to 15 minutes, and 35% after 15th minute. Nebulizer gas flowrate was 2.5 liter per minute and drift tube temperature was set at 93.8° C. The number of theoretical plates of the column was not less than 5000 when calculated with the peak of Ginsenoside Rg1.

(2) Apparatus and Reagents

Chromatograph: Agilent 1100 Liquid Chromatograph
Detector: Alltech ELSD 2000 detector (evaporative light scattering detector)
Column: Alltech Company 5u, 250×4.6 mm, ODS-$C_{18}$ column
Pre-column: Alltech Company, Alltima $C_{18}$ 5 u pre-column
Temperature of the column: 30° C.

(3) Preparation of the Control Sample

Ginsenoside Rg1 and Sanchinoside R1 were dissolved respectively in methanol to produce two control solutions each ml containing 0.98 mg and 0.25 mg correspondingly.

(4) Preparation of the Test Sample

Put 50 pills of Cardiotonic Pill into a 5 ml measuring flask, add 4% ammonia to the scale-line, ultrasonicate for 20 minutes, and apply the solution to a previously prepared small $C_{18}$ column (STRATA C18-E column of Phenomenex Company, 500 mg and 3 cc tube), elute 10 ml of water, discard the eluate, then elute 2 ml of methanol, collect the eluate in a measuring flask and dilute it to the scale-line with methanol, take the solution as the test solution.

(5) Procedure

Accurately inject 10 μl each of the control solutions and the test solution, respectively, into the column, record the chromatograph chart and calculate the content.

(6) Result

Twenty batches of Cardiotonic Pill samples were tested with the above-described method, and statistical data is shown as Table 4. Drawn on above table, the herbal composition comprising DSP contains 0.401%~712%, average 0.550% Sanchinoside R1 and 2.069%-4.44%, average 2.847% Ginsenoside Rg1.

TABLE 4

Quantities of Ginsenoside Rg1 and Sanchinoside R1 in DSP

| Batch No. | Sanchinoside R1 (μg/pill) | Ginsenoside Rg1 (μg/pill) |
|---|---|---|
| 20000106 | 17.22 | 80.93 |
| 20000216 | 16.92 | 80.78 |
| 20000323 | 15.16 | 70.76 |
| 20000406 | 13.65 | 62.51 |
| 20000422 | 14.24 | 68.72 |
| 20000513 | 15.27 | 71.16 |
| 20000606 | 14.86 | 68.21 |
| 20000726 | 14.59 | 72.35 |
| 20000728 | 14.25 | 57.37 |
| 20000804 | 15.30 | 70.55 |
| Average value | 15.15 | 70.33 |
| RSD % | 7.53 | 9.67 |
| not less than | 12.12 | 56.26 |

The characteristics of DSP thus manufactured are as follows:
(a) DSP contain b-3,4-dihydroxyphenyl lactic acid, sodium danshensu, saponin, and borneol,
(b) negative for bacteria: contains less than 1,000 bacteria,
(c) negative for fungi: contains less than 100 fungi,
(d) negative for heavy metal: contains less than the safety amount defined by the Chinese government.
(e) The shelf-life of DSP is four years at room temperature.

Clinical Studies of DSP

Angina pectoris is evaluated by the history of angina, serum lipid level, electrocardiography (ECG), exercise ECG, scintiographic assessment of ischemia, coronary angiography, etc. Assessing therapeutic efficacy using these end points, DSP has been shown to be effective for treating angina pectoris.

DSP is Effective for Angina Pectoris.

157 patients with coronary heart disease were treated with 10 DSPs per t.i.d., oral administration for 4 weeks. Assessing the frequency, intensity and duration of angina, oppressed feeling in chest and palpitation, the symptoms were disappeared or remitted in 95.3% patients.

DSP is more Efficient than Dan Shen Tablets in Alleviating Angina.

Dan Shen tablet is another Chinese medicament for treating angina pectoris currently used in China. The efficacy of DSP and Dan Shen tablet was compared. Coronary heart disease patients were randomly divided into two groups. 107 patients were treated with DSP and 50 patients were treated with Dan Shen Tablet. Comparing the frequency of angina attacks and the consumption of nitrates, DSP was more effective than Dan Shen Tablets for treating angina pectoris. See Table 5 below.

TABLE 5

Comparison of DSP and Dan Shen tablet

| | Number of patients | |
|---|---|---|
| | Total | Responsive |
| DSP | 107 | 102 (95.3%) |
| Dan Shen tablet | 50 | 38 (76%) |

Having proven that DSP is more effective than Dan Shen tablets, the efficacy of DSP was compared with various drugs which are currently used for treating chronic stable angina pectoris in the US.

Comparison of DSP and Nitroglycerine

Nitroglycerine is the frequently used to relieve angina. The efficacy of DSP and nitroglycerine relieving angina was compared. At the onset of angina, patients were treated with either DSP or nitroglycerine, and the time required to alleviate angina was compared. Both DSP and nitroglycerine alleviate angina in all patients within 15 minutes. The efficacy of DSP was slightly lower than nitroglycerine. See Table 6 below.

TABLE 6

Comparison of DSP and nitroglycerine

| | # patients responded | | |
|---|---|---|---|
| | within 1-5 minutes | 6-10 minutes | 11-15 minutes |
| DSP | 11 | 14 | 5 |
| Nitroglycerine | 17 | 12 | 1 |

Total: 30 patients per group

DSP does not Change Heart Rate

The data demonstrate that DSP effectively alleviate angina. It was examined whether DSP relieves anginal by increasing heart rate. The heart rate after DSP treatment was equivalent to the pretreatment rate, which indicates that DSP relieves angina without affecting heart rate (Table 7).

TABLE 7

DSP does not affect heart rate

| | Heart rate | |
|---|---|---|
| | Pretreatment | Post-treatment |
| DSP | 84.3 ± 23.1 | 82.8 ± 22.8 |

Comparison of the Efficacy of DSP with the Nitrate Isosorbide Dinitrate

Having proven that DSP alleviate angina as efficiently as nitroglycerin, it was examined whether DSP can prevent angina. The efficacy of DSP and the nitrate isosorbide dinitrate was compared. Isosorbide dinitrate is a long-acting nitrate frequently used for preventing chronic stable angina pectoris in the US. Patients were treated with either DSP three times per day orally 10 pills per treatment or Isosorbide dinitrate three times per day orally 10 mg per treatment. Cardiac function and Electrocardiogram was examined.

Cardiac Function.

The efficacy of DSP and nitrates on cardiac function was evaluated by measuring cardiac output per stroke (CO), stroke volume per minute (SV), eject blood fraction (EF), fraction of shortened rate of left ventricular short axis (FS). DSP improves cardiac function more efficiently than nitrates. See Table 8 below.

TABLE 8

The effect of DSP and nitrates on cardiac function

| | DSP | | Isosorbide initrate | |
|---|---|---|---|---|
| | Pre- | Post- | Pre- | Post |
| SV | 75.38 ± 8.32 | 83.45 ± 9.11 | 74.96 ± 8.44 | 79.47 ± 8.72 |
| CO | 5.61 ± 1.34 | 6.94 ± 1.36 | 6.54 ± 1.36 | 6.12 ± 1.41 |

TABLE 8-continued

The effect of DSP and nitrates on cardiac function

| | DSP | | Isosorbide initrate | |
|---|---|---|---|---|
| | Pre- | Post- | Pre- | Post |
| EF | 0.57 ± 0.02 | 0.79 ± 0.02 | 0.59 ± 0.03 | 0.70 ± 0.03 |
| FS | 17.14 ± 3.4 | 16.69 ± 3.6 | 17.32 ± 3.1 | 18.46 ± 4.2 |

Pre-: preteatment
Post-: post-treatment

DSP Improves ECG

The ST-T effective rate was evaluated by recording the frequency of change in the ST-T segment. Both DSP and isosorbide dinitrates decreased the frequency of change in ST-T significantly. DSP, however, was more efficient. See Table 9 below.

TABLE 9

Comparison of the effect of DSP and nitrate on ECG

| | The frequency of ST-T change | |
|---|---|---|
| | Pretreatment | Post-treatment |
| DSP | 131 | 35 |
| isosorbide dinitrate | 129 | 42 |

Comparison of DSP and Aspirin in Reducing Blood Stasis

Hemorrhage at the atherosclerotic lesions induces platelet activation, coronary thrombosis and blood stasis resulting in impaired blood flow. Thus to improve blood flow, chronic administration of the platelet-activation inhibitor aspirin is recommended for patients with angina. The efficacy of DSP and aspirin improving blood flow was compared by evaluating [Hb, Lb, P and air flow]. DSP improves blood flow as efficiently as aspirin. DSP improves blood flow as efficiently as aspirin. See Table 10 below.

TABLE 10

DSP and aspirin improve blood flow

| | DSP | | aspirin | |
|---|---|---|---|---|
| | Pre- | Post- | Pre- | Post- |
| Hb | 6.23 ± 1.67 | 4.35 ± 1.02 | 6.12 ± 1.56 | 4.28 ± 1.07 |
| LB | 10.92 ± 2.21 | 8.30 ± 1.14 | 10.38 ± 1.96 | 8.21 ± 0.3 |
| P | 1.95 ± 0.08 | 1.77 ± 0.08 | 1.89 ± 0.12 | 1.67 ± 0.7 |
| Air flow | 1.79 ± 0.13 | 1.39 ± 0.11 | 1.82 ± 0.17 | 1.40 ± 0.10 |

Total number of patients: 25 for DSP and 28 for aspirin

DSP Reduces Blood Stasis by Inhibiting Platelet Activation

Thromboxane B2 activates platelet. Activated platelets release various substances including β platelet microglobulin, which causes blood stasis, thus impairing blood flow. The efficacy of DSP inhibiting platelet activation was examined. DSP lowers thromboxane B2 concentration and inhibits platelet aggregation efficiently. Isosorbide dinitrate, which is known to be unable to inhibit platelet activation thus used as control, did not reduce thromboxane B2 or inhibit platelet activation. See Table 11 below.

TABLE 11

DSP inhibits platelet activation

|  |  | Pretreatment | Post-treatment |
|---|---|---|---|
| β PM | DSP | 62.44 ± 14.37 | 45.65 ± 12.25 |
|  | nitrates | 59.89 ± 15.42 | 54.36 ± 13.18 |
| Txβ2 | DSP | 1312 ± 535 | 738 ± 384 |
|  | nitrates | 1315 ± 507 | 1218 ± 445 |

DSP Lowers Plasma Cholesterol Level

Increased plasma cholesterol has been implicated in the initiation of atherosclerosis. To prevent the formation of new atherosclerotic lesions, the decrease of plasma cholesterol either by modifying diets or drugs was recommended. It was examined whether DSP decreases plasma cholesterol. DSP lowered the cholesterol level by 0.3 mmol/L, which is statistically significant at the P value 0.05. See Table 12 below.

TABLE 12

DSP decreases plasma cholesterol

| | Plasma cholesterol (mmol/L) | |
|---|---|---|
| | Pretreatment | Posttreatment |
| DSP | 5.15 ± 0.16 | 4.84 ± 0.2 |

Number of patients: 80

Cardiotonic Pill's Effect on LPO and SOD in the Blood Serum of Patients Suffering from Coronary Heart Disease The method: In the treatment group, 24 patients, in accordance with China Reference Diagnosis Standards for Coronary Heart Disease amended in 1979, are administered with Cardiotonic Pill, 10 pills/time, and 3 times/day. In the normal group, 20 healthy people do not receive any medical treatment.

The results: The level of LPO of the patients suffering from coronary heart disease is clearly higher than that of the healthy people, while the content of SOD is clearly lower (p<0.01). After the patients are treated with Cardiotonic Pill, their LPO evidently decreases (p<0.01), and their SOD evidently increases (p<0.01). See Table 13 below.

TABLE 13

A Comparison of the Contents of SOD and LPO in the Normal and the Treatment Groups (x ± s)

| Groups | Patients |  | SOD (ng/ml) | LPO (nmol/ml) |
|---|---|---|---|---|
| Normal group | 20 |  | 348 ± 106 | 4.64 ± 1.52 |
| Treatment group | 24 | Before treatment | 267 ± 76* | 7.16 ± 1.48* |
|  |  | After treatment | 309 ± 87#. | 4.68 ± 1.72## |

Note:
In comparison with the normal group, *p < 0.05. In comparing with those of pre-treatment, #p < 0.05, ##p < 0.01.

The conclusion: Chronic ischemia of cardiac muscles of patients suffering from coronary heart disease and tissue anoxia lead to the reduction of the activity of SOD, especially that of extra cellular SOD, and the increase of oxygen free radicals, which causes the elevation of LPO and consumption of SOD further. After the patients are treated with Cardiotonic Pill, the level of LPO decreases evidently, while the content of the SOD increases obviously. This proves that Cardiotonic Pill has a strong action of clearance on oxygen free radicals, which is also one of the mechanisms to treat coronary heart disease.

The Effect of Cardiotonic Pill on the Activities of LPO and Antioxidases in Treatment of Pulmonary Heart Disease The method: The subjects: 48 patients suffering from pulmonary heart disease are randomly divided into 3 groups. In the normal group, 16 patients are treated with a complex of therapies, such as anti-inflamatory therapy, antiasthma, oxygen inhalation, and so on. In the Cardiotonic Pill group, 14 patients are treated with Cardiotonic Pill, 10 pills/time, and 3 times/day. In the Gantangzhi group, 18 patients are treated with the intravenous drip—200 mg of Gantangzhi dissolved in 250 ml of 5% glucose injection, 1 time/day, and 10 days/period.

The results: After treatment with Cardiotonic Pill, the value of GSH-Px goes up, the value of LPO goes down, and, therefore, GSH-Px/LPO goes up. In comparison with the normal treatment group, there is a significant difference. See Table 14 below.

TABLE 14

| | | Indices before and after Treatments | | | | |
|---|---|---|---|---|---|---|
| | | GSH-$P_x$ (U/mgHb) | CAT (U/gHb) | SOD (U/gHb) | LPO (nmol/ml) | GSH-$P_x$/LPO |
| Healthy people group | | 140.6 ± 35.2 | 312.7 ± 58.1 | 5799.8 ± 948 | 4.2 ± 1.2 | 34.2 ± 8.7 |
| Normal group | Before treatment | 101.3 ± 23.6 | 300.4 ± 107.7 | 5740.5 ± 939.0 | 5.6 ± 1.9 | 20.4 ± 8.8 |
|  | After treatment | 120.6 ± 20.6# | 390 ± 184.3# | 6076.8 ± 1091 | 4.3 ± 1.2## | 31.3 ± 15.1## |
| Cardiotonic Pill group | Before treatment | 108.8 ± 28.3 | 233.1 ± 70.2 | 5863.3 ± 1072.7 | 5.9 ± 2.0 | 18.5 ± 7.6 |
|  | After treatment | 158.2 ± 40.7##** | 328.4 ± 78.5##* | 5582.8 ± 1094.7#* | 4.1 ± 1.6##** | 36.4 ± 6.7##** |

Note:
Comparing those before treatment with those after treatment,
p > 0.05,
p < 0.05,
*p > 0.05,
**p < 0.05.

The conclusion: Cardiotonic Pill has the function of antioxidation, and can lighten the lipid peroxidation reaction and raise the ability of antioxidation of human body.

Treatment with Cardiotonic Pill for Essential Hypertension

The method: (1) The choice of patients: Select those patients suffering from Phase I or II essential hypertension, but without secondary hypertension or cardiac, hepatic and renal insufficiencies.

(2) The administration: Stop the patients from taking any western and traditional Chinese medicines (except for hypotensors) for two weeks, and then, in the third week, measure their blood pressures and blood rheologyical indices and take down their clinical manifestations. The double blind method is adopted. In the Cardiotonic Pill group, the subjects take orally Cardiotonic Pill, 10 pills/time, and 3 times/day. In Compound Danshen Tablet group, the subjects take orally Compound Danshen Tablet, 5 tablets/time, and 3 times/day. The subjects in the control group take placebos, and the period of treatment is six weeks.

The results: (1) Effect on the viscosity of whole blood. After treatment, the viscosities of whole blood of patients in both the Cardiotonic Pill group and the Compound Danshen Tablet group drop remarkably, but the curves of the viscosities of whole blood in the Cardiotonic Pill group at any shear rates go down more sharply than those in the Compound Danshen Tablet group. See Table 15.

TABLE 15

Effect of Cardiotonic Pill on the Viscosity of Whole Blood (mPas, x ± s)

| Groups | | $3.83\ s^{-1}$ | $28.3\ s^{-1}$ | $192\ s^{-1}$ |
|---|---|---|---|---|
| Cardiotonic group (30 subjects) | Before treatment | 18.27 ± 2.85 | 5.82 ± 0.93 | 4.54 ± 0.78 |
| | After treatment | 11.79 ± 3.75**\*##&& | 4.78 ± 0.84**\*##&& | 3.98 ± 0.65**\*##&& |
| Compound Danshen Tablet group (30 subjects) | Before treatment | 17.69 ± 1.96 | 5.86 ± 0.79 | 4.69 ± 0.54 |
| | After treatment | 14.68 ± 3.41**&& | 5.69 ± 0.81*& | 4.42 ± 0.59**&& |
| Control group (15 subjects) | Before treatment | 17.65 ± 2.07 | 5.69 ± 0.79 | 4.75 ± 0.58 |
| | After treatment | 18.02 ± 2.32 | 5.71 ± 2.76 | 4.86 ± 0.65 |

Note:
In comparison with those of the same group before treatment, *p < 0.05, **P < 0.01. Comparing with those of the Cardiotonic Pill group after treatment, #p < 0.05, ##p < 0.01. Comparing with those of the control group after treatment, &p < 0.05, &&p < 0.01.

(2) Effect on the deformation and the aggregation of erythrocytes. After treatment, the deformation of erythrocytes in Cardiotonic Pill group is markedly greater than that before treatment, and the area and the index of aggregation are observably smaller than those before treatment. And comparing with the Compound Danshen Tablet group, the Cardiotonic Pill group declines much faster (p<0.01). See Table 16.

TABLE 16

Effect of Cardiotonic Pill on the Deformation and the Aggregation of Erythrocytes (x ± s)

| Groups | | Index of Deformation | Index of Aggregation | Area of Aggregation (integral) |
|---|---|---|---|---|
| Cardiotonic group (30 subjects) | Before treatment | 0.4115 ± 0.0360 | 4.06 ± 0.39 | 841.12 ± 67.68 |
| | After treatment | 0.4274 ± 0.034*& | 3.41 ± 0.36**\*#&& | 683.52 ± 69.09**\*#&& |
| Compound Danshen Tablet group (30 subjects) | Before treatment | 0.4066 ± 0.0290 | 3.98 ± 0.34 | 806.90 ± 66.30 |
| | After treatment | 0.4180 ± 0.0281*& | 3.64 ± 0.39**\*\*&& | 716.12 ± 84.29**& |
| Control group (15 subjects) | Before treatment | 0.4091 ± 0.0376 | 4.02 ± 0.41 | 812.52 ± 65.64 |
| | After treatment | 0.4001 ± 0.0381 | 4.01 ± 0.39 | 804.44 ± 68.06 |

Note:
In comparison with those of the same group before treatment, *p < 0.05, **p < 0.01. Comparing with those of the Cardiotonic Pill group after treatment, #p < 0.05, ##p < 0.01. Comparing with those of the control group after treatment, &p < 0.05, &&p < 0.01.

(3) Effect on Blood Pressure. After treatment, the systolic pressures and the diastolic pressures of patients in both the Cardiotonic Pill group and the Compound Danshen Tablet group drop markedly (p<0.01), and there is no evident difference between the two groups. See Table 17.

(4) Effect on symptoms of hypertension. The patients in both the Cardiotonic Pill group and the Compound Danshen Tablet group improve a lot in terms of such symptoms as headache, dizziness, and numb extremities (p<0.01), but do not improve in insomnia. See Table 18.

TABLE 17

Effect of Cardiotonic Pill on Blood Pressure (mmHg, x ± s)

| Groups | | Systolic pressure | Diastolic pressure |
|---|---|---|---|
| Cardiotonic group (30 subjects) | Before treatment | 155.00 ± 8.08 | 90.70 ± 7.93 |
| | After treatment | 149.20 ± 8.89**&& | 86.59 ± 8.30**&& |
| Compound Danshen Tablet group (30 subjects) | Before treatment | 152.93 ± 9.59 | 92.59 ± 8.30 |
| | After treatment | 146.02 ± 10.20**&& | 88.55 ± 7.22**&& |
| Control group (15 subjects) | Before treatment | 154.06 ± 7.05 | 90.90 ± 9.10 |
| | After treatment | 152.08 ± 9.25 | 91.10 ± 8.70 |

Note:
In comparison with those of the same group before treatment, **P < 0.01. Comparing with those of the control group after treatment, &&p < 0.01.

TABLE 18

Effect of Cardiotonic Pill on Clinical Symptoms of Hypertension (patients)

| Groups | | Headache | | Dizziness | | Numb extremities | | Insomnia | |
|---|---|---|---|---|---|---|---|---|---|
| | | Yes | No | Yes | No | Yes | No | Yes | No |
| Cardiotonic group (30 subjects) | Before treatment | 20 | 10 | 16 | 14 | 12 | 18 | 8 | 22 |
| | After treatment | 7 | 23* | 2 | 28* | 3 | 27* | 4 | 26 |
| Compound Danshen Tablet group (30 subjects) | Before treatment | 22 | 8 | 17 | 13 | 10 | 20 | 6 | 24 |
| | After treatment | 15 | 15* | 8 | 22* | 3 | 27* | 6 | 248 |
| Control group (15 subjects) | Before treatment | 8 | 7 | 6 | 9 | 4 | 11 | 4 | 11 |
| | After treatment | 7 | 8 | 5 | 10 | 3 | 12 | 2 | 13 |

Note:
In comparison with those of the same group before treatment,
*P < 0.01.

The conclusion: The Theological property of erythrocytes of patients suffering from essential hypertension is clearly abnormal. The deformation of erythrocytes debases clearly, while the aggregation rises distinctly. The experiment shows that Cardiotonic Pill has the functions of markedly reducing the viscosity of whole blood and the index of and the area of aggregation of erythrocytes, and greatly raising the ability of deformation of erythrocytes. Cardiotonic Pill can also lower the blood pressure and improve clinical symptoms of the patients. And thus, Cardiotonic Pill is of great benefit to preventing or postponing the occurrence of essential hypertension and cardio-cerebral syndrome.

Toxicity

DSP is safe and nontoxic. In China, over 5 million patients have been treated with DSP without severe side effects. Mild side effects, headache or dizziness, have been reported in a minor portion of patients.

Summary of Clinical Studies

DSP is a new generation Chinese medicine for treating coronary heart disease. Clinical studies demonstrate that DSP alleviates as well as prevent angina by improving cardiac function, reducing myocardial ischemia, inhibiting platelet activation thus reducing blood stasis, and decreasing plasma cholesterol. The therapeutic efficacy of DSP was superior to another form of Chinese medicament Dan Shen tablets. DSP is as efficient as drugs used in the USA. DSP is aleviate angina as efficiently as nitroglycerine, prevents angina as efficiently as the long-acting nitrate isosorbid dinitrate, and inhibits platelet aggregation as effectively as aspirin. DSP is nontoxic: over 5 million people have been treated without noticeable side effects in most cases.

Preclinical Studies

Preclinical studies reveal the mechanism by which DSP prevent as well as alleviate angina.

DSP Alleviate Angina by Increasing Blood Flow.

Wistar rats, approximately 260 g, were anesthetized by urethane, opened the chest, excise the heart, perfused in the Langendorff mode at 37° C. And constant coronary perfusion pressure of 65 cm $H_2O$.

After stabilized the heart rate, various amounts of DSP or Danshen tablet were applied each time through lateral branch of aorta cannula. Subsequently, the coronary flow and the heart rate were measured. DSP increased coronary flow in a wide dosage. Danshen tablet, on the other hand, increased coronary flow at a narrow dosage. See Table 19 below.

TABLE 19

DSP increases coronary flow

| | Dose (mg/ml) | Coronary flow Pretreatment | post-treatment |
|---|---|---|---|
| | None | 7.0 ± 1.1 | 7.1 ± 0.97 |
| DSP | 5.8 | 7.2 ± 1.1 | 7.0 ± 1.4 |
| | 290 | 6.7 ± 1.6 | 8.7 ± 1.4 |
| | 580 | 6.7 ± 1.5 | 9.3 ± 2.9 |
| DS Tablet | 5.8 | 6.7 ± 1.4 | 7.1 ± 1.5 |
| | 290 | 7.3 ± 1.7 | 9.1 ± 2.1 |
| | 580 | 6.8 ± 1.4 | 7.1 ± 1.5 |

The effect of DSP and Danshen tablets on heart rate was examined. Neither DSP nor Danshen tablet changes heart rate. See Table 20 below.

TABLE 20

DSP does not increase heart rate

| | Dose (mg/ml) | Heart rate Pretreatment | post-treatment |
|---|---|---|---|
| | None | 194 ± 17 | 193 ± 12 |
| DSP | 5.8 | 180 ± 11 | 189 ± 9 |
| | 290 | 188 ± 7 | 184 ± 8 |
| | 580 | 173 ± 14 | 167 ± 13 5.8 |
| DS tablet | 5.8 | 180 ± 11 | 189 ± 9 |
| | 290 | 189 ± 16 | 183 ± 14 |
| | 580 | 186 ± 23 | 171 ± 8 |

DSP Increases Coronary Flow by Relaxing Vascular Smooth Muscle thus Dilating Vessels.

The effect of DSP on potassium-induced vasocontraction of rabbit aortic strip was examined. DSP relaxed smooth muscle thus dilating vessels significantly. Similar effects were observed in the experiments using pig coronary artery rings.

DSP Inhibits Platelet Aggregation

The effect of DSP on platelet aggregation was examined. Rabbit platelets were treated with DSP and aggregation was examined. DSP inhibited platelet aggregation significantly. See Table 21 below.

TABLE 21

DSP inhibits platelet aggregation

| DSP (mg/ml) | #animals | Aggregation ratio (%) | inhibition (%) |
|---|---|---|---|
| 0 | 6 | 6.7 ± 4.4 | 0 |
| 1.8 | 6 | 42.7 ± 2.5 | 8.3 ± 4.5 |
| 3.5 | 6 | 33.4 ± 3.4 | 23.6 ± 6.7* |
| 7 | 6 | 25.3 ± 2.1 | 37.6 ± 5.9* |
| 14 | 6 | 15.8 ± 3.0 | 69.0 ± 6.9* |

Table 22 shows micronucleus rates in mice at Different Time After treatment with the herbal composition of this invention (8400 mg/kg).

TABLE 22

| Time (h) | Polychromatic RBCs | Micronucleus Cells | Micro-rates (%) (x ± SD) |
|---|---|---|---|
| 12 | 6,000 | 9 | 1.5 ± 0.8 |
| 24 | 6,000 | 11 | 1.8 ± 0.7 |
| 36 | 6,000 | 11 | 1.8 ± 1.2 |
| 48 | 6,000 | 11 | 1.8 ± 1.5 |
| 72 | 6,000 | 13 | 2.2 ± 0.7 |
| Solvent 24 | 6,000 | 9 | 1.5 ± 1.4 |

Table 23 shows the micronuleus rates in Mice at 24 hrs after DSP & CP Administration.

TABLE 23

| Dose (mg/kg) | Polychromatic RBCs | Micronucleus Cells | Micro-rates (%) (x ± SD) |
|---|---|---|---|
| 8,400 | 6,000 | 12 | 2.0 ± 0.6 |
| 840 | 6,000 | 9 | 1.5 ± 1.0 |
| 84 | 6,000 | 11 | 1.8 ± 1.0 |
| Solvent | 6,000 | 9 | 1.5 ± 1.4 |
| CP (80 mg/kg) | 6,000 | 138 | 23.0 ± 4.0* |

*Compare with solvent P < 0.01.

Table 24 shows assessment criteria for graded effectiveness of tested drugs.

TABLE 24

| Parameters\Effects | Very high effect | High Effect | Effect | No effect |
|---|---|---|---|---|
| RBC aggregation status | No | A little | Marked | Severe |
| onset Time | <90 | 90–180 | 180–300 | >300 |
| Micro-blood flow status | Better than normal | Turn to normal | Improved | Deteriorated |
| Duration (min) | >15 | 15–10 | 10–5 | <5 |

DSP Improves Microcirculation

The effect of DSP on microcirculation in Chinese hamsters was examined. DSP improved microcirculation for 23 minutes within 111 minutes of buccal administration in all animals. See Table below.

TABLE 25

DSP improves microcirculation

| | onset Time (min) | Duration (min) | Effect rate (%) |
|---|---|---|---|
| DSP | 111 | 23 | 100 |

Table 26 shows the protective effect of DSP on the myocardium induced by pituitrin in rats (second period).

TABLE 26

(n = 8)

| | | After medication | | |
|---|---|---|---|---|
| Group | Dosage (g/kg) | Before medication | Before pituitrin | After pituitrin (40 s–15 minutes) Number of rats with abnormal ECG |
| Control | | Normal | Normal | 7 |
| DSP | 0.4 | Normal | Normal | 3* |
| | 0.8 | Normal | Normal | 1** |
| | 1.2 | Normal | Normal | 1** |
| DST | 0.4 | Normal | Normal | 4 |
| | 0.8 | Normal | Normal | 1** |

Compared with the control. *p < 0.05; **p < 0.01.

Table 27 shows the inhibitory effect of DSP on myocardial ischemia induced by pituitrin in rat.

TABLE 27

| Group | Dosage (g/kg) | Inhibition (%) |
|---|---|---|
| DSP | 0.4 | 71.4* |
| | 0.8 | 85.7* |
| | 1.2 | 71.4* |
| DST | 0.4 | 42.8* |
| | 0.8 | 85.7* |

As compared with the control. *p < 0.05.

Table 28 shows the protective effect of DSP on the myocardial ischemia induced by pituitrin in rats (first period).

TABLE 28

(n = 8)

Changes in T-ST of ECG- (lead II) in the first period

| | | After medication | | | | |
|---|---|---|---|---|---|---|
| | | | | After pituitrin (0–40 s.) Number of rats with abnormal ECG | | |
| Group | Dosage (g/kg) | Before medication | Before pituitrin | elevated T | inverted T | Total |
| Control | — | Normal | Normal | 4 | 3 | 7 |
| DSP | 0.4 | Normal | Normal | 3 | 0 | 3* |
| | 0.8 | Normal | Normal | 1 | 1 | 2* |
| | 1.2 | Normal | Normal | 2 | 1 | 3* |
| DST | 0.4 | Normal | Normal | 3 | 2 | 5 |
| | 0.8 | Normal | Normal | 1 | 1 | 2* |

As compared with control.
*P < 0.05.

Cardiotonic Pill's Action of Clearance on Oxygen Free Radicals

The study of Cardiotonic Pill's action of clearance on oxygen free radicals is carried out by using electron paramagnetic resonance (EPR) and spin trapping, with superoxide anions and hydroxy radicals produced by using the xanthine-xanthine oxidase system and the $H_2O_2$—$Fe^{2+}$ system respectively.

The method: (1) Production of hydroxy radicals. Set up a test model according to the Fenton Principle. Mix up $H_2O_2$, ferrisulphas and DMPO (5,5-dimethyl-pyrroline-l-oxide), and then carry out the EPR testing. The resulting signals serve as the control. Add Cardiotonic Pill in the treatment group.

(2) Production of superoxide anions. Set up a test model based on the xanthine-xanthine oxidase reaction. Mix up xanthine, Dietrylene triamine Pentacetic acid, DMPO and xanthine oxidase, and then carry out the EPR testing. The resulting signals serve as the control. Add Cardiotonic Pill in the treatment group.

Ten samples for each of the four groups are tested, and the results are expressed in terms of the average. T-test is applied in the statistical analysis.

The Results: (1) Cardiotonic Pill's action of clearance on hydroxy radicals produced by the H2O2-Fe2+ system. An adduct DMPO-OH will be generated when a hydroxy radical is captured by a DMPO. The peak value of the adducts in the control group is 11.8±0.6 relative units, while that in the Cardiotonic Pill group is 4.1±0.5 relative units. There is a significant difference between them (p<0.01), and the clearance rate of Cardiotonic Pill is over 65%.

(2) Cardiotonic Pill's action of clearance on superoxide anions produced by the xanthine-xanthine oxidase system. An adduct DMPO-OOH will be generated when a superoxide anion is captured by a DMPO. The peak value of the adducts in the control group is 10.6±0.67 relative units, while the spectral signals in the Cardiotonic Pill group disappear completely. In comparison with the control group, there is a significant difference (p<0.01), and the clearance rate of Cardiotonic Pill is 100%.

The above experiments show that Cardiotonic Pill has an effective action of clearance on superoxide anions produced by the xanthine-xanthine oxidase system and hydroxy radicals produced by the H2O2-Fe2+ system.

Cardiotonic Pill's Effect on Free Radicals of Cerebral Ischemia Reinfusion Injury Tissue of Rats The method: Take 30 SD rats, and randomly divide them into 3 groups, which are the feigned operation group (An operation is performed, but the blood vessels and nerves are not ligated), the cerebral ischemia reinfusion model group and the Cardiotonic Pill group (4 g/kg). After the 3-day continuous intraperitoneal (Ip) administration, and two hours after the administration on the third day, the rats are anaesthetized with the 20% Ethylurethanm and their conducting arteries in both sides of their necks and vagus nerves are separated and ligated. After a 30-minute reinfusion, cut off their heads and get their brains. Take about 500 mg of cortical tissues of their left-brains and hippocampus tissues in both sides, and put them into the liquid nitrogen for homogenization. After they are made into a homogenate with freezing physiological saline, centrifugate the homogenate. Take the supernatant and determine the activities of CAT and SOD and the contents of MAD and GSH.

The results: See Table 29. (1) Cardiotonic Pill's effect on the activity of CAT and the content GSH of brain tissues. The activities of CAT of brain cortex and hippocampus tissues and the content of GSH of the brain cortex in the cerebral ischemia reinfusion model group are much lower than those in the feigned operation group. Both the activity of CAT of hippocampus tissues and the content of GSH of the brain cortex in the Cardiotonic Pill group are significantly greater than those in the model group.

TABLE 29

The Activities of CAT and SOD and the Contents of MDA
and GSH of Brain Tissues of the Rats (mPas, x ± s) (n = 10)

| Groups | CAT Activity (U/mg Protein) | | GCH (μmol/mg Protein) | | SOD Activity (U/mg Protein) | | MDA (nmol/mg Protein) | |
|---|---|---|---|---|---|---|---|---|
| | Brain Cortex | Hippocampus | Brain Cortex | Hippocampus | Brain Cortex | Hippocampus | Brain Cortex | Hippocampus |
| Feigned Operation Group | 2.94 ± 0.17 | 2.78 ± 0.14 | 18.49 ± 0.70 | 16.87 ± 0.92 | 14.24 ± 0.90 | 20.34 ± 0.74 | 0.502 ± 0.054 | 1.084 ± 0.117 |
| Model Group | 2.17 ± 0.24$^8$ | 1.97 ± 0.23$^8$ | 14.76 ± 1.12$^8$ | 13.80 ± 0.74 | 10.44 ± 0.79$^8$ | 18.18 ± 0.62$^8$ | 0.718 ± 0.070$^8$ | 1.449 ± 0.140$^8$ |
| Cardiotonic Pill Group | 2.55 ± 0.35 | 2.79 ± 0.21$^3$ | 17.14 ± 0.76 | 15.76 ± 1.18$^3$ | 13.31 ± 0.77$^3$ | 20.59 ± 0.59$^3$ | 0.483 ± 0.065$^3$ | 1.069 ± 0.131$^3$ |

Note:
In comparison with the feigned operation group,
*p < 0.05; in comparison with the model group,
p < 0.05

(2) Cardiotonic Pill's effect on the activity of SOD and the content MDA of brain tissues. The activity of SOD of brain tissues in the model group is significantly lower than that in the feigned operation group, while the content of MDA is significantly higher. The activities of SOD of brain cortex and hippocampus tissues in the Cardiotonic Pill group increase significantly, while the content of MDA decreases significantly.

The conclusion: After cerebral ischemia reinfusion, the content of MDA in the brain tissues increases, while the content of GSH decreases. The activities of CAT and SOD, two important enzymes for clearing oxygen free radicals in the tissues, decrease significantly, which shows that during the course of cerebral ischemia reinfusion, a great lot of oxygen free radicals occur due to the failure of the function of the free radical clearance system. This leads to the lipid peroxidation, and then leads to the brain injury. Cardiotonic Pill can decrease the contents of MDA in the brain cortex and hippocampus tissues of reinfused rats and increase the content of GSH and the activities of CAT and SOD greatly, which shows that Cardiotonic Pill has the functions of markedly restraining the reactions of oxygen free radicals, controlling the lipid peroxidation and protecting damaged brain cells caused by ischemia reinfusion.

The Antioxidation of Cardiotonic Pill in Chronic Hepatic Injury

The method: The CCL4-high-fat-low-protein induced mild chronic hepatic injury model of the Wister rat is adopted. In the Cardiotonic Pill group, perfuse Cardiotonic Pill into the rats' stomachs at the dose of 4 g/kg, while in the normal and the model groups, perfuse the same amount of physiological saline. The activity of SOD is determined by using the xanthine oxidase method, while the content of the MDA is determined by using the improved thiobarbituric acid method.

The results: See Table 30. Comparing the model group with the normal group, the activity of SOD degrades, while that of MDA increases. In the Cardiotonic Pill group, however, the activity of SOD increases, while that of MDA degrades, making the Cardiotonic Pill group go back to the normal.

TABLE 30

The Activities of SOD and the Contents
of MDA in Chronic Hepatic Injury

| Groups | Rats | SOD (NU/mg.pr) | MDA (nM/mg.pr) |
|---|---|---|---|
| Normal group | 12 | 1.717 ± 0.521 | 15.21 ± 4.35 |
| Model group | 12 | 1.326 ± 0.3218 | 19.39 ± 4.62* |
| Cardiotonic Pill group | 11 | 1.710 ± 0.415# | 15.16 ± 4.29# |

Note:
In comparison with the normal group, *p < 0.05. In comparison with the model group, #p < 0.05

The conclusion: MDA is a major degradation product of the lipid peroxidation. MDA can badly damage the structure of the cell membrane, and then hepatic cells. SOD is a scavenger of super-oxide anion free radicals, and it can restrain the lipid peroxidation caused by free radicals. Cardiotonic Pill can significantly increase the activity of SOD and decrease the content of MDA, which will degrade the level of the lipid peroxidation and lighten the hepatic injury.

DSP is not Mutagenic

It was examined whether DSP is mutagenic in the Ames assay. DSP was not mutagenic. See Table 31 below.

TABLE 31

The mutagenicity of DSP (Ames test)

| | | colony number per dish | | | |
|---|---|---|---|---|---|
| | S9 | TA97 | Ta98 | TA100 | TA102 |
| DSP | | | | | |
| 0.0 | − | 141 ± 13 | 36 ± 3 | 161 ± 21 | 303 ± 44 |
| 0.5 | − | 140 ± 17 | 35 ± 2 | 148 ± 21 | 288 ± 15 |
| 5 | − | 136 ± 14 | 34 ± 4 | 154 ± 26 | 280 ± 16 |
| 50 | − | 133 ± 20 | 33 ± 5 | 142 ± 25 | 292 ± 37 |
| 500 | − | 109 ± 15 | 34 ± 3 | 154 ± 16 | 311 ± 32 |
| 5000 | − | 67 ± 8* | 30 ± 4 | 149 ± 27 | 298 ± 32 |
| 0.0 | + | 141 ± 13 | 44 ± 6 | 176 ± 19 | 296 ± 39 |
| 0.5 | + | 148 ± 13 | 42 ± 9 | 161 ± 27 | 296 ± 37 |
| 5.0 | + | 152 ± 11 | 44 ± 7 | 161 ± 16 | 292 ± 38 |
| 50.0 | + | 140 ± 18 | 37 ± 6 | 166 ± 9 | 307 ± 55 |
| 500.0 | + | 135 ± 21 | 42 ± 7 | 152 ± 22 | 287 ± 16 |
| 5000.0 | + | 119 ± 17 | 38 ± 7 | 162 ± 17 | 363 ± 57 |
| Dexon | | | | | |
| 50 | − | 2155 ± 814 | 952 ± 187 | 831 ± 114 | 1510 ± 211 |

TABLE 31-continued

The mutagenicity of DSP (Ames test)

| | S9 | TA97 | Ta98 | TA100 | TA102 |
|---|---|---|---|---|---|
| 2-AF | | | | | |
| 40 | − | 125 ± 18 | 38 ± 3* | 161 ± 16 | |
| | + | 1404 ± 644* | 1598 ± 124 | 1222 ± 309 | |
| DAN | | | | | |
| 100 | − | 364 ± 50 | | | |
| | + | 943 ± 102* | | | |

Production of Crude Drugs
1. Dan shen
(1) Quality Control

Crude drug Dan Shen was sampled from production arias throughout China. Chemical analysis was conducted on those samples from different bases for their chief components. The results showed that the quality of Dan Shen from an aria named Shangluo was the best of all and it proved that the climate of Shangluo is most suitable for the growth of Dan Shen. The active ingredients of Dan Shen such as tanshinone and salvianic acid A. were approved the best in quantity.

(2) Topography

Shangluo is geographically located at the East Longitude 108°34'20"~111°1'25" and North Altitude 33°2'30"~34°24'40" with an average sea level of 900 meters. The region is an area with low and median high mountains and is free of pollutions. The unpolluted clean air circumstance makes it ideal for the growth of drug plants.

(3) Climate

It is warm and semi-humid in climate, typical for the mountainous areas of transitional zone from the subtropics to the temperate. Affected by the South-eastern monsoons, it has obvious divisions for seasons and a great amount of rain. The precipitation of rainfall of the year in this area is estimated at 733.9-899 mm. The sunshine period is around 1874.1-2185 hours a year, with an annual sun irridiance of 119.57-124.36 kilocalories/cm$^2$. The temperature varies from 18° C.-40.8° C. A frost-free period lasts 198-218 days of the year.

(4) Soil

80% of the soil in Shangluo is arenaceous, most of the arable land comprises of neutral and alkalescent soil with a pH value of 6.5-8. Within 0-20 cm of the tillage layer, the soil nutrients consist of the following: 1.36% organic matter; 0.085% nitrogen; 18 ppm fast-effective phosphor; 136 ppm fast-effective potassium; and 60 ppm alkaline-hydrolyzed nitrogen. Heavy metals and other toxic matters contained in the soil do not exceed the agricultural standards set by the country. The region is rich in plants and animals. Local farmers use organic fertilizers.

(5) Heavy Metals:

The eight metals, including Lead, cadmium, mercury, arsenic, etc., the pesticide residues, air and water all meet the country environment standards.

(6) Standardization

The planting and plowing of Dan Shen follow the standard of Good Agriculture Practice (GAP). Technological know-how relevant to the growing of Dan Shen is compiled into a booklets and distributed among the Dan Shen growers in the base. During the planting seasons, technicians are sent to the fields to give growers training on the spot and offer technical support, so as to standardize the planting of Dan Shen on a large plantation-like scale.

(7) The Shangluo production base had bred and cultivated 20 different breeds of Dan Shen. Different Dan Shens were observed and compared in their growth situations, yield, appearance and chemical components for three years. The best breeds in quality chosen for large-scale plantation.

(8) Tissue cultivation and clone technology are adopted in the Dan Shen cultivation to accelerate the procedure and shorten the circle of growth.

(9) After a 30-day period of test-tube planting, an enlarged reproduction procedure is taken. It lasts 40 days before the root period. The root period will takes another 10 days that is for the plants to generate and enrich their roots. The rate of rooting usually reaches 90% or above. The plant can then be transferred to the nursery, where advanced spray irrigation device and conditions are controlled by computer technology. The plants can be transplanted to the outside field after a month cultivation in the nursery.

(10) According to the experts, the cultivated Dan Shen from our product base are not only in high quality but also productive for their productive roots (50% more in root weight than those from other areas), and high chemical composition (70% higher in active drug ingredients than samples from other places).

2. Natural Borneol
(1) Growth Conditions

The growth areas of natural Borneol are Xinhuang county of Hunan province, China, a region with mid-height hills at a sea level of 300-600 m. 60% of the area is covered by forest. The land consists of yellow and red sand soil with pH 5-6. No air or water pollutions are found within the region.

(2) Biological Characteristics of the Tree

Extremely strong growth capability, it grows in brushwood field, 300-400 trees per mu (equal to 666.7 m$^2$); Parts above branch leaves are collected; net gain is 1000 kg per mu.

(3) Reproduction and Transplant

Use grafting and cuttage technology for reproduction. The Plant grows in the nursery garden during the first year and is transplanted to the filed in the spring of the second year. The filed need to be fertilized and scarified periodically.

(4) The plant may grow up to 30 cm in height and 80-100 cm for the largest diameter. It contains natural Camphor in different parts of the plant: leafs, branches, trunk and roots. Among all, the leaves contain the most of Camphor content.

(5) The Borneol-type Camphor from Xinghuang is one of the natural variation of Cirnamonium glandullferm (wall) Noes. The Camphors trees vary in contents of Camphor and Borneol, Some are low in Borneol, high in Camphor while others high in Borneol and low in Camphor. Through an assay with large amount of samples and many HPLC analyses, we finally choose a kind of Camphor trees that contains over 80% Borneol with less impurity.

3. Radix Notoginseng
a. Seeds of the Plant
(1) Determination of Radix Notoginseng With the PCR reaction for molecular mass marking, Radix Notoginseng can be stained observed, Radix Notoginseng has its characteristic DNA fingerprinting.

(2) Shape and properties

The Radix Notoginseng seed has a round, circular body. For seeds of different growth period, Radix Notoginseng has 2-year or 3-year seeds. The 2-year seed is 0.45-0.55 cm in diameter and 95-103 grams in weight for its dried grain. The 3-year seeds is 0.54-0.65 cm in diameter and 98-109 grams in weight for its dried grain.

(3) Suitable Temperature for Seed Sprouting

The appropriate temperature for seed sprouting is 10-30° C., the ideal temperature is 15-20° C.

(4) Water Content

The amount of water contained should be 60-70%, if water content is below 20% for a long period of time, the seeds will lose vivacity.

(5) Dormancy

The seeds have a tendency to go through dormancy for 45-60 days after collection.

(6) Life Span

The seeds have a life span of 15 days in natural state after they are collected.

(7) Requirements for Storage of Seed

Seeds for storage should be collected from the plants that grow more than two years and the tree should be growing prosperously for parts above the earth and pest-free. It is recommended that seeds be collected from three-year plants.

(8) Management for the Seed Reservation Field

Seed reservation field should be better managed than the regular production fields, contaminated plants should be disposed of at all times, pests should not come in contact with the buds under any circumstances. During period of sprouting of buds and leafs, 3000 ppm of YunDa-120 and 400 times solution of Yang Kang biological fertilizer should be sprayed twice. And, during florescence and fruit period, Phytokinin is sprayed.

(9) Harvest Period of the Seed

The harvest period of Radix Notoginseng seed is from the end of October to the beginning of December.

(10) Methods for Collection of Seeds

The collection of the seeds is decided dependant upon the levels of maturity of the seeds. The seeds from trees that grow stronger will be collected and stored separately. The base strictly prohibits collection of immature plants.

(11) Processing

Plants are washed immediately after collection while pulps and blighted seeds are picked out. Dry the plants in the sun after washing.

(12) Storage

Use 300 times solution of 58% metalaxyl manganous zinc dissolvable liquid to treat Radix Notoginseng seeds for 30 minutes. let the surface of the seeds become dry, and store the seeds with wet sand containing 20% water. It is a crucial step for the process.

(13) Packaging

Final products are packaged in uncontaminated containers, There should be signs that indicate the date of collection, processing, and the product batch number.

(14) Transporting

Clean, waterproof and ventilated transportation vehicles instruments should be used for transportation in order to prevent the product being contaminated with toxic matters. If it takes more than 8 hours for transportation, the product seed should be with the wet sand.

(15) Test for Vitality of the Seeds

Use the TTC methods: weigh accurately 1 g of tetrazolium powder and dissolve it in 1000 mL of distilled water to make up the solution of 0.1% TTC. Immerse the sample into the solution and keep it for 24 hours, take it out and cut it into half and place one-half into a culture disk. Use the prepared 0.1% TTC to dye the sample for 30 minutes. The vitality of the seeds can be determined by the color of the seeds

(16) Inspection of Pests
  i. Observe the seed with human eyes while placing 500-1000 sample pellets on a white sheet of paper or glass. If unusual spots or pests appear on the surface of the sample, the contamination can be decided. Contaminated samples should be taken apart and be identified for its level of contamination.
  ii. Cutting and Inspect: use a scalpel to cut and open 2 sample sets each contain 100 seeds. Calculate the number of contaminated seeds to determine the level of contamination.
  iii. Smell to inspect samples: place them in hand and detect them by nose for any moldy odor. Or simply leave sample in a cup containing heated water (60-70° C.), and covered for 2-3 minutes, pour out the water and smell the seeds. The seeds should send forth a delicate fragrance, if not, it is probably contaminated.

(17) Color Inspection

An uncontaminated seed should have light yellow and white color.

(18) Microscopic Inspection

Pick out 5 test sample sets by random (each sample contains no less than 50 ceeds), place the samples in a culture disk for 24 hours. Observe them under a microscope to detect them for any pathogenic bacteria, if so, calculate the level of contamination.

b. Seedling of the Plant (1) Temperature for Sprouting

The temperature for Radix Notoginseng's sprouting is 1-20° C., the ideal temperature is 15° C.

(2) Water Content

The water content of the soil used for seedling plant is 20-25%.

(3) Storage

The development of Radix Notoginseng from resting bud to sprouting requires 90 days of dormancy period. 100 ppm of gibberellin can help shorten the Radix Notoginseng's dormancy period.

(4) Refining

Radix Notoginseng's refinery period is from the beginning of December to the end of January. While refining, the roots should be handled with care. Plant immediately after refinery.

(5) Transportation

Radix Notoginseng cannot be transported over long distance, otherwise it will be damaged. If unavoidable, Radix Notoginseng should be placed in a ventilated container with soil, without direct exposure to sunlight.

(6) Quality Inspection
  i. For weight of each unit, choose 300-500 seedling plant as samples, put each 100 seedling plants in a group, weigh them on the balance and calculate the unit weight.
  ii. For pesticide inspection: set up four groups of samples each contains 100 seedling plants. Place samples on a glass disk and observe the samples with human eyes or 5-10 times magnifying lens to check for their pesticide.
  iii. Set up four groups of sample each contains 100 plants, slice the samples for an observation under the microscope.

c. Culture of the Seedling (1) Field Condition

Radix Notoginseng seedling plants are cultured in the best-conditioned areas. The base uses centered culture and large-scaled cultural method.

(2) Environment

The area is totally free of pollutions. The air quality is above level 2 of GB 3059-96 standard.

(3) Water Resources

The water resources consist of rainwater, underground water, and natural running water. Water quality in the area is monitored with the GB 5084-92 standard.

(4) Soil

Radix Notoginseng cannot be planted in oozy soil, the amount of heavy metals in the soil chosen for Radix Notoginseng must be within relevant country standard.

(5) Ideal Soil

For a good result expected, we choose acidic soil (pH 5.5-7.0) with a slope no more than 15°. A level no more than 1600 m above the sea should be with 8-12% of sunshine, and level more than 1600 m above sea level should be 10-20% of sunshine.

(6) Temperature

During sprout period the atmospheric temperature should be at 20-25° C., and the earth temperature is at 10-15° C. During bearing period is the best atmospheric temperature that is 20-25° C., and the best soil temperature that is 15-20° C.

(7) Water Content

Water content of soil should be at 25-30%.

(8) Soil Preparation

Soil plotting should be repeated for 3 times before planting, and soil be exposed under sunlight, it helps to exterminate bacteria substance in the soil.

(9) Handle with Soil

For prevention of root damage, 75-100 g of lime is used each square meter before transplanting.

(10) Construction and Management of Shade

The shade is 1.8 m above ground with a 2 m deep trench below the ground. Sunlight penetration is best at 8-10% if in area of no more than 1600 m above sea level, or 10-15% if it is more than 1600 m. The ground should be flat; deep layer of the earth should be lose; while the surface level of the earth should be rigid. Planting season is best at the end of December to the end of January. Before planting, the seeds should be immersed in 58% metalaxylic zinc (500-800×) or 1.5% antimycin (200 ppm) for 30-50 minutes and dip out to let dry. This is to protect the plant from diseases (Coated seeds do not have to undergo the above procedures) Density of planting is to be 4×5 cm or 5×5 cm, with 100-200 thousand seeds per mu of land. Use special tools to create a shallow gutter and use machine or hands to seed and plant. Seeds are covered with fine soil completely.

After all, fertilizing, watering and weeding tasks are performed. Weeds should be eliminated all the time. If the shade is broken, it should be repaired immediately and ensured the correct penetration of sunlight. Natural fertilizers including poultry waste, stove dust, and bone dust (human waste should not apply)

d. Radix Notoginseng Cultivation (1) Topology

The ground is best be with a moderate slope under 15° and a good exposure to sunshine.

(2) Soil Texture

It is the best if the ground is deeply seated with loose and sand soil.

(3) Soil pH Should be at 5.5-7.

(4) Pre-Planted Crops

Corns, wheat, and beans are pre-planted in new fields in avoid of soil destruction.

(5) Sea Level 1400-1800 m above sea level near an altitude of 23.50 is the location of the most suitable Radix Notoginseng area for cultivation.

(6) Sunshine

Radix Notoginseng is a kind of plant that requires only 8-20% of sunshine. The amount of sunshine should be varied increased in respect to different period of its growth. However, too much sunshine exposure will result in stagnant plants.

(7) Water Content

The water content within the soil should be at 25-30%.

(8) Fertilizer

Organic fertilizers are used along with compound fertilizers, micronutrient fertilizers, or trace-element fertilizers.

(9) Temperature

The average temperature is estimated at 15-18° C. during the year in the Radix Notoginseng area. During sprout period, atmospheric temperature should be, the most suitable, at 20-25° C., and soil temperature 15° C. During nutrient development and blooming period, temperature is better be kept at 25° C. If the temperature is below 15° C., florescence will be affected.

(10) Filed Division

Before cultivation, the field should be ploughed and loosened 3 times until its structure becomes powderized.

(11) Soil Management

Before sowing and transplanting, apply 75-100 g of quick lime to soil for sterilization purposes.

(12) Standards of the Bed

Flat ground soil bed of 20-25 cm in height, at slope area it should be 15-20 cm. The width of the bed is between 120 and 140 cm in a shape of a tile. The soil at the bottom of the base should be loose and that on the top should be solid, that is for better penetration.

(13) Seed Soaking

During transplanting, soak seed for 30-50 minutes in 58% metalaxyl (500-800×) and then let dry, this will prevent plant from diseases and eliminate pests.

(14) Density of Planting

Keep a distance of 10×12.5 cm-10×15 cm in plant density. That is 26-32 thousand plants every mu.

(15) Methods for Transplanting

Seedlings are planted facing the same direction for management purposes. In case of slope grounds, seedlings are planted from low end to the high ground. The first row of seedlings is facing up while the second row faces down. Buds are also to face upward, and the bottom is to face inward.

(16) Covering of Soil

Use powdered, loose, and moistures soil to cover the seedlings completely, without exposing the roots or the buds.

(17) Fertilization

Use poultry waste, stove ash, bone ash, Calcium Magnesium Phosphate, etc as specialized fertilizer.

Second Series of Experiments

This invention involves a medication which can prevent and cure coronary heart disease with angina pectoris, the methods of manufacture and other usages of the medication. The medication, Dan Shen Pill (DSP), is made from a variety of Chinese herbs using a series of standardized procedures.

DSP is an improvement on Dan Shen Tablet (DST) (recorded in Pharmacopoeia of the People's Republic of China in Edition, 1977, 1985, 1995, and 2000), but there are significant differences between DSP and DST: proportions in their formulas, manufacturing techniques and their clinical results.

The number of patients with cardiovascular or cerebrovascular diseases increases along with higher living standards (better supply of foods), the worldwide aging problem, and young adult's involvement. It has become the second most-common diseases worldwide threatening the health of human beings. Angina pectoris is caused by insufficient blood and oxygen supply to the heart. The main clinical symptom is chest pain. It is caused by atherosclerosis or spasms of coronary artery in about 90% of the angina pectoris patients.

The major treatments for angina pectoris are vessel dilation, lowering of blood viscosity, anti-aggregation of platelets and anti-coagulation. The traditional medicines used are nitrates, beta-adrenoceptor blocking drugs and calcium-channel blocking drugs. However, all these drugs have many side effects which make them unsuitable for long-term use. For example, patients experience a swelling sensation in their heads, faster heartbeat and even coma after taking glyceryl trinitrate.

Although there are many Chinese herbal medicines used for treating angina pectoris, fewer people use them nowadays. DST or capsules are being sold in the market, but their manufacturing techniques are old, the efficacy is low and there are no quality standards. DST is taken orally and absorbed in the gastrointestinal tract, where it is absorbed into blood vessels after processing in the liver. The bioavailability is low, and the absorption speed is low, which is not suitable for the emergency treatment of patients with angina pectoris.

In order to compensate for the inadequacy of the above technology, the drug disclosed in this invention was developed to provide high efficacy for the prevention and cure of coronary heart disease with angina pectoris.

The other aims of this invention are to provide other medical uses in addition to the prevention and cure of coronary heart disease, the proportion of herb composition and the method of manufacturing this drug.

This drug is prescribed according to traditional Chinese medical theory and modern pharmaceutical research. Chinese medical theories state that chest pains are caused by blood stagnation in the arteries, lack of blood supply and blood nourishment to the heart. After pharmaceutical experimentation and clinical observation, Radix Silviae Miltiorrhizae is used as the main ingredient. Panax Notoginseng and borneol are the co-ingredients which eliminate blood stagnation, thereby preventing and curing coronary heart disease with angina pectoris. The above ingredients are grouped and mixed with other inactive ingredients to make DSP.

DSP can prevent and cure coronary heart disease with angina pectoris by the following mechanisms:

Increase by the blood flow to the ischemic area: dilating the coronary artery, increasing blood flow to the coronary artery, and activating peripheral circulation to improve blood supply to the ischemic area.

Removing of free radicals: removing free radicals released by hypoxia and ischemia, reducing damage to myocardial muscles and increasing myocardial ATP content to protect myocardial muscles. Preventing the aggregation of platelets: controlling the release of platelet factors, preventing platelet aggregation and increasing the PGI2/TXA2 ratio to prevent coagulation and thrombosis.

Lowering of blood cholesterol: controlling the biosynthesis of cholesterol and lowering the synthesis of TG and LDL.

Xin, Zhiqiang, et al. (1996) reported in the Chinese Journal of Integrated and Western Medicine on the effects of Radix Siliviae Miltiorrhizae on 24 patients with coronary heart disease and observed the changes in their LPO and SOD contents before and after treatment. Having compared these 24 patients with 20 healthy people, it was found that patients with coronary heart disease had a higher LPO content than normal healthy people and a lower SOD content. After undergoing treatment, patients' LPO level dropped significantly, while SOD level rose. Conclusions are that Radix Silviae Miltiorrhizae can lower LPO, increase SOD activity, decrease platelet aggregation, improve myocardial ischemia, and protect the myocardial membrane.

Chang, yingzi, et al. (1991) reported in the Chinese Journal of Pathology and Physiology on an experiment in which FeSO4/Ascorbic was introduced to monitor the damaging effects of oxygen-free radicals on rod-shaped H+-ATPase of rat myocardial muscles. The results showed that FeSO4/Ascorbic can lower the hydrolysis ability of the rod-shaped H+-ATPase. Moreover, Danshensu has an obvious protective function: It can prevent the decrease of the hydrolysis ability of rod-shaped H+-ATPase and shows a concentration-dependent relationship and saturation effect.

Zheng, Ruoxuan, et al. (1992) reported in the Chinese Journal of Integrated and Western Medicine on an experiement in which water extracted Radix Silviae Miltiorrhizae (5 g raw medicine/$k_g$), was injected into rats. The water extraction prevents acute myocardial ischemia caused by blockage of the coronary artery. The, increased ECG section ST caused by myocardial ischemia after treatment was much lower than that in the control group. The area of left ventricular ischemia is minimized and the animal's chance of survival is increased.

Han, Chang, et al. (1991) reported in the Journal of Chinese Pathology and Physiology on an experiment in which the rabbits are anesthetized, chests opened, coronary artery tied to create an acute myocardial ischemia model, and then tested the change in local blood flow and myocardial lipid peroxidation content, an ECG was conducted while the animal was observed. DSP was injected as a protective agent. The results showed that myocardial lipid peroxidation content increases along with a longer duration of ischemia. When the heart is reperfused with blood for 30 minutes after a 60 minute ischemia, the lipid peroxidation content still increases continually, which is obviously higher than that of a 60-mins control group, but similar to that of a 90-mins control group. The blood flow of local tissue in the ischemia area recovered 53.2% after reperfusion, while in the DSP-protected group, the ischemia area decreased 56% after reperfusion (P<0.005). Blood flow recovery in local tissue increased 32% (P<0.001).

Jiang, Wende, et al. (1982) reported in Journal of Shanghai the First Medicine College on an experiment which compared DSP, DS-781, PCAD and persantin using four different tests. Results: extraction of Radix Silviae Miltiorrhizae can significantly lengthen the toleration time for hypoxia and protect ischemic EC change in mice. It can also prevent the lowering of LVPSP and rising of LVEDP. In contrast, PCAD lowers LVPSP and raises LVEDP more obviously. Vein injection to the persantin group can lower LVPSP but has no effect on LVEDP. The minimization of the area of myocardio infarction by Radix Silviae Miltiorrhizae extraction is the most significant.

Wu, Huaizhu, et al. (1994) reported in the Chinese Journal of Bloodology that the active principle of Radix Silviae Miltiorrhizae can suppress ADP or collagen-induced platelet ATP release and release relative aggregation. Inhibition shows a volume-effect relationship. 0.01-0.08 mmol/L764-3 can prolong the lag period in which arachidonic acid guides the activation of bloodplatelets. When concentration is increased to 0.08 mmol/L, coagulation of blood platelets and the release of ATP can be fully controlled. Aequorin-loaded platelet suspension analysis discovered that 764-3 can obviously inhibit the increase in plasma $Ca^{++}$ concentration and inhibit $Ca^{++}$ internal reflux and the activity of internal $Ca^{++}$. 764-3 can significantly inhibit the production of AA-induced platelet TXB2. Conclusions: 764-3 may suppress the metabolism of AA blood platelets.

Sun, Ximing reported in Chinese Traditional and Herbal Drugs that research is being conducted on the pharmaceutical effects of Danshensu using the cell model. It has been discovered that Danshensu can lower the biosynthesis of cholesterol and obviously lower migration ratio of electrophoresis. The MDA content in oxidized lipoproteins decrease and the toxicity of oxidized lipoprotein is also reduced. It shows that Danshensu can prevent atherosclerosis.

Shi, Lin analyzed in the China Journal of Pharmacology (1990) the effects of PNS on the synthesis of PGI2 on the arterial wall and on platelet TXA2 content in mice by using radioimmunoassay. Results were ig PNS 25, 50, 100 mg/kg for 10 days continuously. Arterial PGI2 decreased, showing that there may be a relationship between the inbalance of PGI-TXA2, increased arterial PGI2 and the anti-AS functions of PNS.

Hu, Yuejuan (1992) reported in the China Journal of Chinese Maeteria Medica that coarse extraction of Panax Notoginseng i.p. can enhance mice's hypoxia tolerance, improve blood circulation and slow heart rate. It can counteract noradrenaline contraction of the main artery and relieve the spasms in the smooth muscles of the intestine. Mice stomach-reperfused with SCC powder suspension exhibit shortened bleeding and coagulation times. The above pharmaceutical reactivity of SCC is the same as Panax Notoginseng.

Xu, Qing (1993) reported in the China Journal of Chinese Maeteria Medica on an experiment using Panax Notoginseng leaves gross saponin 200 mg/kg, 100 mg/kg to perfuse two kinds of high-fat animals: rats and quail, for 7 days. Cholesterol and triglyceride levels of the animals were greatly lowered.

Sun, Jianjun, et al. (1994) reported in the Journal of Traditional and Herbal Drugs that the condition of patients with angina pectoris did not improve satisfactorily with traditional Chinese medicine, which typically removes blood stasis and promotes blood flow, with nitrate, or with Propranolol, and other medicine. However, after taking Panax Notoginseng together with those medications, or Panax Notoginseng alone, 10 out of 11 patients showed satisfactory progress after a one-month treatment.

Jiang, Wende (1979) reported in Acta Pharmaceutica Sinica that using a 0.5 g/tablet of borneol to infuse the stomach of anesthetized dogs with acute myocardial infarction caused by blockage of the coronary artery can slow heartbeat and reduce the difference between the oxygen content in the arteries and the veins. It can also lengthen hypoxia tolerance time in mice.

The invention is made up of the following ingredients and is ready to be used.

| | |
|---|---|
| Radix Salviae Miltorrhizae | 48%~97% |
| Panax Notoginseng | 2%~50% |
| Borneol | 0.2%~3% |
| Radix Salviae Miltorrhizae | 63%~94% |
| Panax Notoginseng | 4%~35% |
| Borneol | 0.5%~2% |
| Radix Salviae Miltorrhizae | 75.2%~90% |
| Panax Notoginseng | 9%~23.5% |
| Borneol | 0.5%~1.3% |
| Radix Salviae Miltorrhizae | 82.87% |
| Panax Notoginseng | 16.21% |
| Borneol | 0.92% |

The drug is manufactured according to the following method: Extract the ground Radix Salviae Miltorrhizae and Panax Notoginseng. Boil in water. Filter it, collect the filtrate, and concentrate it. Add ethanol to the concentrated filtrate and leave for settlement. Collect the clear part of the solution for ethanol recycling. Concentrate the settled portion into a plaster. Mix the plaster with borneol and other ingredients to form an agent.

The detailed manufacturing steps are described as follows:
1. Extract the ground Radix Salviae Miltorrhizae and Panax Notoginseng according to the above ratio. Add water and extract 2-4 times on heat. The temperature should be 60-100° C. Water volume should be 4-8 times the gross herb material. Filter and collect the filtrate, which is then concentrated until the volume-to-weight ratio is 1 L:0.7-1.3 kg.
2. Add 95% ethanol to the concentrated solution until the concentration of ethanol is 50-85%. Settle it for 4-24 hrs. Filter the clear part of the solution. collect the filtrate for ethanol recycling. Concentrate the filtrate into a plaster with a relative density of 1.15-1.45.
3. Mix the plaster and the above borneol and other ingredients to make the agent.

The main manufacturing method is to mix all the plaster, borneol and other ingredients, heat to melt them and transfer them to the pill maker. The pills are then poured into paraffin oil at a low temperature. The paraffin oil is removed, and the pills are made.

Polyethylene-6000, with a freezing point of 53~58° C., is added 2~6 times volume of the plaster and borneol. The temperature is maintained at 60~100° C. The temperature of the paraffin oil is 0~10° C. (ideally 5~10° C.). The pill weight is 5~50 mg/tablet, and the diameter is 1.95~4.29 mm.

This invention uses modern methods and technology to increase effective content and quality standards, and guarantee the safety and efficacy of this drug. This drug is a dripping pill and solid solvent. It is distributed evenly in the substrate in its molecular form to create an evenly distributed solid. The accuracy of dosage can be guaranteed. The drug molecules penetrate the substrate with no space in vacuum. This increases the stability of the drug.

After dissolving the drug and the substrate, the drug can be evenly distributed in the substrate, condenses to form crystals which are easily dissolved and absorbed, efficiently increases biological utilization, and reduces side effects. The drug is taken sublingually, avoiding the processing in the liver and increasing bioavailability. The effective ingredient is absorbed into the blood through the mucous membranes of the mouth and expresses its functions.

The following is a description of the animal experiments and clinical research explaining the effects of DSP.

DSP Animal Experiment Research

1. The Effects of Myocardial Ischemia, Myocardial Infarction, Blood Flow on Related Coronary Arteries, Myocardial Oxygen Consumption, and Blood Biochemical Standards of Anesthetized Dogs.

The effects of DSP on dogs with myocardial ischemia and myocardial infarction were observed. Based on changes in myocardial oxygen consumption and biochemical standards, its pharmaceutical effects on curing coronary heart disease were investigated.

1.1 Experimental Groups. (1) Blank control group, normal saline 3 ml/kg; (2) DSP group, 2 g natural drug/kg; (3) positive control group, Ditiazem, 5 mg/kg. All the above samples are diluted with normal saline to the same volume of 3 ml/kg and were given to the patient through the duodenum.

1.2 Experimental Method. The dogs are anesthetized with pentobarbital sodium. Chests were opened and coronary arterioles and the central part of the dorsal lower branch separated and tied to create an acute myocardial ischemia model. ECGs were recorded and the level of myocardial ischemia (increased section ST, ST) and area of myocardial ischemia (the total increased decimal places in section ST) were calculated. The oxygen content in the coronary artery was recorded. Blood serum creatine kinase (CK), lactate dehydrogenase (LDH), ET, TXB2 and 6-Keto-PGF1 were measured. The oxygen content of the aorta and coronary vein, and blood flow volume in the coronary arteries were measured to calculate myocardial oxygen consumption. Blood oxygen content in the coronary vein was measured to calculate myocardial oxygen content (myocardial oxygen content=(blood oxygen content in arteries-blood oxygen content in coronary veins)× blood flow volume in coronary artery/100).

The hearts were removed 180 mins after treatment and weighed, cut into slices, and colored with N-BT. The infarction area of each slice (N-BT-uncolorized area) and non-infarction area (N-BT colorized area) were measured. The percentage occupied by the infarction area in the ventricles was calculated and the whole heart was weighted.

The significance of the experimental results was tested by the t-testing method.

Results

1. Effects and area of myocardial ischemia of dogs. When compared with the control group, DSP can significantly reduce the scope and area of myocardial ischemia. See Tables 1.1 and 1.2.

2. Effects on the scope of myocardial infarction of dogs. When compared with the control group, DSP can significantly reduce the area of infarction. See Table 1.3.

3. Effects on venous blood oxygen content in dogs with myocardial ischemia. When compared with the control group, DSP can increase coronary venous blood oxygen content. See Table 1.4.

4. Effects on blood flow standards in dogs with myocardial ischemia. When compared with the control group, DSP can suppress the rise of CK and LDH which are caused by myocardial ischemia and myocardial infarction, release ET and TXB2, and raise 6-Keto-PGF content. See Tables 1.5, 1.6, 1.7.

Conclusions

DSP can significantly improve myocardial ischemia and myocardial infarction, raise the blood oxygen level of venous sinuses, inhibit the release of CK and LDH caused by damage to cardiac muscles, lower the activity of blood serum CK and LDH, suppress the activity of blood vessel substances, ET and TXB2, and raise the 6-Keto-PGF1/TXB2 ratio.

TABLE 1.1

The effects of different groups of medicines on different levels of Acute Myocardial hypoxia (Σ-ST)

| Group | Dosage/kg | Changing in percentage before dosage (100%) | After dosage (min) | | | | | | |
|---|---|---|---|---|---|---|---|---|---|
| | | | 15 | 30 | 45 | 60 | 90 | 120 | 180 |
| Normal Saline | 3 ml | 301.00 ± 16.26 | 337.00 ± 26.54 | 319.20 ± 15.22 | 325.00 ± 17.51 | 328.40 ± 15.69 | 342.20 ± 30.69 | 329.60 ± 19.74 | 301.40 ± 25.18 |
| (n = 5) | | (100%) | 112.27 ± 11.18 | 106.37 ± 8.81 | 108.19 ± 7.63 | 109.39 ± 8.35 | 114.04 ± 13.37 | 109.76 ± 8.94 | 100.47 ± 11.54 |
| Ditiazem | 5 mg | 302.80 ± 5.12 | 277.80 ± 31.13 | 226.20 ± 39.71# | 213.40 ± 40.40# | 186.20 ± 40.75## | 175.20 ± 41.11## | 468.00 ± 47.16## | 122.80 ± 33.76### |
| (n = 5) | | (100%) | 91.83 ± 10.98* | 74.87 ± 14.10** | 70.59 ± 13.85*** | 61.61 ± 14.00*** | 57.95 ± 13.94*** | 55.60 ± 16.05*** | 40.63 ± 11.43*** |
| Dan Shen Pill | 2 g | 291.40 ± 17.85 | 256.00 ± 50.45 | 245.80 ± 60.34 | 268.20 ± 58.15 | 246.80 ± 69.83 | 243.00 ± 57.51 | 201.60 ± 50.05## | 177.80 ± 54.22## |
| (n = 5) | | (100%) | 87.95 ± 16.89* | 84.06 ± 18.59* | 91.57 ± 17.03 | 83.97 ± 20.83* | 82.78 ± 16.16* | 68.90 ± 14.48*** | 60.56 ± 15.91** |

Notes:
Comparison with control group: *P < 0.05 P < 0.01 *P < 0.001
Comparison with the situation before dosage: #P < 0.05 ##P < 0.01 ###P < 0.001

TABLE 1.2

The effects of different groups of medicines on different levels of Acute Myocardiohypoxia (N-ST)

| Group | Dosage/kg | Changing in Percentage before dosage (100%) | After dosage (min) | | | | | | |
|---|---|---|---|---|---|---|---|---|---|
| | | | 15 | 30 | 45 | 60 | 90 | 120 | 180 |
| Normal Saline | 3 ml | 29.60 ± 0.55 | 29.60 ± 0.55 | 29.60 ± 0.55 | 29.60 ± 0.55 | 29.60 ± 0.55 | 29.60 ± 0.55 | 29.60 ± 0.55 | 29.60 ± 0.55 |
| (n = 5) | | (100%) | 100.00 ± 0.00 | 100.00 ± 0.00 | 100.00 ± .000 | 100.00 ± 0.00 | 100.00 ± 0.00 | 100.00 ± 0.00 | 100.00 ± 0.00 |
| Ditiazem | 5 mg | 30.00 ± 0.00 | 29.80 ± 0.45 | 29.60 ± 0.55 | 29.20 ± 1.10 | 28.40 ± 1.52 | 27.00 ± 2.00# | 26.80 ± 1.64# | 25.20 ± 1.79## |
| (n = 5) | | (100%) | 99.33 ± 1.49 | 98.67 ± 1.83 | 97.33 ± 3.65 | 94.67 ± 5.06* | 90.00 ± 6.67* | 89.33 ± 5.48** | 84.00 ± 5.96** |

TABLE 1.2-continued

The effects of different groups of medicines on different levels of
Acute Myocardiohypoxia (N-ST)

| Group | Dosage/kg | Changing in Percentage before dosage (100%) | After dosage (min) | | | | | | |
|---|---|---|---|---|---|---|---|---|---|
| | | | 15 | 30 | 45 | 60 | 90 | 120 | 180 |
| Dan Shen Pill (n = 5) | 2 g | 30.00 ± 0.00 (100%) | 29.20 ± 1.10 97.33 ± 3.65 | 30.00 ± 0.00 100.00 ± 0.00 | 29.80 ± 0.45 99.33 ± 3.65 | 29.20 ± 1.10 97.33 ± 3.65 | 29.00 ± 1.22 96.67 ± 4.08 | 28.40 ± 1.14# 94.67 ± 3.80 | 27.80 ± 0.45## 92.67 ± 1.49 |

Notes:
Comparison with control group: *P < 0.05 P < 0.01 *P < 0.001
Comparison with situation after dosage: #P < 0.05 ##P < 0.01 ###P < 0.001

TABLE 1.3

The effects of different groups of medicines on different levels of Acute Myocardial hypoxia (N-ST)

| Group | Dosage/kg | Myocardial area/mm2 | Area of Cardiac Chamber/mm2 | Area of Infarction/mm2 | Infarction Location/Heart | Infarction Location/Cardiac Chamber |
|---|---|---|---|---|---|---|
| Normal Saline | 3 ml | 13494.2 ± 1091.4 | 5228.6 ± 646.0 | 1110.05 ± 218.01 | 8.48 ± 0.48 | 20.66 ± 1.99 |
| Ditiazem | 5 mg | 14096.5 ± 3056.4 | 5377.8 ± 411.2 | 378.98 ± 138.41*** | 2.52 ± 1.35*** | 7.22 ± 2.87*** |
| Dan Shen Pill | 2 g | 16186.1 ± 261.3 | 5641.0 ± 365.3 | 407.70 ± 131.42*** | 2.56 ± 0.84*** | 7.82 ± 1.94*** |

Notes:
Comparison with control group:
*P < 0.05
**P < 0.01
***P < 0.001

TABLE 1.4

Effects of different groups of medicines on venous oxygen volume (VO$_2$ ml %)

| Group | Dosage/kg | Before Hypoxia (Normal value) | After Hypoxia (value before dosage Changing Percentage (100%)) | After Dosage (min) | | | | |
|---|---|---|---|---|---|---|---|---|
| | | | | 30 | 60 | 90 | 120 | 180 |
| Normal Saline (n = 5) | 3 ml | 18.52 ± 2.55 | 17.58 ± 1.61 95.89 ± 11.18 | 18.36 ± 2.79 104.41 ± 12.95 | 16.78 ± 2.80 95.28 ± 11.64 | 16.84 ± 3.23 95.50 ± 13.59 | 17.28 ± 2.24 98.47 ± 11.66 | 17.02 ± 2.36 96.78 ± 9.70 |
| Ditiazem (n = 5) | 5 mg | 15.44 ± 2.42 | 16.56 ± 1.61 111.45 ± 33.86 | 16.08 ± 1.13 97.70 ± 10.36 | 15.84 ± 1.43 95.95 ± 8.27 | 15.92 ± 1.29 96.37 ± 5.54 | 15.20 ± 1.50 92.15 ± 9.42 | 14.82 ± 2.28 89.62 ± 11.94 |
| Dan Shen Pill (n = 5) | 2 g | 16.46 ± 3.38 | 17.46 ± 2.69 107.17 ± 8.78 | 17.50 ± 2.58 100.36 ± 3.92 | 16.98 ± 1.94 97.79 ± 5.54 | 15.80 ± 2.01# 90.83 ± 3.67 | 15.60 ± 2.60# 89.37 ± 6.70 | 15.28 ± 2.87# 87.32 ± 7.01 |

Notes:
Comparison with situation before dosage:
P < 0.05
P < 0.01
P < 0.001

TABLE 1.5

Comparison of the effects of different medicines on blood Serum CK (U/L) and LDH (U/L)

| Group | Dosage ml/kg | Before Hypoxia (Normal) | After Hypoxia before Dosage Changing in Percentage (100%) | After dosage (min) 30 | 60 |
|---|---|---|---|---|---|
| CK | | | | | |
| Normal Saline (n = 5) | 3 ml | 310.60 ± 56.08 | 442.40 ± 90.32# | 533.80 ± 89.96# | 644.20 ± 130.96# |
| | | | 144.27 ± 24.29 | 123.19 ± 20.86 | 147.64 ± 25.98 |
| Ditiazen (n = 5) | 5 mg | 316.20 ± 63.04 | 699.60 ± 211.52# | 660.40 ± 184.88 | 737.80 ± 159.04 |
| | | | 219.80 ± 38.93** | 97.20 ± 12.50* | 108.84 ± 20.71* |
| Dan Shen Pill (n = 5) | 2 g | 399.00 ± 25.60 | 546.40 ± 92.88# | 746.60 ± 286.32 | 994.00 ± 357.60 |
| | | | 136.52 ± 21.54 | 133.85 ± 42.37 | 177.26 ± 44.50 |
| LDH | | | | | |
| Normal Saline (n = 5) | 3 ml | 120.00 ± 46.00 | 214.60 ± 54.08# | 214.60 ± 54.08# | 216.60 ± 46.08# |
| | | | 137.36 ± 16.71 | 137.36 ± 16.71 | 140.08 ± 21.23 |
| Diltiazen (n = 5) | 5 mg | 106.40 ± 19.12 | 143.40 ± 28.64 | 143.40 ± 28.64 | 134.40 ± 46.48 |
| | | | 101.14 ± 17.90* | 101.14 ± 17.90* | 92.58 ± 15.17** |
| Dan Shen Pill (n = 5) | 2 g | 131.80 ± 17.04 | 185.20 ± 38.24 | 185.20 ± 38.24 | 193.80 ± 43.76 |
| | | | 90.81 ± 11.17*** | 90.81 ± 11.17*** | 95.19 ± 10.21** |

| Group | After dosage (min) 90 | 120 | 180 |
|---|---|---|---|
| CK | | | |
| Normal Saline (n = 5) | 857.60 ± 262.32# | 960.80 ± 247.68# | 1157.60 ± 180.72## |
| | 191.80 ± 26.52 | 219.41 ± 45.62 | 268.67 ± 35.47 |
| Ditiazen (n = 5) | 820.80 ± 289.76 | 972.40 ± 347.28 | 1238.60 ± 309.12## |
| | 115.31 ± 19.97*** | 314.91 ± 23.35** | 179.51 ± 10.60*** |
| Dan Shen Pill (n = 5) | 944.20 ± 250.16# | 1097.80 ± 268.48# | 1097.40 ± 235.84# |
| | 172.86 ± 40.89 | 197.71 ± 34.95 | 200.03 ± 29.77* |
| LDH | | | |
| Normal Saline (n = 5) | 221.00 ± 64.00# | 221.80 ± 39.36## | 252.80 ± 72.96# |
| | 140.51 ± 13.77 | 145.73 ± 15.56 | 162.51 ± 16.19 |
| Diltiazen (n = 5) | 153.00 ± 70.80 | 194.60 ± 76.72 | 164.80 ± 49.36 |
| | 93.31 ± 19.02** | 121.32 ± 22.12 | 117.24 ± 26.69* |
| Dan Shen Pill (n = 5) | 175.00 ± 31.20 | 195.20 ± 41.04 | 191.80 ± 28.69* |
| | 87.87 ± 15.53*** | 98.96 ± 18.62** | 191.80 ± 28.96 |

Notes:
Comparison with control group:
*P < 0.05
**P < 0.01
***P < 0.001
Comparison with situation before dosage:
P < 0.05
P < 0.01
P < 0.001

TABLE 1.6

Comparison of the effects of different medicines on blood plasma ET (pg/ml) and $TXB_2$ (pg/ml)

| Group | Dosage/kg | Before Hypoxia (Norma) | After Hypoxia before dosage) and Changing in percentage (100%) | After Dosage (min) 30 | After Dosage (min) 60 |
|---|---|---|---|---|---|
| ET | | | | | |
| Normal | 3 ml | 39.47 ± 12.59 | 47.59 ± 5.79 | 61.38 ± 10.66## | 60.70 ± 12.19 |
| (n = 5) | | | 131.40 ± 33.06 | 128.97 ± 13.55 | 127.94 ± 20.07 |
| Diltiazem | 5 mg | 34.41 ± 9.41 | 55.51 ± 3.59 | 47.51 ± 7.39 | 46.38 ± 9.02 |
| (n = 5) | | | 178.30 ± 57.33 | 85.14 ± 13.98** | 84.06 ± 18.24** |
| Dan Shen Pill | 2 g | 50.98 ± 2.53 | 74.98 ± 10.42 | 65.03 ± 14.86 | 76.38 ± 12.16 |
| (n = 5) | | | 146.82 ± 18.13 | 87.34 ± 16.19** | 102.16 ± 10.76* |
| TXB2 | | | | | |
| Normal Saline | 3 ml | 120.00 ± 46.00 | 214.60 ± 54.08# | 214.60 ± 54.08# | 216.60 ± 46.08# |
| (n = 5) | | | 137.36 ± 16.71 | 137.36 ± 16.71 | 140.08 ± 21.23 |
| Diltiazem | 5 mg | 106.40 ± 19.12 | 143.40 ± 28.64 | 143.40 ± 28.64 | 134.40 ± 46.48 |
| (n = 5) | | | 101.14 ± 19.90* | 101.14 ± 17.90* | 92.58 ± 15.17** |
| Dan Shen Pill | 2 g | 131.80 ± 17.04 | 185.20 ± 38.24 | 185.20 ± 38.24 | 193.80 ± 43.76 |
| (n = 5) | | | 90.81 ± 11.17*** | 90.81 ± 11.17*** | 95.19 ± 10.21** |

| Group | After Dosage (min) 90 | After Dosage (min) 120 | After Dosage (min) 180 |
|---|---|---|---|
| ET | | | |
| Normal | 55.40 ± 10.73 | 60.83 ± 6.64# | 67.38 ± 6.37## |
| (n = 5) | 122.34 ± 38.90 | 130.39 ± 21.06 | 143.28 ± 12.27 |
| Diltiazem | 39.97 ± 7.95# | 41.42 ± 15.69 | 45.74 ± 9.40 |
| (n = 5) | 71.69 ± 12.10* | 74.30 ± 17.04** | 82.16 ± 14.09*** |
| Dan Shen Pill | 55.96 ± 5.19# | 69.90 ± 17.26 | 69.39 ± 26.20 |
| (n = 5) | 75.64 ± 6.72* | 93.30 ± 20.94 | 90.15 ± 34.40* |
| TXB2 | | | |
| Normal Saline | 1511.9 ± 252.2 | 1164.9 ± 223.0 | 1268.1 ± 154.8 |
| (n = 5) | 114.06 ± 8.07 | 116.22 ± 8.09 | 134.90 ± 31.09 |
| Diltiazem | 1093.4 ± 320.9 | 1284.1 ± 695.0 | 1032.7 ± 343.1 |
| (n = 5) | 69.72 ± 8.76*** | 63.03 ± 14.20*** | 62.77 ± 14.51* |
| Dan Shen Pill | 938.7 ± 46.4 | 883.6 ± 107.7## | 902.6 ± 118.3# |
| (n = 5) | 90.11 ± 14.32 | 83.00 ± 3.65*** | 84.67 ± 5.80** |

Notes:
Comparsion with control group:
*P < 0.05
**P < 0.01
***P < 0.001
Comparison with situation before dosage:
P < 0.05
P < 0.01
P < 0.001

TABLE 1.7

Comparison of the effects of different medicines on 6-Keto-$PGF_{1\alpha}$ and 6-Keto-$PGF_{1\alpha}$/$TXB_2$

| Group | Dosage/ kg | Before hypoxia (Normal value | After Hypoxia before dosage and Changing in percentage (100%) | After dosage (min) 30 | 60 |
|---|---|---|---|---|---|
| 6-Keto-$PGF_{1\alpha}$ | | | | | |
| Normal Saline (n = 5) | 3 ml | 1673.2 ± 221.0 | 1469.0 ± 283.6# | 1200.6 ± 335.3# | 1099.2 ± 301.0### |
|  |  |  | 87.15 ± 7.49 | 80.77 ± 10.26 | 73.79 ± 6.64 |
| Diltiazem (n = 5) | 5 mg | 1597.4 ± 185.3 | 1478.8 ± 218.6 | 1749.4 ± 278.3 | 1902.6 ± 155.1# |
|  |  |  | 92.3 ± 5.53 | 118.95 ± 14.47** | 131.19 ± 16.98*** |
| Dan Shen Pill (n = 5) | 2 g | 1763.0 ± 361.6 | 1417.4 ± 365.5# | 1471.6 ± 365.5# | 1649.4 ± 280.7 |
|  |  |  | 80.76 ± 6.68 | 100.50 ± 20.80 | 132.71 ± 51.64* |
| 6-Keto-$PGF_{1\alpha}$/$TXB_2$ | | | | | |
| Normal Saline (n = 5) | 3 ml | 120.00 ± 46.00 | 214.60 ± 54.08# | 1.174 ± 0.383# | 1.037 ± 0.381# |
|  |  |  | 137.36 ± 16.71 | 73.30 ± 4.14 | 65.57 ± 8.52 |
| Diltiazen (n = 5) | 5 mg | 106.40 ± 19.12 | 143.40 ± 28.64 | 1.507 ± 0.505## | 1.501 ± 0.358# |
|  |  |  | 101.14 ± 17.90* | 148.42 ± 17.35*** | 155.44 ± 28.97*** |
| Dan Shen Pill (n = 5) | 2 g | 131.80 ± 17.04 | 185.20 ± 38.24 | 1.523 ± 0.441 | 1.764 ± 0.270 |
|  |  |  | 90.81 ± 11.17*** | 108.02 ± 21.11** | 158.76 ± 77.62* |

| Group | After dosage (min) 90 | 120 | 180 |
|---|---|---|---|
| 6-Keto-$PGF_{1\alpha}$ | | | |
| Normal Saline (n = 5) | 1056.2 ± 210.2## | 1095.0 ± 215.2# | 1052.8 ± 187.7## |
|  | 72.39 ± 5.92 | 75.39 ± 8.57 | 72.29 ± 7.21 |
| Diltiazem (n = 5) | 1912.4 ± 258.5 | 1982.8 ± 574.2 | 1705.2 ± 412.2 |
|  | 132.75 ± 28.52** | 139.39 ± 56.36* | 119.08 ± 39.78 |
| Dan Shen Pill (n = 5) | 1557.2 ± 251.0 | 1138.2 ± 124.6 | 1202.6 ± 270.3 |
|  | 129.31 ± 61.64 | 88.35 ± 25.15 | 90.26 ± 21.03 |
| 6-Keto-$PGF_{1\alpha}$/$TXB_2$ | | | |
| Normal Saline (n = 5) | 1.037 ± 0.381# | 1.040 ± 0.368# | 0.852 ± 0.218 |
|  | 65.67 ± 11.87 | 65.67 ± 11.87 | 57.95 ± 11.77 |
| Diltiazen (n = 5) | 1.980 ± 0.924 | 1.980 ± 0.924 | 1.801 ± 0.596 |
|  | 203.82 ± 83.25** | 203.82 ± 83.25** | 198.48 ± 87.02** |
| Dan Shen Pill (n = 5) | 1.320 ± 0.254 | 1.320 ± 0.254 | 1.388 ± 0.388 |
|  | 105.35 ± 25.55* | 105.35 ± 25.55* | 105.05 ± 19.85** |

Notes:
Comparison with control group:
*$P < 0.05$
**$P < 0.01$
***$P < 0.001$
Comparison with situation before dosage:
$P < 0.05$
$P < 0.01$
$P < 0.001$ 2. The Protection of Myocardial Ischemical Reperfusion Injury from Hypoxia in Rats This research stresses the effects of Dan Shen Pill in myocardial ischemical reperfusion injury from hypoxia in rats, especially on the apoptosis of myocardial cells.

1. Animal Models. Wistars are male rats. They were given anesthesia, and their chests were opened while they continued breathing. The coronary artery was tied at the conical area between the left atrium and the pulmonary artery.

2. Methods. The rats were assigned to 5 random groups: a) Sham-operated control. Perfuse the normal saline to the stomach, 1 ml/day, 4 days in total. b) Myocardial ischemia reperfusion (M-IR). The same reperfusion method as above. c) Dissolve the compound Dan Shen Pill I (DSPI) 150 ml/kg/day in 1 ml of normal saline. Infuse the stomach (the same method as above). d) Dan Shen Pill II (DSPII), 300 ml/kg/day. The other specifications are the same as those used with DSP I. e) Dan Shen Pill (DSPIII), 450 ml/kg/day. The other specifications are the same as those used with DSPI.

Testing Standard:

2.1 Testing of myocardial infarction area. The left coronary artery was retied before the rat died. The auricles were removed after priming with 1% of Evan's Blue and bleached with PBS. They were kept in ice for 1 h. After removing the unnecessary cells, they were colored in 1% TTC for 30 min (37° C.). The myocardial hypoxia emergency area (Uncolored Evan's blue Area) and infarction area (Uncolored TTC Area) were calculated by weighing.

2.2 Testing and analysis of in-situ labeling of myocardial apoptotic cells. 3 slices of flesh were taken from 3 different parts of each of the hearts. The 3'-OH end of DNA in the nuclei of the myocardial apoptotic cells was labeled with nicked-end TdT isomerase by TdT-mediate flourescein-duTP nick-end labeling, TUNEL. 5 different views were chosen. 300 positive cells inside the myocardial cells in each view were counted. The average positive cell count percentage was used as the apoptotic index, AI.

Results

Change in myocardial infarction area. Myocardial infarction did not occur after 7 hrs of sham operation. Myocardial hypoxia occurred for 1 hr and myocardial infarction occurred sharply after reperfusing for 6 hrs. DSP can reduce the M-IR area and increase the effects with increasing dosage. Myocardial infarction area was minimized as shown in the following Table 2.1.

TABLE 2.1

Changes of myocardial infarction area in different groups

| Group | Infarction Area weight/ left ventricle weight (%) | Infarction Area weight/ risty Area weight (%) |
|---|---|---|
| Sham-control | 0 | 0 |
| M-IR | 41.8 ± 7.9 | 63.2 ± 8.6 |
| DSPI | 34.6 ± 7.2**□ | 55.7 ± 8.4* |
| DSPII | 27.1 ± 6.5**□ | 47.3 ± 7.7**□ |
| DSPIII | 19.4 ± 6.1**□□□ | 38.9 ± 7.5**□□□ |

Notes:
Comparison with M-IR group, *$P < 0.05$, **$P < 0.01$;
Comparison with DSP I group, $^\Delta P < 0.05$, $^{\Delta\Delta} P < 0.01$;
Comparison with DSPII group, $^\diamond P < 0.05$.

3.2 Change in myocardial apoptotic cells. Comparatively large amounts of DSP can sharply reduce the number of M-IR apoptotic cells, and AI drops with increasing dosage of DSP, as shown in Table 2.2.

TABLE 2.2

Change in number of different groups of myocardial apoptotic cells

| Group | Case number | Myocardial cells AI (%) |
|---|---|---|
| Sham-control | 10 | 0.82 ± 0.47 |
| M-IR | 10 | 22.76 ± 13.17 |
| DSPI | 10 | 20.93 ± 13.25* |
| DSPII | 10 | 16.28 ± 11.96*$^{\Delta\diamond}$ |
| DSPIII | 10 | 10.75 ± 9.44$^{\Delta\Delta\diamond}$▲ |

Notes:
Comparison with Sham-control group, *$P < 0.01$;
Comparison with M-IR group, □$P < 0.05$, □□$P < 0.01$;
Comparison with DSPI group, $P < 0.05$, $^{\diamond\diamond} P < 0.01$;
Comparison with DSPII group, ▲$P < 0.05$ Conclusion This research proves that DSP could sharply minimize the myocardial infarction area in the M-IR group of rats. This further shows that DSP can do a good job of protecting the myocardial cells of the M-IR group.

3. Propagation of Myocardial Hypoxia in Mice and Effects of Fas/FasL Proteins under Deoxygenation and Deoxygenation/Re-Oxygenation Conditions.

Fas gene is an apoptosis-stimulating gene. Its expressed protein product, Fas antigen, is a cell membrane protein. Recently, it was discovered, in experiments on propagation of myocardial hypoxia, that there is a close relationship between the expressed mRNA of Fas gene and myocardial apoptosis. FasL is the ligand of Fas. It is on the surface of transmembrane proteins, which is homologous to the TNF. It can bind to the receptor Fas on the surface of the cell and give out the death signal.

1. Method. The myocardial cells of newborn mice were propagated normally. Hypoxia and deoxygenation/re-oxygenation testing was carried out after 24 hrs of propagation. The change in Fas/FasL protein expression level was then tested by the secondary immune system.

2. Results

1. Change in Fas/FasL protein expression in the group with hypoxia for 4.5 hrs, group with hypoxia for 30 mins, and group with re-oxygenation for 4 hrs. The Fas/FasL protein expressions of both groups increased sharply compared with the control one. Protein expression of the Fas/FasL of DSP-protected group dropped more dramatically than the unprotected one, as shown in Table 3.1.

2. Change in Fas/FasL protein expression in the group with hypoxia for 10.5 hrs, group with hypoxia for 30 mins, and group with re-oxygenation for 10 hrs. The Fas/FasL protein expressions of both groups increased sharply compared with the control. The protein expression of the Fas/FasL of the DSP-protected group dropped more dramatically than the unprotected one, as shown in Table 3.2.

3. There is more likelyan increasing trend to the Fas/FasL protein expression in the group with hypoxia for 10.5 hrs than in the group with hypoxia for 4.5 hrs, but there is no major difference between them.

4. There was no major difference between the group with re-oxygenation for 10.5 hrs and the group with re-oxygenation for 4.5 hours.

5. There was a correlation in the protein expression of Fas/FasL.

The above results show DSP can reduce apoptosis by interfering with Fas/FasL expression, protecting the cells from damage by hypoxia and deoxygenation/re-oxygenation.

TABLE 3.1

The change in Fas/FasL protein expression in
group with hypoxia for 4.5 h, group with hypoxia
for 30 mins, re-oxygenation for 4 hrs.

| | Fas protein PEI (%) | | FasL protein PEI (%) | |
|---|---|---|---|---|
| | unprotected | DSP protected | unprotected | DSP protected |
| Control group | 2.59 | 2.61 | 2.27 | 2.26 |
| Group with hypoxia for 4.5 hrs | 18.01* | 9.62** | 19.67* | 10.74** |
| Group with Re-oxygenation for 4 hrs | 19.02* | 10.00** | 20.71* | 10.69** |

Notes:
Comparison with control group, *P < 0.05
Comparison with DSP unprotected group, **P < 0.05

TABLE 3.2

The change of Fas/FasL protein expression in the
group with hypoxia for 10.5 hrs, group with hypoxia
for 30 mins, re-oxygenation for 1O hrs.

| | Fas Protein PEI (%) | | FasL Protein PEI (%) | |
|---|---|---|---|---|
| | unprotected | DSP protected | unprotected | DSP protected |
| Control group | 2.89 | 2.22 | 2.22 | 2.11 |
| Group with hypoxia for 10.5 hrs | 21.75* | 11.64** | 22.83* | 14.20** |
| Group with re-oxygenation for 10 hrs | 19.70* | 12.95** | 22.12* | 13.08** |

Notes:
Comparison with control group *P < 0.05, Comparison with DSP unprotected group **P < 0.05

4. Effects on Lipidemia and Atherosclerosis in Rabbits

1. Method 1.1 Experimental Groups. (1) Normal control group (8 rabbits) normal feeding; (2) High-fats group: High-fats feeding. All were fed for 4 weeks. Weight and lipoprotein in the blood were measured. The high-fats group was divided into 4 sub-groups (12 rabbits in each sub-group). 1. High-fats control group, 2. High-dosage of DSP group (4 g dosage/kg/day), 3. Low-dosage DSP group (2 g dosage/kg/day), and 4. Simvastatin group (1 mg/kg/day). All are given distilled water except those with special prescriptions and ends after 12 weeks testing.

1.2 Experimental Methods and Standards. (1) Examination of Aortic Lesion. Drugs were given to the animals for 8 weeks, and then the animals were killed. The aortas were removed and the unnecessary membranes and fats discarded. The aortas were cut open along the mid line. One-fifth of the aorta was removed for lipid examination. The remaining part was colored by Sudan III and used to calculate the spotting plate area and the total area of the aorta. The percentage of the lesion part was calculated, and a grading was given. The aorta was positionally cut to make paraffin slices. It was colored by HE. The average thickness of the interior membrane spot plates was measured by microscopic parameter. (2) Examination of coronary artery lesion. The lower 0.4 cm of the coronary artery colpus and 0.8 cm of the apex cordis were transected to make 3 small plates. Sudan III colorization was carried out. The number of blood vessels with spot plates in the coronary artery and the lesion percentage (lesion percentage=the number of blood vessels with lesion/the total number of blood vessels in each transect X100%) were observed, calculated and graded according to the blocking of the blood vessels with spot plates. The average points were calculated by accumulation.

Results (1) Effects on lipoprotein in blood serum of rabbits. The testing showed that the markings are lower than that of the high-fats group 2, 4, 8 weeks after taking DSP, as shown in Table 4.1.

(2) Aorta AS area. It was observed that the interior membrane of the aorta was smooth and shiny without AS spot plates or streaks. The aortic lesion area percentage of the group with DSP protection was obviously smaller than that of the high-fats group (P<0.05). Lipoprotein level in aorta. Drugs were given for 8 weeks. The aortic TC and TG in the high-fats control group were obviously higher than that in the normal control group (P<0.001). TC in the DSP-protected group was obviously higher than that in the high-fats control group, as shown in Table 4.2.

(3) Effects on liver coefficient and lipoprotein level in the liver. The testing showed that the DSP-protected group and high-fats control group ratio can lower TG content (P<0.05), as shown in Table 4.3.

Conclusion

The testing showed that DSP can lower TC, TG, LDL-C, VLDL-C concentration, and TC/HDL-C ratio in the blood serum in rabbits. DSP also reduced the thickness of the aortic spot plate and the area of the aortic spot plates. DSP could adjust lipoprotein level and prevent atherosclerosis to a certain extent.

TABLE 4.1

Effects on the lipoprotein content in blood serum of rabbits (mmol/L, n = 8, x ± s)

| Time | Group | Dosage | TC | LDC-C | VLDC-C | TC/HDL-C | TG |
|---|---|---|---|---|---|---|---|
| B/f testing | Normal control | | 2.23 ± 0.19 | 0.79 ± 0.20 | 0.41 ± 0.20 | 2.25 ± 0.59 | 0.74 ± 0.17 |
| | Highfat control | | 2.31 ± 0.22 | 0.94 ± 0.16 | 0.42 ± 0.24 | 2.58 ± 0.80 | 0.74 ± 0.21 |
| | DSP | 4 g | 2.26 ± 0.14 | 0.91 ± 0.14 | 0.50 ± 0.19 | 2.75 ± 0.59 | 0.81 ± 0.18 |
| | DSP | 2 g | 2.21 ± 0.19 | 0.84 ± 0.17 | 0.40 ± 0.12 | 2.30 ± 0.29 | 0.78 ± 0.30 |
| | Simvastatin | 1 mg | 2.27 ± 0.18 | 0.87 ± 0.21 | 0.51 ± 0.27 | 2.72 ± 0.85 | 0.72 ± 0.15 |
| A/fter dosage | Normal Control | | 2.19 ± 0.20*** | 0.87 ± 0.20*** | 0.45 ± 0.12*** | 2.51 ± 0.30*** | 0.83 ± 0.21** |
| | Highfat control | | 26.69 ± 3.86 | 19.40 ± 4.19 | 6.42 ± 2.31 | 31.17 ± 9.49 | 2.25 ± 1.03 |
| | DSP | 4 g | 27.48 ± 6.83 | 20.25 ± 6.80 | 6.34 ± 2.57 | 32.07 ± 9.70 | 2.10 ± 0.74 |

TABLE 4.1-continued

Effects on the lipoprotein content in blood serum of rabbits (mmol/L, n = 8, x ± s)

| Time | Group | Dosage | TC | LDC-C | VLDC-C | TC/HDL-C | TG |
|---|---|---|---|---|---|---|---|
| | DSP | 2 g | 28.43 ± 5.46 | 20.77 ± 6.55 | 6.84 ± 2.28 | 36.51 ± 12.31 | 2.25 ± 0.86 |
| | Simvastatin | 1 mg | 26.92 ± 7.72 | 19.69 ± 8.33 | 6.35 ± 1.42 | 31.68 ± 10.14 | 2.04 ± 1.00 |
| 2 weeks after dosage | Normal control | | 2.15 ± 0.34*** | 0.88 ± 0.22*** | 0.37 ± 0.14*** | 2.43 ± 0.42*** | 0.74 ± 0.10*** |
| | Highfat Control | | 34.15 ± 6.97 | 26.66 ± 6.21 | 6.65 ± 1.40 | 43.02 ± 11.38 | 3.01 ± 0.84 |
| | DSP | 4 g | 24.81 ± 6.94* | 16.54 ± 6.99** | 7.39 ± 1.93 | 29.62 ± 11.16* | 1.60 ± 0.56** |
| | DSP | 2 g | 31.74 ± 7.91 | 25.27 ± 7.45 | 5.66 ± 1.70 | 39.31 ± 7.23 | 2.12 ± 0.91 |
| | Simvastatin | 1 mg | 27.06 ± 4.46* | 19.54 ± 5.71* | 6.66 ± 1.65 | 32.29 ± 7.39* | 1.85 ± 0.55** |
| 4 weeks after dosage | Normal Control | | 2.30 ± 0.20*** | 0.97 ± 0.30*** | 0.38 ± 0.19*** | 2.48 ± 0.41*** | 0.78 ± 0.17*** |
| | Highfat control | | 37.87 ± 6.92 | 27.73 ± 7.19 | 9.06 ± 2.30 | 35.95 ± 9.19 | 2.84 ± 0.71 |
| | DSP | 4 g | 25.96 ± 5.64** | 18.06 ± 6.02* | 6.72 ± 1.46* | 22.19 ± 5.07** | 1.74 ± 0.39** |
| | DSP | 2 g | 35.46 ± 8.86 | 27.41 ± 8.17 | 6.94 ± 1.17* | 32.56 ± 8.52 | 2.34 ± 0.33 |
| | Simvastatin | 1 mg | 26.1 ± 3.03*** | 18.22 ± 3.37** | 6.54 ± 0.74* | 19.6 ± 4.38*** | 1.80 ± 0.31** |
| 8 weeks after dosage | Normal Control | | 2.06 ± 0.26*** | 0.64 ± 0.44*** | .044 ± 0.28*** | 2.14 ± 0.41*** | 0.80 ± 0.27*** |
| | High Fat Control | | 46.19 ± 8.26 | 32.04 ± 9.69 | 13.37 ± 3.51 | 64.27 ± 21.3 | 4.34 ± 1.45 |
| | DSP | 4 g | 27.8 ± 7.99*** | 19.35 ± 8.05* | 7.44 ± 2.17** | 26.9 ± 10.76** | 2.73 ± 0.75* |
| | DSP | 2 g | 32.47 ± 4.73** | 22.59 ± 4.94* | 8.91 ± 2.17** | 35.8 ± 11.72** | 3.67 ± 0.88 |
| | Simvastatin | 1 mg | 26.3 ± 4.40*** | 17.78 ± 5.69** | 7.30 ± 2.05*** | 22.3 ± 6.54*** | 2.70 ± 0.77* |

Notes:
Comparison with high-fats control group
*P < 0.05,
**P < 0.01,
***P < 0.001

TABLE 4.2

Effects on lipoprotein content in aorta

| Group | Dosage (/kg/Day) | Number of animal (n) | TC |
|---|---|---|---|
| Normal Control | | 8 | 0.51 ± 0.08*** |
| High-fats Control | | 8 | 7.80 ± 2.07 |
| DSP | 4 g | 8 | 5.30 ± 1.62* |
| DSP | 2 g | 8 | 5.51 ± 1.86* |
| Simvastatin | 1 mg | 8 | 4.93 ± 2.62* |

Notes:
Comparison with high-fats control group
*P < 0.05,
***P < 0.001

TABLE 4.3

Effects on hepatocytic tissue TG and liver coefficient

| Group | Dosage (/kg) | TG (mg/tissue organ) | Liver Coefficient (g/100 g weight) |
|---|---|---|---|
| Normal Control | | 5.50 ± 1.05* | 2.83 ± 0.36*** |
| High-fats Control | | 9.70 ± 1.69 | 5.57 ± 0.78 |
| DSP | 4 g | 7.38 ± 1.67* | 5.08 ± 0.77 |
| DSP | 2 g | 8.76 ± 0.86 | 5.80 ± 1.16 |
| Simvastatin | 1 mg | 7.44 ± 1.49* | 5.16 ± 0.60 |

Notes: Comparison with high-fats control group *P < 0.05, ***P < 0.001

5. Anti-Oxidation and Removal of Free Radicals

Effects on MDA and SOA in the blood serum on M-IR damage By comparing the effect of Diltiazem and the effects of DSP on M-IR and its correlated biochemical markers, MDA and SOD can be observed.

1. Method:

(1) Experimental Groups. Control group (Serum taken as normal control), Model group (Normal Saline), Ditiazem group (30 mg/kg), DSP 6.0, 3.0 g/kg group. Each group was diluted to its necessary concentration with 3 ml/kg normal saline through the duodenum.

(2) Experimental Method. Wistar animal is anesthetized by pentobarbital sodium and fixed. Chests and cardial membranes are opened to expose the heart. A hole in the left lower dorsal part of the coronary artery is left for tying. Separate the duodenum, and infuse the tested drugs into it. Take blood from the abdomen after 2 hrs and test the MDA and SOD content in the blood serum.

Results

The SOD activity of DSP group increased. There was an obvious difference when compared with the control group (P<0.01), but the effects on MDA could not yet be observed, as shown in Table 5.1.

TABLE 5.1

Effects of DSP on SOD activity and MDA content in blood serum

| Group | Dosage | SOD (U/ml) | MDA ($\mu$ mol/L) × $10^{-3}$ |
|---|---|---|---|
| Normal control | | 830.8 ± 31.9 | 2.60 ± 0.35 |
| Model | | 627.7 ± 70.9## | 5.42 ± 0.97## |
| Ditiazem | 30 mg | 817.6 ± 115.6** | 5.29 ± 1.07 |
| DSP | 3.0 g/kg | 801.7 ± 74.6** | 5.83 ± 1.24 |
| | 6.0 g/kg | 794.2 ± 122.6** | 5.43 ± 1.06 |

Notes:
Comparison with normal control group, P < 0.01;
**Comparison with model group, P < 0.01.

Conclusion

DSP provides protection from injuries caused by reperfusion of ischemic area and increases the activity of SOD.

Effects on SOD Activity and MDA Content in Rabbit Blood Serum and Liver

Method. The experimental groups were divided into: (1) Normal control group. Normal feeding; (2) High-fats feeding group: high-fats feeding.

All were fed for 4 weeks. weight and lipoprotein content in the blood were measured. The high-fats feeding group was divided into 4 sub-groups: a) High-fats control group, b) High-dosage DSP group (4 g raw medicine/kg/day), c) Low-dosage DSP group (2 g raw medicine/kg/day), d) Simvastatin group (1 mg/kg/day). Medicine was given to the rabbits through the stomach, according to prescription. The same volume of distilled water was given to the normal control group and high-fats feeding group. Testing ended after 12 weeks.

Results (1) Measurement of blood serum MDA and SOD showed that the MDA content of the high-fats feeding group was much higher than that of the normal control group after 8 weeks of treatment ($P<0.01$). However, there is no significant SOD activity difference compared with that of the normal control group. No significant differences can be found in SOD activity and MDA content between the high-fats control group and each of the medicated-given groups.

(2) Measurement of MDA and SOD in liver shows that the MDA content of the high-fats feeding group is much higher than that of the normal control group after 8 weeks of treatment ($P<0.001$). SOD activity was much lower than that of the normal control group ($P<0.001$). The liver MDA contents of both the high-dosage DSP group and the Simvastatin group were much lower than that of the high-fats control group ($P<0.001$). SOD activity of each of the medicated groups was much higher than that of the high-fats control group ($P<0.01$), as shown in Table 5.2.

dation standard, and reduce the level of damage to the organs.

6. Effects on Cardiac Arrhythmia Caused by Exogenous Free Radicals

Langendorff perfusion device was used to pour ferrous sulfate (0.25 mmol/L)/citrate (1.0 mmol/L) into the Wistar rat's artificial heart. The model of free radicals causing heart rhythm irregularity was replicated to observe the effects of DSP.

1. Experimental Groups (1) Blank group (Normal control). Reperfused with perfusion solution for 45 mins continuously. The change in electrocardiographic pattern was observed.

(2) SP group. DSP was added in 50 mg/L of perfusion solution and perfused for 45 mins continuously. The change in electrocardiographic pattern was observed.

(3) Free-radical-damaging group (Free radicals). After pre-perfusing the artificial heart for 15 mins, it was reperfused with perfusion solution containing ferrous sulfate (0.25 mmol/L)/citrate (1.0 mmol/L) for 30 mins continuously. The change in electrocardiographic pattern was observed.

(4) DSP-protected group (DSP+free radicals): DSP was added into 50 mg/L of perfusion solution and pre-perfused for 15 mins. Ferrous sulfate (0.25 mmol/L/citrate (1.0 mmol/L) was added to the perfusion solution and then infuse for 30 mins continuously. The change in electrocardiographic pattern was observed.

(5) Verapamil-protected group (verapamil+free radicals). 1 ml/L of verapamil was added to the perfusion solution and preperfused for 15 mins. Ferrous sulfate (0.25 mmol/L)/citrate (1.0 mmol/L) was added to the priming solution and perfused for 30 mins continuously. The change in electrocardiographic pattern was observed.

TABLE 5.2

Effects of DSP on SOD activity and MDA content on rabbit liver ($x \pm s$)

| | | | Blood serum | | Liver | |
| --- | --- | --- | --- | --- | --- | --- |
| Group | Dosage (/kg/d) | n | SOD (u/ml) | MDA (nmol/ml) | SOD ($10^3$ u/g tissue weight) | MDA ($10^3$ u/g tissue weight) |
| Normal Control | | 8 | 776.9 ± 72.8 | 2.73 ± 0.42** | 12.85 ± 0.50*** | 189.1 ± 30.0** |
| High-fats control | | 8 | 754.7 ± 44.2 | 6.82 ± 3.54 | 9.87 ± 0.98 | 387.3 ± 38.3 |
| DSP | 4 g raw medicine | 8 | 781.7 ± 152.3 | 6.24 ± 3.22 | 11.67** ± 0.82 | 256.3 ± 20.0*** |
| | 2 g raw medicine | 8 | 772.4 ± 84.8 | 6.24 ± 2.16 | 11.37 ± 0.59** | 325.7 ± 119.9 |
| Simvastatin | 1 mg | 8 | 816.7 ± 77.2 | 5.63 ± 1.30 | 11.62 ± 0.38*** | 249.3 ± 42.6*** |

Notes:
Comparison with high-fats control group,
**$P < 0.01$
***$P < 0.001$

MDA is the main catabolic product of the oxidation of fats. It can damage the structure of the cell membrane so seriously that heart and liver tissues are damaged. SOD has an effective action of clearance on superoxide anions. It can regulate the oxidation reaction controlled by free radicals. DSP can increase SOD activity, decrease MDA content, lower the oxi- Results Exogenous free radicals can increase cardiac arrhythmia up to 100% and atrial cellular lysis up to 43%. 1 mg/L verapamil and 50 mg/L DSP can lower the irregularity percentage to 71.4% and 87.5%, as shown in Table 6.1. It shows that DSP can prevent cardiac arrhythmia caused by free radicals.

TABLE 6.1

Effects of DSP on cardiac arrhythmia caused by exogenous free radicals

| Group | Case number | Atrioventricular dissociation | | Ventricular extrasystole | | Ventricular overspeed | | Ventria-fibrillation | | Total cardiac arrhythmia | |
|---|---|---|---|---|---|---|---|---|---|---|---|
| | | Case number | % | Case number | % | Case number | % | Case number | % | Case number | % |
| Normal Control | 7 | 0 | 0 | 0 | 0 | 0 | 0 | 0 | 0 | 0 | 0 |
| DSP | 7 | 0 | 0 | 0 | 0 | 0 | 0 | 0 | 0 | 0 | 0 |
| Free radicals | 7 | 5 | 71.4 | 5 | 71.4 | 3 | 42.7 | 3 | 42.7 | 7 | 100 |
| Verapamil + Free radicals | 6 | 0 | 0 | 1 | 16.6 | 1 | 16.6 | 0 | 0 | 2* | 33.3 |
| DSP + Free radicals | 8 | 1 | 12.5 | 0 | 0 | 0 | 0 | 0 | 0 | 1** | 12.5 |

Notes:
Comparison with free-radical group,
*P < 0.05
**P < 0.001

7. Clinical Applications for Acute Pancreatitis in Rats

This experiment uses the acute pancreatitis model with multi-organ malfunction in rats to show the change in the blood plasma endothelins and the clinical applications of DSP.

1. Experimental Groups

Classical reverse bile duct vaccination was used to create the acute pancreatitis model. The animal used was a Wistar Rat.

(1) Normal control group (Control group): The bile duct was not tied. The abdomen was cut open and immediately closed after the pancreas was removed. Normal saline (5 ml/kg) was injected subcutaneously 30 mins before the operation and 2 hrs after operation. Animals were killed 12 hrs after operation.
(2) Saline treatment group (Saline group): Normal saline (5 ml/kg) was injected subsutaneously 30 mins before the model was created and 2 hrs after creation. Animals were killed 12 hrs after the model was created.
(3) DSP treatment group (DSP group): DSP (400 mg/kg) was reperfused into the stomach 30 mins before the model was created and 2 hrs after creation. Animals were killed 12 hrs after the model was created.

2. Results

Glutamate Phosphate Transferase (GPT), Bilirubin Urea Nitrate (BUN) and Amylase (Amg) content in the blood serum of the saline group increased significantly (compared with the normal control group, P<0.01). GPT, BUN, and Amg content in the DSP group increased (compared with the normal control group, P<0.01), but was still lower than that of the saline group (compared with saline group, P<0.01), as shown in Table 7.1. The endothelins (ET) content of the saline group increased significantly (Compared with normal control group, P<0.001). The ET content of DSP group was much lower than that of the saline group (P<0.05) and the normal control group P>0.05, as shown in Table 7.2. Microscopic observation of the change in shape of pancreatic, liver and lung tissue showed that there was much more improvement in the DSP group than in the saline group.

TABLE 7.1

The change in GPT (u/l), BUN (mmol/L), Amg (u) content in each group

| | Control group | Saline group | DSP group |
|---|---|---|---|
| GPT | 48.89 ± 10.84 | 1162.48 ± 258.90** | 612.13 ± 155.50**## |
| BUN | 9.04 ± 1.47 | 27.43 ± 2.61* | 19.74 ± 3.23*# |
| Amg | 4880 ± 1850.07 | 11970.7 ± 1530.65* | 9458.4 ± 782.32*# |

Notes: Comparison with control group,
*p < 0.01
**p < 0.001
Comparison with saline group,
P < 0.01
P < 0.001

TABLE 7.2

Change in blood plasma ET (pg/mg) content in each group

| | Control group | Saline group | DSP group |
|---|---|---|---|
| ET | 149.091 ± 19.537 | 247.096 ± 116** | 149.291 ± 41.865*# |

Notes: Comparison with control group, *p > 0.05 **p < 0.001 Comparison with saline group, #P < 0.05

The above experiment shows that blood plasma ET content increases significantly in acute pancreatitis with malfunction of multiple organs. Blood plasma ET content decreases significantly after DSP treatment, and treatment can greatly improve liver, kidney and pancreas function.

8. Prevention of Platelet Aggregation and Thrombosis

1. Effects on platelet aggregation in rats. Male rats weighing about 300 g were anesthetized with 3% pentobarbital sodium i.p. 1 ml of blood were collected from the carotid artery and centrifuged. Platelet Rich Plasma (PRP) and Platelet Poor Plasma (PPP) were collected. ADP was added into PRP, and platelet aggregation percentage was tested after 5 mins, as shown in Table 8.1.

TABLE 8.1

Effects of ADP on platelet aggregation

| Group | Dosage (g/kg) | Case | Average aggregation percentage (X ± SD) | Aggregation inhibition % |
|---|---|---|---|---|
| Control group | Standard solution | 31 | 66.74 ± 2.04 | |
| DSP | 0.4 | 14 | 35.09 ± 2.55 | 48.12 |
| Tongmailing | 0.2 | 10 | 53.10 ± 2.75 | 21.74 |
| Xuesaitong | 0.4 | 11 | 48.29 ± 5.5 | 24.54 |

3. Effects on experimental thrombosis in rats. The Umetsu method is used to carry out the experiment. The results in Table 8.2 show that high-dosage DSP (100 mg/kg) can significantly control thrombosis, and low-dosage DSP (50 mg/kg) gives no significant effects.

TABLE 8.2

Effects on experimental thrombo-formation in rats

| Group | Dosage (g/kg) | Case | Average aggregation percentage (X ± SD) | Inhibition % |
|---|---|---|---|---|
| Control | Normal saline | 10 | 21.8 ± 2.4 | |
| Aspirin | 30 | 10 | 10.6 ± 2.1* | 49.2 |
| DSP | 50 | 10 | 21.2 ± 2.9 | 6.5 |
| | 100 | 10 | 11.7 ± 2.6* | 44.8 |

Notes:
Comparison with normal control group, *P < 0.01

5. Effects on cAMP content in rabbit blood platelets. cAMP content is tested by radioimmunoassay. Protein content is measured by the Hartree Method. The results in Table 8.3 show that cAMP content in blood platelets in the high-dosage (100 mg/kg) DSP group increased more significantly than in the control group. The low-dosage group (50 mg/kg) showed no significant effects.

TABLE 8.3

Effects on cAMP content in rabbit platelets (X ± SD)

| Group | Dosage (mg/kg) | Case (cAMP) | Protein (Pmol/mg) |
|---|---|---|---|
| Control | Normal Saline | 15 | 6.2 ± 2.1 |
| Aminophylline | 0.6 | 20 | 15.4 ± 3.9* |
| DSP | 1.0 | 20 | 8.7 ± 3.2 |
| | 2.0 | 10 | 13.6 ± 2.5* |

Notes:
Comparison with control group *P < 0.01

6. Effects on cAMP content in rat blood plasma. Blood cAMP content was tested by radioimmunoassay. The results show as table 8.4 that compared with the normal control group, blood plasma cAMP content 30 mins and 60 mins after treatment increased in the high-dosage DSP group (100 mg/kg). The low-dosage DSP (50 mg/kg) group showed no significant effects.

TABLE 8.4

Effects on blood plasma cAMP content (X ± SD)

| Group | dosage (mg/kg) | Number of animals | cAMP content 30 min after treatment | (Pmol/ml plasma) 60 min after treatment |
|---|---|---|---|---|
| Control | Normal saline | 10 | 11.8 ± 3.6 | 11.4 ± 3.2 |
| Aminophylline | 30 | 10 | 20.7 ± 3.2 | 21.1 ± 3.8 |
| DSP | 50 | 10 | 13.4 ± 4.1 | 13.3 ± 3.3 |
| | 100 | 10 | 18.4 ± 2.9 | 17.6 ± 3.1 |

Notes:
Comparison with normal control group at the same times, *P < 0.01

Conclusion

The increasing of cAMP inhibits the activity of phosphoesterase and epoxidase, and reduces the production of prostaglandin peroxide. It can also activate protease to phosphoesterize the membrane protein, alter the effects of membrane protein composition on platelet aggregation, and control platelet aggregation to prevent thrombosis. DSP can increase blood platelet concentration and plasma camp content in order to prevent thrombosis.

9. Effects of DSP on Blood Vessels and Nerve Lesion in Diabetic Rats

Method. 38 SD rats are divided into normal control group, model group and DSP group, at random. The diabetic rat model is made by abdominally injecting STZ60 mg/kg. DSP ($0.25/kg \cdot d^{-1}$) was mixed into the normal feeding of the DSP group. The model group and normal control group were given normal feedings. The experiment lasted for 6 months. Total cholesterol (TC), High density Lipoprotein-c (HDL-c), and Low-density lipoprotein-c (LDL-c) were measured using U.S. Berer testing. Triglycerides (TG) used acetylacetone colorimetry. The Plasma Nitrogen Monoxide (NO) was measured by Fluorescence Spectrophotometry, and Propandiol (MDA) was measured by TBA colorimetry. (GSH-PX) used the DTNB method. Tissue-type plasminogen activator (t-PA), plasminogen activator inhibitor (PAI), DD, FDP were tested by enzyme linked immunosorbent assay. Insulin Radioimmunoassay and Glycated Hemoglobin (HbA$_1$c) were measured by high-performance liquid chromatography. Contraves low share 30 was used to test blood flow (made in Switzerland).

Results. After 6 months, the protein content of the 24-hr DSP group was much lower (45% lower) than that of the model group (P<0.001) Uric acid (UA) dropped at the same time (P<0.001), but there was a significant difference between the two groups as far as blood serum creatinine (Scr), blood serum urea nitrogen (BUM) and urine volume (P>0.05), as shown in Table 9.1. The PAI, DD and FDP of the model group and DSP group were much higher than that of the normal control group (P<0.001). t-Pa was lower than that of the normal control group, too (P<0.001). When compared with the model group, the t-PA of the DSP group rose significantly (P<0.001), and PAI, DD and FDP dropped (P<0.001), as shown in Table 9.2. The TG, TC, HDL-c, NO, and MDA content and GSH-PX activity of the DSP group were similar to that of the model group (P>0.05).

Conclusion. DSP cannot thoroughly protect blood vessels and nerves or prevent the occurrence of blood vessel and nerve lesion in diabetic rats, but it can relieve or reduce its occurrence in the 6 months-diabetic rat, especially in terms of protein in the urine and lesion of blood capillaries of the kidneys and retina. This may be related to the function of DSP, which can increase thrombolysis.

TABLE 9.1

Changes and comparison of function of kidneys in each group after 6 months

| | n | Scr (mg/dl) | BUN (mg/dl) | UA (mg/dl) | Volume of urine (ml) | 24 h Protein (mg) |
|---|---|---|---|---|---|---|
| Normal Control group | 10 | 0.76 ± 0.219 | 17.3 ± 3.24 | 1.79 ± 0.326 | 13.6 ± 5.03 | 11.41 ± 4.04 |
| Model group | 7 | 0.72 ± 0.075 | 35.6 ± 15.5# | 3.47 ± 0.903* | 155.8 ± 29.8□ | 111.7 ± 23.845□ |
| DSP group | 7 | 0.73 ± 0.087 | 31.98 ± 11.45* | 2.66 ± 1.04#Δ | 145.3 ± 25.41□ | 50.5 ± 28.24Δ* |

Notes:
Comparison with normal control group,
□ $P < 0.001$,
* $P < 0.01$,
$P < 0.05$;
Comparison with model group,
Δ $P < 0.001$

TABLE 9.2

Changes and comparison of t-PA, PA, DD and FDP in each group

| | n | t-PA (IU/ml) | PAI (IU/ml) | DD (mg/l) | FDP (ug/ml) |
|---|---|---|---|---|---|
| Normal control group | 10 | 0.579 ± 0.033 | 0.748 ± 0.026 | 0.42 ± 0.048 | 4.645 ± 0.33 |
| Model group | 7 | 0.186 ± 0.011* | 0.898 ± 0.02* | 0.714 ± 0.018* | 6.667 ± 0.087* |
| DSP group | 7 | 0.255 ± 0.011*# | 0.855 ± 0.014*# | 0.532 ± 0.077*# | 5.643 ± 0.037*# |

Notes:
Comparison with normal control group,
* $P < 0.001$;
comparison with model group,
$P < 0.001$

TABLE 9.3

Comparison of endogenous and patrolling cells in the retina and their ratio after DSP treatment

| | n | Endogenous cells | Patrolling cells | E/P |
|---|---|---|---|---|
| Normal group | 10 | 667 ± 40.855 | 333 ± 40.741 | 2.042 ± 0.394 |
| Model group | 7 | 861 ± 43.760▲ | 138 ± 43.760▲ | 6.829 ± 2.246▲ |
| DSP group | 7 | 737 ± 32.408Δ# | 262 ± 32.408Δ# | 2.864 ± 0.533■* |

Notes:
Comparison with normal control group,
▲ $P < 0.001$,
$P < 0.01$,
■ $P < 0.001$;
comparison with model group,
Δ $P < 0.001$
* $P < 0.001$ In conclusion, DSP can increase blood flow to the coronary artery; relax the smooth muscles in blood vessels; activate peripheral circulation; raise venous oxygen content; significantly improve acute myocardial infarction; reduce apoptosis by interfering with Fas/FasL protein expression to protect the cells from damage by hypoxia and deoxygenation/re-oxygenation; improve circulation; and protect myocardial tissue. It can also prevent cardiac arrhythmia and platelets aggregation; activate thrombolysis; reduce blood viscosity; adjust lipoprotein levels; prevent atherosclerosis; increase tolerence to hypoxia; prevent oxidation of fats; remove harmful free radicals; reduce ET content in blood plasma; and improve the liver, kidney and pancreas function to prevent the occurrence of blood vessel and nerve lesion.

Clinical Research on Dan Shen Pill

1. Treatment of Coronary Heart Disease with DSP (1) Ordinary Treatment of Coronary Heart Disease with DSP After DSP came onto the market in China, a large-scale clinical research project was conducted in China. Although different prescriptions were used in different research projects, all conclusions are written according to "Method of DSP clinic study." All clinical and experimental markers were standardized. A simplified summary of the results is shown below in Table 1-1.

TABLE 1-1

Clinical conclusion of effects of DSP on treatment of coronary heart disease and angina

| Name of hospital | Case | Clinical efficacy % | ECG-Efficacy % | Normal control[1] |
|---|---|---|---|---|
| Huabei Chinese Hospital | 80 | 87.5 | — | — |
| Shan Dong Weifang Hospital | 162 | 86.6 | 70.7 | — |
| Zhejiang hospital of Traditional Chinese Medicine | 100 | 96** | — | DSP(50; 92%; —) |
| Affiliated Hospital Hunan College of TCM | 98 | 93.9 | 58.3 | — |
| Guangzhou Hospital of TCM | 100 | 96** | 63* | DSP(30; 63.3%; 30%) |
| Tangshan Hospital of TCM | 101 | 95.1 [84.2]** | 60.4 [46.5]* | Isordil(48; 79.2%; 37.5%) [87.5%; 43.8%] |
| Affiliated Hospital Anhui College of TCM | 46 | 95.7* | 76.1* | Nifedipine(32; 75%; 43.8%) |
| Hunan Shuangfeng Hospital | 32 | —[2] | 82.4** | Isordil(31; —; 74.5% |
| Shanxi Provincial Hospital | 97 | 78.4* | 41.5 | DSP(41; 65.9%; 32.3%) |
| Jingxi Hospital, 4th Medicine University | 39 | 92.4 | 79.5 | — |
| Guangzhou Hospital of TCM | 120 | 92.5 | 60 | — |
| Shenyang Seventh Hospital | 62 | 93.5 | 74.2 | Isordil(30; 72.5%; 60%) |
| Guangdong Affiliated Hosp. of TCM | 30 | 66.7 | — | Isordil(23; 69.6%) |
| Guang'anmen Research Institute of TCM | 40 | 92.5 | 60 | Isordil(20; 90%; 55%) |
| Tianjin First Hospital | 128 | 82.8 | — | — |
| Affiliated Hospital of Anhui College of TCM | 102 | [88.3] | [37.3] | Glyceryl trinitrate(30; [93.3%; 40%]) |
| The 1st Affiliated Hospital, Hebei Medicine College | 34 | —[3]** | — | Isordil (30) |
| Tianjin Huanhu Hospital | 58 | 96.5* | 53.5 | DSP(152; 75.1%; 46.2%) |
| Fujian Provincial Hospital | 100 | 96 | 89.1 | — |
| Changzhou Hospital in Jiangshu Province | 43 | 95.3** | 62.8** | DSP(43; 74.4%; 37.5%) |
| Shanxi Research Institute of Traditional Chinese Medicine | 206 | 92 | 63.6 | — |
| Xintai Hospital in Hebei Province | 60 | 96.7** | 63.3 | DSP(30; 76.6%; 43%) |
| The 1st Affiliated Hospital of Shanghai Medicine University | 30 | 83.3 | 56.6 | — |
| Henan Dianli Hospital | 90 | 91.1 | 60 | — |
| Jinan Provincial Hospital | 60 | 76.7* | 61.7** | Isordil(30; 53.3%; 36.7) |
| Xi'an Military Hospital | 87 | 96[4] | 64.6 | Glyceryl trinitrate(87[4]) |
| Total | 2105 | 90.06 | 61.8 | |

Note:
The numbers inside the [ ] represent the pain-killing function and improvement in ECG results.
Comparison with normal control group, *p < 0.05; **p < 0.01

[1] Numbers in the ( ) in order of appearance are: sample number, angina improvement after treatment and percentage improvement in ECG after treatment.
[2] The standard markers were cardiac output (CO), stroke volume (SV), Ejection fractin(EF), (FS), β platelet microglobulin, Thromboxane $β_2$, Holter Test for ST-T changing times, etc.
[3] The standard markers were Heart Ratio(HR), systolic pressure (SBP), (Product), diastolic pressure(DBF), output(SV) per pulse, cardiac output (CO), cardiac Index(CI), ejection fration(EF), angina onset frequency, and dosage of glyceryl trinitrate.
[4] This was a cross companion test, so there is no statistical difference between the medicine in the angina group and in the ECG group.

According to Table 1-1, the effects of DSP on the treatment of coronary heart disease are much better than that of DSS, statistically. The treatment is basically similar to that of Isordil and there is no significant difference between them statistically. DSP is a pure Chinese medicine. It works efficiently in small dosages. It is convenient, safe, easily-absorbed, and has no side effects.

(2) Pain-Killing Effects of DSP on Coronary Heart Disease Compared with Glyceryl Trinitrate. The Pain-Killing Function of DSP for Coronary Heart Disease is Discussed.

1. Example. 132 patients with coronary heart diseases were selected. They were divided into 2 random groups, 102 patients in the treatment group and 30 patients in the control group. They were classified according to Chinese Medical Method into: 42 patients in the Qizhi Xueyu treatment group, 24 patients in the Tanshi Bizhu treatment group, 7 patients in the Yangxu Hanning treatment group, 29 patients in the Qiyin Liangxu and Xueyu treatment group; and 11, 7, 2, and 10 patients, respectively, were assigned to the control groups.

2. Method. An ECG was conducted once before the pain begins. Patients in the treatment group took 10 DSP during the pain, while those in the control group took 0.5 mg glyceryl trinitrate. The time it took for the pain to end was recorded and used as a reference. An ECG was conducted again 30 mins after treatment and compared it with the one taken before.

3. Standard. Three pain-killing standards were established: obvious effectiveness—pain ended 3 minutes after treatment; effectiveness—pain ended 3~8 minutes after treatment; and Failure-pain ended 8 hrs or more after treatment.

Results (1) Speedy Painkilling. The obvious effectiveness of the treatment group was 40.20%, and the total efficacy was 88.28%. The obvious effectiveness of the control group was 53.33%, and total efficacy was 93.33%. There was no significant difference between the two groups ($P>0.05$). These two groups have a similar treatment effect on coronary heart diseases, as shown in Table 1-2.

TABLE 1-2

Efficacy of painkilling

| Group | Case No. | Obvious Efficacy (%) | Efficacy (%) | Failure (%) | Total efficacy (%) |
|---|---|---|---|---|---|
| Treatment | 102 | 41 (40.20) | 49 (48.04) | 12 (11.76) | 90 (88.24) |
| Control | 30 | 16 (53.33) | 12 (40.00) | 2 (6.67) | 28 (93.33) |

(2) Using ECGs to compare treatment results, the obvious efficacy in the treatment group was 15.69%. The total efficacy was 37.26%. The obvious efficacy in the control group was 20%, and total efficacy was 40%. There was no significant difference between the groups ($P>0.05$), as shown in Table 1-3.

TABLE 1-3

Efficency on ECG After Dosage

| Group | Case No. | Obvious Efficacy (%) | Efficacy (%) | Failure (%) | Total efficacy(%) |
|---|---|---|---|---|---|
| Treatment | 102 | 16 (15.69) | 22 (21.57) | 64 (62.74) | 38 (37.26) |
| Control | 30 | 6 (20.00) | 6 (20.00) | 18 (60.00) | 12 (40.00) |

(3) There is a close relationship between Chinese Classification of Coronary Heart Disease and the efficacy in the treatment group, as shown in Table 1-4. It shows that DSP has the identical treatment efficacy on the different categories of heart pain classified by Chinese medicine.

TABLE 1-4

Efficacy in the treatment group in Traditional Chinese Medicine Classification of Coronary Heart Disease

| Group | Cases | Obvious Efficacy (%) | Efficacy (%) | Failure (%) | Total efficacy (%) |
|---|---|---|---|---|---|
| Qizhi Xueyu | 42 | 18 (42.86) | 19 (45.24) | 5 (11.90) | 37 (88.10) |
| Tangshi Bozhu | 24 | 7 (29.17) | 14 (58.33) | 3 (12.50) | 21 (87.50) |
| Yinshi Hanling | 7 | 4 (57.14) | 2 (28.57) | 1 (14.29) | 6 (85.71) |
| Qiyin Liangxu And Xueyu | 29 | 12 (41.38) | 14 (48.28) | 3 (10.34) | 26 (89.66) |

Conclusion

The above experiment shows that the effects of DSP treatment on for coronary heart disease is similar to that of glyceryl trinitrate. The results of both ECGs are similar 30 mins after treatment, and the Chinese classification of coronary heart disease does not affect the efficacy of DSP.

(3) Effects of DSP on the Onset of Coronary Heart Disease, Heart Pain Frequency and Volume of Glyceryl Trinitrate Used.

1. Sample selection. Samples were selected according to WHO clinical standards. Patients must have exhibited least exertion-related angina pectoris for 3 months. Onset frequency was more than 5 times a week with positive results in exercise tests and pain relieved by rest or oral glyceryl trinitrate. The total number in the sample was 64.

2. Method of research. The research was divided into two periods at random using the double-blind method. The first period (cleansing period) lasted 2 weeks. All medications except for glyceryl trinitrate were stopped. The second period lasted 8 weeks, and 10-15 DSP were given to one group, 3 times per week, while 10-15 mg of Isordil was given to another group, 3 times a week.

3. Results. Onset frequency of the DSP-protected group decreased from 1.93±3.10 to 0.48±1.33 with a statistical error of $P<0.01$. The volume of glyceryl trinitrate used decreased from 1.88±2.96 tablets per day to 0.51±1.44 tablets per day with a significant difference ($P<0.01$), as shown in Table 1-5.

TABLE 1-5

Changes in onset frequency and volume of glyceryl trinitrate used

|  | DSP group (n = 34) | | Isordil group (n = 30) | |
| --- | --- | --- | --- | --- |
|  | Before treatment | After treatment | Before treatment | After treatment |
| Onset Frequency (times/day) | 1.93 ± 3.10 | 0.48 ± 1.33**## | 1.91 ± 2.44 | 1.64 ± 1.62* |
| glyceryl trinitrate used (tablet/day) | 1.88 ± 2.96 | 0.51 ± 1.44**## | 1.86 ± 4.51 | 1.64 ± 1.46* |

Notes:
Comparison before and after treatment,
*P < 0.05
**P < 0.01,
Comparison between the 2 groups,
P < 0.01

The results show that DSP can reduce onset frequency and volume of glyceryl trinitrate used. The level and duration of pain improved after a certain period of treatment, and the onset frequency also decreased. This explains why DSP can improve blood flow to the heart in addition to relieving pain.

(4) Improvement of blood pressure and cardiac function in patients with coronary heart disease. Method of sample selection and the method of research are the same as (3).

The results are shown in Tables 1-6 and 1-7. They prove that DSP can improve cardiac function in patients with coronary heart disease and provide improvements in blood flow.

TABLE 1-6

Changes in heart rete, blood pressure, and corresponding product in DSP treatment and Isordil treatment index

|  | DSP group (n = 34) | | Isordil group (n = 30) | |
| --- | --- | --- | --- | --- |
| Marker | Before treatment | After treatment | Before treatment | After treatment |
| SBP (Kpa) | 24.5 ± 2.1 | 23.2 ± 1.4**## | 23.9 ± 4.1 | 24.8 ± 1.1 |
| DBP (Kpa) | 11.8 ± 4.1 | 11.1 ± 2.1**## | 11.8 ± 3.2 | 12.1 ± 2.1 |
| Corresponding product | 24399 | 18932**## | 24399 | 26203 |

Notes:
Comparison before and after treatment by matching t statistic testing: **P < 0.01, Comparison between the 2 groups, ##P < 0.01

TABLE 1-7

Changes in blood flow indexes after DSP treatment and Isordil treatment

|  | DSP group (n = 34) | | Isordil group (n = 30) | |
| --- | --- | --- | --- | --- |
| Markers | Before treatment | After treatment | Before treatment | After treatment |
| PAP (mmHg) | 34.4 ± 6.1 | 27.4 ± 8.8 | 34.8 ± 5.1 | 33.9 ± 6.6 |
| PCWP (mmKg) | 34.8 ± 9.1 | 24.3 ± 6.7 | 32.6 ± 8.1 | 31.1 ± 5.1 |
| CO (L/min) | 2.81 ± 0.4 | 4.64 ± 1.1 | 3.81 ± 0.1 | 3.89 ± 1.1 |
| CI (I min$^{-1}$/m$^2$) | 3.47 ± 1.1 | 3.89 ± 0.3 | 3.51 ± 1.0 | 3.58 ± 1.6 |
| EF (%) | 76 ± 11 | 74 ± 16 | 77 ± 14 | 78 ± 11 |

Notes:
Comparison before and after treatment by matching t statistic testing: *P < 0.05 **P < 0.01, Comparison between the two groups, #P < 0.05 ##P < 0.01

(5) Effects of DSP on ECGs and blood flow in patients with coronary heart disease By comparing DSP and well-known pain medication Isordil, DSP's clinical treatment effects and toxic side effects are discussed.

1. Objects and Methods 1.1 Sample. The total number of patients with steady angina pectoris was 109. They all qualified under WHO Standard Cardiac function Category I~II, 1979. They were divided into two groups at random: 57 in the treatment group and 52 in the Isordil group (control group).

1.2 Method. All patients stopped taking all myocardial ischemia medications for five half-lives before beginning treatment. Patients with coronary heart disease were given oral glyceryl trinitrate temporarily. The treatment group was given DSP, while the control group was given Isordil (Shanghai Medical University Red Flag Medicine Factory), 10-15 mg/time, 3 times/day. Medication was taken for 4 weeks.

1.3 Recording Standards. Onset frequency, body parts, level of pain, heartbeat, blood pressure, duration, onset factors, consumption of glyceryl trinitrate, time it takes for the medicine to begin functioning, Movable Plane Exercise Test results, and blood flow.

1.4 Treatment standard:

1.4.1 Symptom standards. (a) Obvious Efficacy: The same level of fatigue did not trigger onset of pain, or onset frequency decreased by more than 90 percent. Glyceryl trinitrate was not used. (b) Efficacy: Onset frequency and amount of glyceryl trinitrate used decreased 0-90%. (c) Failure: The above standards could not be reached. (d) Worsening: Onset frequency and amount of glyceryl trinitrate used increased 50% or more.

1.4.2 ECG standards: (a) Obvious Efficacy: The result of the Movable Plane Exercise Test changed from positive to negative, or exercise tolerance increased to ≧grade 2. (b) Efficacy: Movable Plane Exercise Test ECG ischemia ST segment rebounded to ≧1.5 mm, or exercise tolerance increased 1 grade (c) Failure: The above standards were not reached.

Results 2.1 Observation of symptomic efficacy. See Table 1-8. Total efficacy: treatment group 93.0%; control group 86.5%. No significant difference between the two groups (P>0.05).

2.2 Observation of ECG efficacy: See Table 1-9 and Table 1-10. The Onset of angina without exercise and onset of angina with exercise for section ST decreased ≧0.1 mv in the 2 groups after treatment. There were improvements in the greatest decreasing value of section ST and the greatest payload, but there is no significant difference between them (P>0.05). All standards in the treatment group improved both before and after treatment (P<0.01).

2.3 Observations on blood flow were shown in Table 1-11. All standards in the treatment group have improved after treatment (P<0.01), but there was no difference in those of the control group (P>0.05). Significant differences in blood flow were found between the two groups (P<0.01). This shows that DSP can improve blood flow.

TABLE 1-8

Comparison of the symptoms in the two groups before and after treatment

| Group | Cases | Results Obvious Efficacy | Efficacy | Failure | Worsening cases | Total efficacy (%) |
|---|---|---|---|---|---|---|
| DSP | 57 | 32 | 21 | 3 | 1 | 93.0* |
| Isordil | 52 | 28 | 17 | 5 | 2 | 86.5 |

Notes:
Comparison with the control group,
*P > 0.05

TABLE 1-9

Comparison of the ECG in the two groups before and after treatment

| Group | Cases | Obvious Efficacy | Efficacy | Failure | Worsening case | Total efficacy (%) |
|---|---|---|---|---|---|---|
| DSP | 49 | 19 | 11 | 18 | 1 | 61.4* |
| Isordil | 47 | 16 | 12 | 17 | 2 | 59.6 |

Notes:
Comparison with the control group, *P > 0.05

TABLE 1-10

Changes in Movable Plane Exercise indexes before and after treatment

| Group | Cases | trigger time | Time for section ST 0.1 mV lower (sec.) | Exercise required for Section ST 0.1 mV lower (MET) | The lowest of section ST (mm) | The greatest payload (METS) |
|---|---|---|---|---|---|---|
| DSP | 49 | | | | | |
| Before treatment | | 228 ± 60 | 204 ± 79 | 4.2 ± 2.0 | 2.5 ± 1.8 | 7.3 ± 1.2 |
| After treatment | | 301 ± 94* | 268 ± 92* | 5.6 ± 2.3* | 1.8 ± 1.1* | 9.8 ± 2.1* |
| Isordil | 47 | | | | | |
| Before treatment | | 230 ± 39 | 210 ± 76 | 4.5 ± 1.8 | 2.2 ± 0.9 | 7.8 ± 1.6 |
| After treatment | | 303 ± 89 | 257 ± 85 | 5.8 ± 2.6 | 1.6 ± 0.8 | 10.1 ± 2.2 |

Notes:
*Comparison with this group before treatment, P < 0.01;
Comparison with control group after treatment, P > 0.05.

TABLE 1-11

Changes in blood flow indexes in the two groups before and after treatment

| Group | Cases | Whole blood Viscosity | Blood plasma viscosity | Sedimentation equation value K | Blood platelet viscosity percentage (%) | Length of exogenous thrombin (mm) |
|---|---|---|---|---|---|---|
| DSP | 52 | | | | | |
| Before treatment | | 5.31 ± 0.89 | 1.83 ± 0.86 | 103.78 ± 12.68 | 30.25 ± 7.84 | 18.5 ± 3.0 |

TABLE 1-11-continued

Changes in blood flow indexes in the two groups before and after treatment

| Group | Cases | Whole blood Viscosity | Blood plasma viscosity | Sedimentation equation value K | Blood platelet viscosity percentage (%) | Length of exogenous thrombin (mm) |
|---|---|---|---|---|---|---|
| After treatment | | 4.67 ± 0.71* | 1.35 ± 0.92* | 96.45 ± 10.21* | 25.30 ± 5.90* | 16.0 ± 3.1* |
| Isordil | 50 | | | | | |
| Before treatment | | 5.33 ± 0.93 | 1.81 ± 0.81 | 105.15 ± 12.68 | 30.75 ± 6.93 | 18.2 ± 2.7 |
| After treatment | | 5.20 ± 0.96 | 1.80 ± 0.68 | 102.26 ± 12.11 | 29.10 ± 8.50 | 18.0 ± 2.4 |

Notes:
*Comparison with this group before treatment,
$P < 0.01$;
Comparison with control group after treatment.
$P < 0.01$
Self-matching t test before and after treatment:
*$P > 0.05$.
t test in 2 groups:
** $P > 0.05$ Conclusion No significant differences appeared on ECGs and average exercise testing standards to show improvement from DSP and Isordil (P>0.05), but the average exercise testing standards in the DSP group were much better before and after treatment (P<0.01). This test proves that the treatment effects of DSP on coronary heart disease are the same as that of Isordil with no side effects and increase in tolerence. Also, DSP controls irregular blood flow, lowers blood viscosity, reduces the occurence of atherosclerosis, and prevents thrombosis much better than Isordil and can be the first choice for the treatment of coronary heart disease.

(6) Effects of long-term DSP treatment on coronary heart disease The effects of long-term DSP treatment on coronary heart disease in comparison to Isordil are discussed.
1. Subjects. 40 patients with stable-type angina are selected, and divided into two groups at random, 20 in the treatment group (DSP group) and 20 in the control group (Isordil group.
2. Method. Patients are medicated and observed using double-blind method. The DSP group takes 10 tablets/day, 3 times/day, and the Isordil group takes 10 mg, 3 times/day.

Results
1. Efficacy. There was difference after 2 weeks of medication. The results were 90% vs 75% (P>0.05, 90% vs 70% (P<0.05), 95% vs 65% (P<0.01) in 4, 6 and 8 weeks respectively with the DSP group showing results superior to that of the control group.

2. Electrocardiography (ECG) Efficacy: There was difference between the two groups after 2 weeks of medication. The results were 80% vs 65% (P<0.05), 75% vs 55% (P<0.05), 80% vs 50% (P<0.08) at 4, 6 and 8 weeks, respectively, with the DSP group showing results superior to that of the control group (Table 1-12).

TABLE 1-12

Comparison of treatment efficacy based on ECG results

| Results | | 2 weeks DSP | 2 weeks Isordil | 4 weeks DSP | 4 weeks Isordil | 6 weeks DSP | 6 weeks Isordil | 8 weeks DSP | 8 weeks Isordil |
|---|---|---|---|---|---|---|---|---|---|
| Efficacy of angina pectoris (%) | Obvious Efficacy | 5 (25.0) | 6 (30.0) | 6 (30.0) | 5 (25.0) | 6 (30.0) | 4 (20.0) | 7 (35.0) | 3 (15.0) |
| | Efficacy | 12 (60.0) | 12 (60.0) | 12 (60.0) | 10 (50.0) | 12 (60.0) | 10 (50.0) | 12 (60.0) | 10 (50.0) |
| | Failure | 3 (15.0) | 2 (10.0) | 2 (10.0) | 5 (25.0) | 2 (10.0) | 5 (25.0) | 0 (0) | 5 (25.0) |
| | Worsen cases | 0 (0) | 0 (0) | 0 (0) | 0 (0) | 0 (0) | 1 (5.0) | 1 (5.0) | 2 (10.0) |
| | Efficacy rate | 17 (85.0) | 18 (90.0) | 18 (90.0) | 15 (75.0) | 18 (90.0) | *14 (70.0) | **19 (95.0) | 13 (65.0) |
| | P value | >0.05 | | <0.05 | | <0.05 | | <0.01 | |
| Efficacy of ECG (%) | Obvious Efficacy | 4 (20.0) | 4 (20.0) | 5 (25.0) | 3 (15.0) | 5 (25.0) | 3 (15.0) | 6 (30.0) | 2 (10.0) |
| | Efficacy | 10 (50.0) | 11 (55.0) | 11 (55.0) | 10 (50.0) | 10 (50.0) | 8 (40.0) | 10 (50.0) | 8 (40.0) |
| | Failure | 6 (30.0) | 5 (25.0) | 4 (20.0) | 5 (25.0) | 4 (20.0) | 7 (35.0) | 3 (15.0) | 7 (35.0) |
| | Worsen cases | 0 (0) | 0 (0) | 0 (0) | 2 (10.0) | 1 (5.0) | 2 (10.0) | 1 (5.0) | 3 (15.0) |

TABLE 1-12-continued

Comparison of treatment efficacy based on ECG results

| Results | | 2 weeks | | 4 weeks | | 6 weeks | | 8 weeks | |
|---|---|---|---|---|---|---|---|---|---|
| | | DSP | Isordil | DSP | Isordil | DSP | Isordil | DSP | Isordil |
| | Efficacy rate | 14 (70.0) | 15 (75.0) | 16 (80.0) | 13 (65.0) | 15 (75.0) | *11 (55.0) | **16 (80.0) | 10 (50.0) |
| | P value | >0.05 | | <0.05 | | <0.05 | | <0.01 | |

Notes:
Comparison at 6 weeks and 2 weeks on medication:
DSP group
*P > 0.05;
Control group
**P < 0.05

Conclusion

Long-term DSP treatment is more efficient and yields better ECG results than Isordil treatment. The results are stable, and there is no antibiotic resistance. Isordil can efficiently lower blood pressure, leading to the activation of endogenous nerve and body fluid system and an increase in blood volume. In addition, Isordil works on sulfur radicals inside the capillary wall, but it would consume sulfur radicals in the long term and reduce treatment effects. DSP is a multi-level, multi-subjected and multi-method medicine which improve cardiac muscle, increases blood volume by blocking the chronic calcium route; stabilizes the myocardial membrane; removes free radials; regulates myocardial cells metabolism; improves blood platelets aggregation; and lowers cholesterol and blood viscosity. Therefore, long-term DSP treatment gives significant treatment effects.

(7) Treatment of Unstable-Type Angina

Clinical research on the effects of DSP on unstable-type angina.

1. Subjects and Methods
1.2 Sample: 65 patients with unstable-type angina were divided into two groups at random: 34 in the treatment group, which includes 22 males and 12 females; 31 in the control group which includes 20 males and 11 females.
1.3 Method. Two groups of patients were injected normally with 30 ml of DSP, Qd, 80 mg oral aspirin, Qd. Patients in the treatment group were given DSP, 10 tablets/day, 3 times/day; Isordil was given to those in the control group, 10 mg/time, 3 times/day. The medication lasted for 20 days. No coronary artery-dilating and fat-lowering drugs were given. If pain worsened, glyceryl trinitrate was given.

Results

1. Comparison of results. In the treatment group, the number of obvious efficacy, efficacy, failure and worsening cases were 26%, 6%, 2%, 0, respectively, and the total efficacy was 94.1%. In the control group, the results were 15%, 8%, 6%, 2%, respectively, and the total efficacy was 74.2%. The results of both groups were classified under the Ridit statistic testing Method (P<0.05).

2. Comparison of coronary heart disease classifications before treatment. Patients exhibiting low, medium, low-medium and high symptoms according to the Ridit statistic testing Method (P<0.05) in the treatment group were 27, 4, 2, and 1, respectively. Those in the control group were 14, 9, 7, and 1, respectively.

3. Comparison of ECGs: the total efficacy in the treatment group was 61.7%, and that of the control group was 41.94%. There was a significant difference in the efficiencies of the two groups.

4. Treatment of related symptoms. Related symptoms include palpitation, a suffocation of sense, oral cyanosis. After treatment, there was a more significant difference in the number of patients suffering from a sense of suffocation, oral cyanosis and ecchymosis in the treatment group than in the control group (P<0.01). However, there was no difference in palpitation (P<0.05).

5. For change in blood flow. See Table 1-13.

TABLE 1-13

Change in blood flow

| | Experimental group | | Control group | |
|---|---|---|---|---|
| Standards | Before treatment | After treatment | Before treatment | After treatment |
| Whole blood viscosity (cp) | 4.91 ± 0.42 | 4.02 ± 0.32*Δ | 4.86 ± 0.38 | 4.56 ± 0.41 |
| Erythrocyte hematocrit (%) | 49.20 ± 2.74 | 42.28 ± 2.12* | 52.00 ± 2.52 | 48.53 ± 2.13 |
| Blood sedimentation (mm/h) | 24.65 ± 9.76 | 22.18 ± 8.23 | 25.10 ± 9.34 | 22.30 ± 8.17 |
| Fibrinogen (mg %) | 487.50 ± 85.14 | 403.33 ± 91.15**ΔΔ | 494.33 ± 86.02 | 487.00 ± 89.61 |

Notes:
Comparison with this group before treatment, *P < 0.05; Comparison with control group, ΔP < 0.05, ΔΔP < 0.01

Conclusion

The above experiment shows that DSP can reduce oxygen consumption by cardiac muscles, improve blood flow in coronary arteries, rebalance oxygen demand-to-oxygen supply ratio in cardiac muscles.

The effects of DSP on treatment of exertion-type of angina on 60 additional patients.

1. Sample selection. 60 patients in total, including 42 males and 18 females, aged 32-75, with an average age of 52.2, and positive results in the Plane Exercise Test were selected.
2. Method of medication. DSP was given, under lingua, 10 tablets/medication, 3 times/day. The medication lasted for 6 weeks.
3. Results. Refer to the 1997 CHD Angina Standard.
  (1) Efficacy. No occurrence of angina, 21 patients with increased physical tolerance (35%), 15 patients with negative results in the Plane Exercise Test (25%).
  (2) Improvement. 29 patients with a two-thirds decrease in the frequency of onset of pain or shortening of the duration of pain (48.3%), 28 patients with suspicious positive results in the Plane Exercise Test (46.5%).
  (3) Failure. 10 patients had no change in onset frequency and duration (16.7%). 17 patients had positive results in the Plane Exercise Test (28.3%).

Conclusion

DSP can efficiently relieve pain and increase blood flow to the cardiac muscle. DSP can also reduce oxygen consumption, improve blood flow to the coronary artery, rebalance oxygen demand and oxygen supply, and prevent atherosclerosis. It is the ideal medicine for the prevention or treatment of coronary heart disease, angina and atherosclerosis.

(8) Research on Senior Group Angina

Both DSP and Nifedipine can treat angina caused by coronary heart disease, but the latter has side effects which are not suitable for long-term use. In order to choose suitable drugs for patients with a need for long-term treatment of coronary heart disease, a comparative analysis of DSP and Nifedipine in the treatment of angina caused by coronary heart disease was carried out.

1. Materials and Methods
1.1 Subjects. 50 senior patients with coronary heart disease were divided into two groups: 30 in the DSP group (Treatment group), 20 in the Nifedipine group (Control group). Patients in both groups did not have significant differences in terms of sex, age, medication, and Chinese medical classification, but a comparison of the differences is worthwhile.
1.2 Method. DSP was given to the Treatment group, 10-15 tablets/medication, 3 times/day; Nifedipine was given to the Control group, 10~15 mg/medication, 3 times/day. Medications were taken for 30 days. Patients in both groups used Yongbaoling spray under their tongues during acute onset of symptoms. Other medications with no obvious effects were used during the treatment process.
1.3 Types of tests. Onset frequency, duration, number of times Yongbaoling was sprayed each day, 12-lead ECG, blood pressure, heartbeat, normal blood urea, liver and kidneys function, and lipoproteins in blood and blood viscosity both before and after treatment.
1.4 Statistical analysis. The results were measured by t statistic testing, calculated by $x^2$ statistic testing.
2. Confirmation of results. Onset frequency and duration with a decrease of 80% or more was regarded as obvious efficacy. A decrease of 50% or more was regarded as efficacy. A decrease of 50% or less was regarded as a failure. Changes in NST and $\Sigma$ST before and after treatment were used to observe ECG improvement. NST represented the low-pressure 12-lead numbers in section ST; $\Sigma$ST represented the sum of all low pressure numbers in section ST of 12-lead.

Results

Clinical results are shown in Table 1-14.

TABLE 1-14

Comparison of clinical results of the two groups after treatment (%)

| Group | Sample number | Obvious Efficacy | Efficacy | Failure | Total efficacy (%) |
|---|---|---|---|---|---|
| With treatment | 30 | 19 (63.33) | 8 (26.67) | 3 (10.00) | 90 |
| Control | 20 | 8 (40.00) | 4 (20.00) | 8 (40.00) | 60 |

Notes:
Comparison with control group,
P < 0.05

3.2 Change in ECG and number of times Yongbaoling was sprayed per day is shown in Table 1-15.

TABLE 1-15

Comparison of change of NST and $\Sigma$ST and usage of Yongbaoling sprays

| Group | | Sample number | NST | $\Sigma$ST | Number of Yongbaoling sprays per day |
|---|---|---|---|---|---|
| With treatment | Before treatment | 30 | 4.21 ± 1.31 | 1.76 ± 0.87 | 3.1 ± 1.0 |
| | After treatment | | 3.10 ± 1.21 | 1.05 ± 0.61 | 1.0 ± 0.5 |
| Control | Before treatment | 20 | 4.20 ± 1.25 | 1.75 ± 0.85 | 3.21 ± 1.1 |
| | After treatment | | 3.90 ± 1.13 | 1.60 ± 0.71 | 2.2 ± 0.8 |

Notes:
Comparison before and after treatment, P < 0.05; Comparison between treatment group and control group, P < 0.05.

3.3 Side-effects: 3 patients in the Nifedipine group felt pain, 2 had swollen ankles, 1 had slow heartbeat. There was no damage to liver and kidney function, adverse gastrointestinal reaction or cardiac arrhythmia in the treatment group.

Conclusion

DSP is made for angina. It activates blood circulation and relieves pain efficiently. Its effects are long lasting, require only a small dosage and have no side effects. Nifedipine is a short-term-effective calcium antagonist with a short half-life and functional time, so angina may occur during medication. It also has many side effects. Many reports state that long-term treatment with Nifedipine is harmful to coronary arteries. DSP can prevent decreased blood flow to the cardiac muscles and the development of atherosclerosis.

(9) Effects on Non-Symptomatic M-IR

1. Clinical sample. 52 patients were in the treatment group, which included 39 patients with coronary heart disease, and 4 patients with M-IR, and 9 patients with positive results on the exercise test. There were 38 males and 14 females. 52 patients were in the control group, which included 43 patients with coronary heart disease, 6 patients with M-IR, and 3 patients with positive results on the exercise test. There were 34 males and 18 females (Both groups followed the WHO M-IR-Related Heart Disease and Standard established in 1979).

2. Method of treatment. DSP was given to the treatment group, 10 tablets/medication, 3 times/day. Nifedipine was given to the control group, 10 mg/medication, 3 times/day. Both medications lasted for 4 weeks, and all medications related to the treatment of M-IR were stopped.

3. Result standard. Efficient: Change of ECG ST-T was close to normal; Better: Decreased section ST rose 0.5 mm or more, transverse wave T changed to vertical ones, inverted wave changed 25% or more, conducting resistance was improved; Failure: There was no difference in ECGs before and after treatment.

Results (1) Efficacy in both the DSP group and the Nifedipine control group increased as treatment progressed, as shown in Table 1-16. There was a significant difference between the groups ($P<0.01$)

TABLE 1-16

Efficient dynamic changes in 2 groups after treatment

| Group | | $1^{st}$ week | $2^{nd}$ week | $3^{rd}$ week | $4^{th}$ week |
|---|---|---|---|---|---|
| With treatment (n = 52) | Obvious Efficacy (Number) | 12 | 17 | 21 | 22 |
| | Efficacy (Number) | 10 | 13 | 15 | 17 |
| | Efficacy (%) | 42.3 | 57.7 | 69.2 | 75.0 |
| Control (n = 52) | Obvious Efficacy (Number) | 8 | 10 | 11 | 12 |
| | Efficacy (Number) | 5 | 6 | 7 | 8 |
| | Efficacy (%) | 25.0 | 30.8 | 34.6 | 38.5 |

(2) 24-hr dynamic ECG records showed that with DSP treatment, the number and average duration of extrasystole in patients decreased significantly from 5.37 min once before treatment to 1.58 min once after it, a great difference before and after treatment, as shown in Table 1-17.

TABLE 1-17

Comparison of extrasystole frequency and duration in dynamic ECG record before and after treatment

| | extrasystole number | Cumulative time (min) | Average time of onset (mins/counts) |
|---|---|---|---|
| Before treatment | 95 | 510 | 5.37 |
| After treatment | 24 | 38 | 1.58* |

All onset times for patients in this group shortened. No toxic side effects were found. The drug is safe, suitable for long-term use, and efficient. It shows advantages and potential for broadening functions in the future.

2. Effects on Cardiac Arrhythmia (1) Treatment of Cardiac Arrhythmia

1. Subject. 46 patients with coronary heart disease and cardiac arrhythmia (including 39 males and 7 females) and 55 patients without heart disease but with cardiac arrhythmia (including 36 males and 19 females) were chosen.

2. Arrhythmia was confirmed by ECG and electrocardio-monitoring. All heartbeat irregularity medication in 5 half-life periods was stopped before treatment. DSP was given at doses of 10 tablets/medication, 3 times/day. ECG and arrhythmia are checked after 2 weeks of medication.

Results (1) Irregularity of heart rhythm in the coronary heart disease group before treatment is shown in Table 2-1.

TABLE 2-1

Comparison of irregularity of heart rhythm in the coronary heart disease group before and after treatment

| | Sinus bradycardia | Premature atrial beats | Premature atrioventricular junction beats | Premature ventricular beats | AVB | Bundle-branch block |
|---|---|---|---|---|---|---|
| Before treatment | 14 | 21 | 7 | 32 | 11 | 5 |
| After treatment | 3* | 5** | 2* | 8** | 4* | 3 |

Notes: Comparison before and after treatment,
*$P < 0.05$,
**$P < 0.01$.
Few patients have different kinds of heart rhythm irregularities at the same time.

(2) Irregularity of heart rhythm in control group before and after treatment is shown in Table 2-2.

TABLE 2-2

Irregularity of heart rhythm in control group before and after treatment

| | Sinus bradycardia | Premature atrial beats | Premature atrioventricular juction beats | Premature ventricular beats | AVB | Bundle-branch block |
|---|---|---|---|---|---|---|
| Before treatment | 8 | 16 | 4 | 23 | 6 | 4 |
| After treatment | 2* | 3** | 2 | 9* | 3 | 2 |

Notes:
Comparison before and after treatment,
*$P < 0.05$,
**$P < 0.01$.

Conclusion

The treatment effects of DSP on cardiac arrhythmia caused by coronary heart disease are significant. It is also helpful to those patients without heart disease. Its functions are: a) Calcification. DSP can reduce intracellular calcium concentration and prevent calcium overloading better than verapamil. B) Stabilizing the cell membrane. DSP can protect cardiac muscle and regulate heart rhythm. c) Removal of free radicals. D) Speeding up energy production and utilization. There is no relationship between chronic irregularity of heart rhythm and the addition of resistance and lack of energy supply.

(2) Long-Term Effects on Irregularity of Heart Rhythm Caused by Myocarditis and Cardiac Functions 1. Clinical samples. 120 patients with myocarditis were selected according to Whole Country Myocarditis Conference Standards, 1995. Patients took their own regular medication for one month and then were randomly divided into two groups with 60 patients per group. The DSP group (Treatment group) included 33 males and 27 females. The Di'ao Xinxuekang group (Control group) included 31 males and 29 females.

2. Method of treatment. DSP was given to the Treatment group, 10 tablets/medication, 3 times/day orally. Di'ao Xinxuekang Jiaonang was given to the Control group (made by the pharmaceutical factory of Chengdu Bio-tech Research Institute, Chinese Science Institute), 200 mg/medication, 3 times/day orally. Both medications lasted 2-6 months.

Results (1) Symptoms of both groups. There was significant improvement in palpitation, sense of suffocation, and difficulty breathing in both groups after treatment. The total clinical efficiencies of the treatment group and the control were 93% and 73%, respectively, as shown in Table 2-3.

TABLE 2-3

Comparison of efficacy for symptoms in two groups

| Group | n | Efficacy | Efficacy | Failure | Total Efficacy (%) |
|---|---|---|---|---|---|
| Treatment | 60 | 25 | 31 | 4 | 93.0 |
| Control | 60 | 17 | 27 | 16 | 73.0 |

Notes:
Comparison of the two treatments,
$P < 0.01$ (2) ECG treatment of two groups. There were no significant differences in the heart rhythm of the two groups after treatment. ST-T and T wave, premature atrial beats, and premature ventricular beats were improved, but the treatment group showed much more improvement than the control group, as shown in Table 2-4.

TABLE 2-4

Comparison of ECG results between the two groups

| Group | n | Efficacy | Efficacy | Failure | Total Efficacy (%) |
|---|---|---|---|---|---|
| Treatment | 60 | 24 | 32 | 4 | 93.0 |
| Control | 60 | 15 | 24 | 11 | 65.0 |

Notes:
Comparison of the 2 treatments,
$P < 0.01$ (3) Change in heart ultrasound in two groups. The ultrasound showed that the change in heart size was not significant before and after treatment. The pumping power of the left ventricle in patients in the treatment group increased from 48% to 62%, on average, after treatment. The contraction percentage of the left ventricular wall decreased from 46% to 18%, which was better than the control group, as shown in Table 2-5.

TABLE 2-5

Comparison of the change in heart ultrasound in patients in two groups before and after treatment

| | Treatment group | | Control group | |
|---|---|---|---|---|
| | Before treatment | After treatment | Before treatment | After treatment |
| Enlargement of heart/cases | 18 | 12 | 12 | 1 |
| Pumping power of left ventricle (%) | 48 | 62 | 49 | 52 |
| Abnormal Contraction of left ventricul wall (%) | 46 | 18 | 43 | 28 |

Notes:
Comparison of two treatments, $P > 0.05$

No significant differences were found in the two groups before and after treatment.

DSP and Di'ao Xinxuekang can both improve cardiac arrhythmia caused by myocarditis and heart malfunction, but DSP does a better job than Di'ao Xinxuekang. DSP can improve blood flow to the cardiac muscles, section ST and T wave in ECGs. In addition, DSP can also reduce platelet aggregation, and platelet viscosity. The results show that patients who take DSP in the long term enjoy relief from symptoms and low reoccurrence of myocarditis.

3. Reverse Function of DSP on Left Ventricular Hypertrophy (LVH)

This experiment explored the reverse function of DSP on LVH.

1. Subject and Method 1.1 Sample selection. All patients were selected from clinics and hospitals and do not have high blood pressure, coronary heart disease, myocardial disease, diabetes, or other heart diseases. LVH was confirmed by ultrasonic ECG. The patients were divided into two groups at random: 34 patients in the treatment group, including 21 males and 13 females; 20 patients in the control group, including 12 males and 8 females. There was no difference in age, sex, and medication in the two groups.

1.2 Method. DSP was given to the treatment group, 10 tablets/medication, 3 times/day. 50 mg Meiduoxin' an was given to the control group, 3 times/day. Each medication lasted 6-12 months. Other blood vessel medications were stopped during treatment. For comparison, the two groups were checked and results logged before and after treatment.

1.3 Types of measurements and standards. The heart ultrasound was checked by color doppler. The dilated Left Ventricular Interior Diameter (LVID) was measured. Interventricular septum thickness (IVST) and Left Ventricular Posterior Wall Thickness (LVPWT) were measured and calculated: Left Ventricular Mass (LVM)=$1.04 \times [(LVID+LVPWT+IVST)^3 - LVID^3] - 1.36$ and Left Ventricular Mass Index (LVMI)=LVM/Surface Area. LVH standard: a) IVST$\geq$12 mm; b) LVPWT$\geq$12 mm; c) LVMI$\geq$135 g/m$^2$ (male) or 110 g/m$^2$.

Results 2.1 Effects on LVH retreatment. IVST, LVPWT and LVMI in the treatment group decreased significantly ($P<0.05$ or 0.01), though the above standards also decreased in the control group. There were no significant treatment effects, as shown in Table 3-1.

TABLE 3-1

Comparison of LVH index in B-ultrasound in 2 groups before and after treatment

| Types | Treatment group | | Control group | |
|---|---|---|---|---|
| | Before treatment | After treatment | Before treatment | After treatment |
| LVID (mm) | 5.58 ± 0.59 | 5.21 ± 0.33* | 5.62 ± 0.64 | 5.59 ± 0.65 |
| IVST (mm) | 13.6 ± 1.3 | 10.9 ± 1.4** | 12.8 ± 1.6 | 12.4 ± 1.8 |
| LVPWT (mm) | 13.0 ± 1.7 | 11.0 ± 1.2* | 12.6 ± 1.5 | 11.9 ± 1.6 |
| LVM (g) | 252.6 ± 58.2 | 198.7 ± 30.96** | 238.6 ± 59.8 | 229.8 ± 42.5 |
| LVMI (g/m$^2$) | 136.9 ± 22.6 | 108.9 ± 18.6* | 139.8 ± 19.3 | 135.7 ± 20.6 |

Notes:
*Comparison of results before treatment, $P < 0.05$, **Comparison of results before treatment, $P < 0.01$ 2.2 Effects on cardiac function parameters. DSP can increase SV, CI, VPE, and EWK, and decrease VER, TPR, and HOV. This shows that it can reduce heart burden and add new functions to the heart, as shown in Table 3-2.

TABLE 3-2

Comparison of cardiac function index of two groups before and after treatment

| Types | Treatment group | | Control group | |
|---|---|---|---|---|
| | Before treatment | After treatment | Before treatment | After treatment |
| Pulse Volume (SVml/pulse) | 68.32 ± 1.55 | 79.87 ± 1.92* | 70.16 ± 1.52 | 69.68 ± 1.20 |
| Heart Index (CL/counts/m$^2$) | 3.20 ± 0.78 | 3.98 ± 0.39* | 3.54 ± 0.66 | 3.52 ± 0.43 |
| Ventricular Efficient Pumping (VPE kg/Pulse) | 1.6210 ± 0.16 | 1.8825 ± 0.64** | 1.5814 ± 0.12 | 1.6627 ± 0.33 |
| Ventricular Ejection-Resistance (VER) | 238 ± 1.64 | 150 ± 1.28** | 240 ± 1.32 | 238 ± 1.56 |
| Left Ventricular Cardiac Energy Efficacy (EWK) | 0.244 ± 0.084 | 0.297 ± 0.021** | 0.254 ± 0.112 | 0.271 ± 0.03 |
| Peri-Resistance (TPR dyne sec$^2$/m$^2$) | 984.78 ± 86.01 | 902.35 ± 54.16** | 1103.66 ± 74.26 | 986.58 ± 78.27 |
| Heart oxygen consumption volume (HOV) | 44.954 ± 1.5 | 41.210 ± 1.2* | 43.167 ± 1.1 | 42.164 ± 0.9 |

Notes:
*Comparison of results before treatment, $P < 0.05$, **Comparison of result before treatment, $P < 0.01$ 2.3 Effects on blood pressure and heart rhythm. DSP can decrease heartbeat, average arterial pressure and RPP, and so eliminate the triggering factors of LVH, as shown in Table 3-3.

TABLE 3-3

Changes in heart rate and blood pressure in the two groups before and after treatment

| Types | Treatment group | | Control group | |
|---|---|---|---|---|
| | Before treatment | After treatment | Before treatment | After treatment |
| Heart rete | 80.2 ± 12.18 | 72.8 ± 8.64** | 81.00 ± 10.20 | 75.81 ± 8.13* |
| Average arterial pressure | 118.0 ± 9.11 | 101.11 ± 5.50** | 116.28 ± 10.21 | 112.92 ± 5.8 |
| RPP | 116.42 ± 13.57 | 98.46 ± 11.29** | 118.55 ± 12.88 | 108.86 ± 10.64 |

Notes:
*Comparison of results before treatment, $P < 0.05$, **Comparison of results before treatment, $P < 0.01$ 2.4 Effects on parameters of blood viscosity. DSP can decrease blood viscosity, prevent platelet aggregation and blood vessel resistance, and eliminate the triggering factors of LVH, as shown in Table 3-4.

TABLE 3-4

Changes in blood viscosity of the two groups before and after treatment

| Types | Treatment group | | Control group | |
|---|---|---|---|---|
| | Before treatment | After treatment | Before treatment | After treatment |
| Blood viscosity (ηb) | 4.714 ± 0.34 | 3.680 ± 0.12** | 4.773 ± 0.36 | 4.631 ± 0.24 |
| Blood reduction (ηr) | 7.889 ± 0.030 | 6.326 ± 0.14** | 7.416 ± 0.12 | 7.385 ± 0.18 |
| Plasma viscosity (ηp) | 2.532 ± 0.13 | 1.400 ± 0.08* | 2.486 ± 0.16 | 2.495 ± 0.12 |

Notes:
*Comparison of results before treatment, $P < 0.05$, **Comparison of results before treatment, $P < 0.01$ 2.5 Effects on standards of atherosclerosis. DSP increases APOA-1 (Apoprotein A), SOD, and APOB$^{-100}$ and decreases WsFs, which can prevent atherosclerosis and bring about anti-aging functions, as shown in Table 3-5.

TABLE 3-5

Comparison of indexes of atherosclerosis in two groups before and after treatment

| Types | Treatment group | | Control group | |
|---|---|---|---|---|
| | Before treatment | After treatment | Before treatment | After treatment |
| APOA$^{-1}$ (mg/ml) | 108.9 ± 46.8 | 134.3 ± 50.6** | 122.4 ± 48.4 | 130.6 ± 46.9 |
| APOB$^{-100}$ (mg/ml) | 161.2 ± 62.6 | 120.8 ± 52.4* | 153.4 ± 66.2 | 148.9 ± 53.8 |
| WsFs (u) | 17.8 ± 7.9 | 13.5 ± 2.4** | 16.9 ± 8.6 | 15.8 ± 2.2 |
| SOD (u/ml) | 272.86 ± 110.30 | 361.87 ± 92.44** | 286.31 ± 99.71 | 302.13 ± 96.25 |

Notes:
*Comparison of results before treatment, $P < 0.05$, **Comparison of result before treatment, $P < 0.01$ 2.6 Effects on nail bed microcirculation. DSP can significantly improve the blood circulation and blood flow and increase the oxygen-carrying capacity of red blood cells, as shown in Table 3-6.

TABLE 3-6

Comparison of the nail bed micro-circulation standard in two groups before and after treatment

| Types | Treatment group | | | | Control group | | | |
|---|---|---|---|---|---|---|---|---|
| | Before treatment | | After treatment | | Before treatment | | After treatment | |
| Flow speed (mm/s) | 0.126 ± 0.413 | | 0.332 ± 0.111* | | 0.125 ± 0.430 | | 0.185 ± 0.419 | |
| Blood vessel heterozygosity (%) | 64.21 ± 37.32 | | 63.92 ± 37.66 | | 63.86 ± 31.85 | | 62.88 ± 34.22 | |
| Fluid cloudiness | 28 | 82.4% | 5 | 14.8%** | 18 | 52.9% | 15 | 44.1% |
| Dotted-line state | 6 | 17.6% | 29 | 85.2%** | 16 | 47.1% | 19 | 55.9% |

Notes:
*Comparison of results before treatment, $P < 0.05$,
**Comparison of results before treatment, $P < 0.01$ The above experiment shows that DSP prevents damage caused by free radicals, prevents atherosclerosis, improves blood circulation, decreases blood viscosity and exterior blood vessel resistance, and regulates compliance of cardiac muscles to reverse LVH.

4. DSP Treatment for High Blood Pressure (1) Effects on Structure and Functions of Heart in Patients with High Blood Pressure and Coronary Heart Disease 1. Subject. 140 patients with high blood pressure and coronary heart disease for 4-15 years were selected. The ratio of males to females is 5:1.

2. Method. No angina- and blood pressure-lowering medications were taken 1 week before treatment. A placebo was taken 3 times/day for 1 week, followed by 10 DSP tablets, 3 times/day. Each medication was taken for 8 weeks.

3. Standards. Static ECG, blood pressure, heartbeat, clinical symptoms and other undesirable responses; the levels of: Epinephrine (E), Non-Epinephrine (NE), Atrial Natriuretic Factor (ANF), endothelins (ET), Nitrogen Monoxide (NO); the structure and functions of the Left Ventricle (Left Ventricular Dilated diameter, LVDd, Interventricular space, IVS, left ventricular posterior wall, PWT, and Left Ventricular Mass Index LVMI).

4. Standards of measurement. The structure and function of the left ventricle was measured by colored ultrasonic doppler, and the LDVd, IVS and PWT were found. LVMI was calculated according to the equation: LVMI={1.04 [LDVd+IVS+PWT]$^3$−13.6}$^2$/surface area, male>125 g/m$^2$, female>110 g/m$^2$ are regarded as LVH. According to the Teichholz equation and the frequency of blood flow in the aorta, cardiac output (CO) and ejection fraction (EF) were calculated, and A peak velocity (DAV), E peak velocity (DEV) and A/E ratio were measured according to the greatest blood flow through the biscupid valve. The above results were taken from the average value of 3 trials.

5. Statistics: Results are in terms of X±s. Using matching t statistic testing before and after treatment.

Results (1) Symptoms of angina and ECG treatment (See Table 4-1):

TABLE 4-1

| Types | Sample Number | Obvious Efficacy (%) | Efficacy (%) | Failure (%) | Total Efficacy (%) |
|---|---|---|---|---|---|
| Symptoms of Angina | 140 | 48 | 80 | 12 | 91.4 |
| ECG section ST | 100 | 40 | 32 | 28 | 80 |

(2) Change in blood pressure and heartbeat. Heartbeat slowed to 76.24±9.37 counts/min ($P<0.01$). Systolic pressure (SBP) dropped from 20.9±1.71 Kpa to 19.40±1.74 Kpa, diastolic pressure (DBP) dropped from 12.07±1.99 Kpa to 10.69±0.70 Kpa.

(3) Change in ANP, ET, NO, NE, E before and after treatment (See Table 4-2): DSP can lower ET, ANP, NE, E but raises NO.

TABLE 4-2

|  | AUP (pg/L) | ET (pg/L) | NO (mol/L) | NE (pg/L) | E (pg/L) |
|---|---|---|---|---|---|
| Before treatment | 132.7 ± 3.84 | 48.9 ± 11.8 | 10.97 ± 4.3 | 0.43 ± 0.02 | 0.098 ± 0.02 |
| After treatment | 93.8 ± 27.5** | 29.4 ± 0.6* | 16.7 ± 8.6* | 0.2 ± 0.03* | 0.07 ± 0.01* |

Notes:
Comparison before and after treatment,
*$P < 0.05$,
**$P < 0.01$ (4) Effects on structure of left ventricle (See Table 4-3.) DSP can lower IVS, PWT and LVMI.

TABLE 4-3

|  | LVDd (mm) | IVS (mm) | PWT (mm) | LVMI (g/m$^2$) |
|---|---|---|---|---|
| Before treatment | 46.9 ± 2.67 | 12.83 ± 2.48 | 11.93 ± 1.51 | 132.89 ± 28.66 |
| After treatment | 40.2 ± 3.09* | 9.82 ± 1.44** | 8.28 ± 1.36* | 121.58 ± 26.84** |

Notes:
Comparison before and after treatment,
*$P < 0.05$,
**$P < 0.01$ (5) Effects on functions of left ventricle (See Table 4-4). DSP can obviously improve diastolic function of the left ventricle.

TABLE 4-4

|  | EF (%) | DAV (m/s) | DEV (m/s) | A/E |
|---|---|---|---|---|
| Before treatment | 50.14 ± 11.02 | 0.75 ± 0.13 | 0.73 ± 0.19 | 1.21 ± 0.32 |
| After treatment | 51.47 ± 9.81 | 0.57 ± 0.41* | 0.89 ± 0.12* | 0.98 ± 0.34** |

Notes:
Comparison before and after treatment,
*$P < 0.05$,
**$p < 0.01$ (6) Undesirable responses: No undesirable responses were observed in these group.

Discussion

The experiment shows that DSP can stop and improve LVH and dilate the left ventricle, which can then lower blood pressure and combat angina.

significant difference in the weight index of the two groups both before and after treatment. After 4 weeks of treatment, the insulin level in the DSP group was lower than before (P<0.05). Insulin/blood glucose ratio was also lower than before treatment. However, there was no difference in insulin level and insulin/blood glucose ratio in the control group both before and after treatment.

TABLE 4-6

Comparison of related parameters in the hypertension-with-pure-amino-chloride-horizons group and the DSP group before and after treatment

| Relative data | Amlodipine plus DSP group (n = 40) | | Amlodipine group (n = 40) | |
|---|---|---|---|---|
| | Before treatment | After treatment | Before treatment | After treatment |
| Blood glucose (mmol) | | | | |
| Empty | 5.26 ± 0.84 | 5.01 ± 0.78 | 5.19 ± 0.56 | 5.27 ± 0.59 |
| 60 min | 9.63 ± 1.94 | 7.26 ± 0.31 | 9.86 ± 0.65 | 9.76 ± 0.52 |
| 120 min | 7.64 ± 0.80 | 6.21 ± 0.15 | 7.69 ± 0.81 | 8.01 ± 0.76 |
| Blood insulin (mU/L) | | | | |
| Empty | 26.24 ± 1.83 | 20.32 ± 1.57 | 25.34 ± 1.74 | 25.31 ± 1.73 |
| 60 min | 126.79 ± 1.90 | 99.66 ± 2.00 | 122.01 ± 1.91 | 121.65 ± 1.89 |
| 120 min | 90.53 ± 1.75 | 71.42 ± 1.96 | 91.62 ± 1.96 | 92.56 ± 1.66 |
| Insulin/ blood glucose ratio | 5.06 ± 1.29 | 4.19 ± 0.93 | 5.24 ± 1.01 | 5.18 ± 1.07 |

(2) Effects on Plasma ET and Anti-Insulin Function with Hypertension

1. Aims. Examine the effects of DSP on plasma ET and anti-insulin function in patients with hypertension.

2. Subject. 80 patients with satisfactory results after 1 week of treatment with Amlodipine were selected.

3. Method. The 80 patients were divided into 2 groups: the Control group, with normal treatment, and the DSP group, with 10 DSP tablets, 3 times/day. Testing lasted 4 weeks.

4. Results. (1) Change in plasma ET and blood pressure before and after treatment (See Table 4-5.). After treatment, plasma ET in both group was lower, (P<0.05), especially that of the DSP group (P<0.05).

TABLE 4-5

Comparison of related data between the Amlodipine group and the Amlodipine plus DSP group before and after treatment

| Relative data | Amlodipine plus DSP group (n = 40) | | Amlodipine group (n = 40) | |
|---|---|---|---|---|
| | Before treatment | After treatment | Before treatment | After treatment |
| Weight Index (kg/m²) | 23.39 ± 1.82 | 23.37 ± 1.67 | 23.95 ± 2.01 | 23.96 ± 1.92 |
| SBP (kPa) | 21.43 ± 1.69 | 17.39 ± 1.44 | 21.40 ± 1.67 | 18.09 ± 1.55 |
| DBF (kPa) | 12.72 ± 0.58 | 11.01 ± 0.59 | 12.85 ± 0.54 | 11.25 ± 0.68 |
| Plasma ET (ng/L) | 56.4 ± 6.78 | 38.7 ± 4.62 | 57.2 ± 7.31 | 42.6 ± 4.78 |

(2) Comparison of insulin level and insulin reactivity before and after treatment (See Table 4-6). There was no Conclusion Besides controlling blood pressure efficiently, other important steps for treating high blood pressure include: increasing the reactivity of insulin, lowering insulin level, and improving ET function in blood vessels. DSP is helpful because it also lowers blood pressure.

3. Treatment of Hyperlipidemia (1) Treatment of Hyperlipidema

Research into the treatment of hyperlipidemia and atherosclerosis with DSP in comparison to low-dosage aspirin.

1. Subject and Method 1.1 Sample. 53 patients were divided into 2 groups, at random: 25 patients in Treatment group (DSP group), and 28 patients in Control group (aspirin group).

1.2 Method: DSP was given to the treatment group, 10 tablets/day, 3 times/day. The medication lasted for 6 months. 50 mg enteric aspirin was given to the Control group, 1 time/day orally.

1.3 Standard. a) Measurement of IMT (Arterial tunica intima-tunica media). The horizontal and vertical transactions of the whole-length aorta, carotis communis, exterior artery, and subclavial artery were checked 1, 2, 3, and 6 months after treatment. The thickest part of the IMT was measured and recorded. b) Blood flow included whole blood high-viscosity (hHb), whole blood low-viscosity (hLb), plasma viscosity (hP), Aggregation Index of Red blood cells (AIR) etc. c) Measurement of blood lipoprotein included Total blood Cholesterol (TC) and Triglycerides (TG). D) Statistical treatment by matching t statistic testing.

Results (1) The medication lasted for 6 months, and the results of the IMT test are shown in Table 5-1. The carotis communis becames thinner in the Treatment group (P<0.05), but there was no observable change in that of the control group.

TABLE 5-1

Measurement of Arterial IMT in 2 groups after treatment

| Group | | Sample number | IMT (mm) |
|---|---|---|---|
| DSP | Before treatment | 41 | 2.2 ± 0.7 |
| | After treatment | 41 | 2.1 ± 0.6* |
| Aspirin | Before treatment | 43 | 2.0 ± 0.8 |
| | After treatment | 43 | 2.1 ± 0.7 |

Notes:
Comparison of results before treatment in the same group, *P < 0.05

(2) Blood flow results are shown in Table 5-2. Blood viscosities in the two groups decreased after 6 months on medication, and there were no significant differences in the level of decrease, (P>0.05).

TABLE 5-2

Results of blood flow in two groups of patients before and after treatment

| Group | Sample Number | η Hb (mpa · s) | η Lb (mpa · s) | η P (mpa · s) | AIR |
|---|---|---|---|---|---|
| DSP | | | | | |
| Before treatment | 25 | 6.23 ± 1.67 | 10.92 ± 2.21 | 1.95 ± 0.08 | 1.79 ± 0.13 |
| After treatment | 25 | 4.35 ± 1.02* | 8.30 ± 1.14* | 1.77 ± 0.08* | 1.39 ± 0.11* |
| Aspirin | | | | | |
| Before treatment | 28 | 6.12 ± 1.56 | 10.38 ± 1.96 | 1.89 ± 0.12 | 1.82 ± 0.17 |
| After treatment | 28 | 4.28 ± 1.07* | 8.21 ± 1.03* | 1.67 ± 0.07* | 1.40 ± 0.10* |

Notes:
Comparison of results before treatment in the same group,
*P < 0.01

(3) Results of blood lipoprotein testing are shown in Table 5-3, TC and TC level decrease significantly in DSP group after 6 months of medication (P<0.01), and there is no observable difference in the control group.

TABLE 5-3

Results of blood lipoprotein testing before and after treatment in the two groups

| Group | | Sample Number | ηHb (mpa · s) | ηP (mpa · s) |
|---|---|---|---|---|
| DSP | Before treatment | 41 | 6.08 ± 1.5 | 1.91 ± 0.68 |
| | After treatment | 41 | 4.91 ± 1.44* | 1.54 ± 0.56* |
| Aspirin | Before treatment | 43 | 6.10 ± 1.67 | 1.83 ± 0.82 |
| | After treatment | 43 | 5.92 ± 1.81 | 1.76 ± 0.94 |

Notes:
Comparison of results before treatment in the same group, *P < 0.01

Discussion

This research shows that DSP can significantly lower blood lipoprotein level and improve blood flow, especially by the thinning of IMT after treatment. It explains how this drug can prevent atherosclerosis besides providing the above functions.

(2) Observation of treatment of senior group coronary heart disease, angina with high blood viscosity 1. Sample. 48 patients with angina and high blood viscosity were selected, including 39 males and 9 females; 41 patients had stable angina, and 7 patients had unstable angina.

2. Method of medication. All other medications were stopped 2 weeks before DSP administration. DSP was given under lingua, 10 tablets/medication, 3 times/day. The medication lasted 4 weeks. Blood was collected though the superior venous cava the morning before ingestion to test blood flow standards and observe angina conditions and side effects after treatment.

Results (1) Angina improvement. 25 patients were regarded as obvious efficacy (52.0%), 16 were efficacy (33.3%), 7 were failures (14.5%).

(2) Changes in blood flow standards are shown in Table 5-4.

TABLE 5-4

Change in blood flow standards

| Types | Before treatment | After treatment | P value |
|---|---|---|---|
| Whole high blood-viscosity value | 6.76 ± 3.22 | 4.53 ± 1.06 | <0.01 |
| Whole high blood viscosity value | 9.93 ± 3.42 | 7.81 ± 1.83 | <0.01 |
| Plasma viscosity | 1.91 ± 0.18 | 1.70 ± 0.16 | <0.05 |
| Erythrocyte hematocrit | 0.44 ± 0.08 | 0.43 ± 0.07 | >0.05 |

(3) Observation. 1 out of 48 patients showed serious side effects, but no bleeding or headache. 3 patients suffered from stomachaches after the third day of medication. Symptoms disappeared if the medication was taken after meals. 1 patient suffered from a swollen head. The symptoms disappeared after continuous treatment.

Conclusion

DSP is safe and effective for senior patients with coronary heart disease with angina and high blood viscosity.

6. Treatment for Hyperviscosity Syndrome (HS)

Hyperviscosity Syndrome (HS) is a pathobiological concept, a syndrome caused by one or more blood viscosity factor(s). It can lead to lack of blood supply, hypoxia, blocking, etc. in the heart, brain and kidneys. DSP offers the best results in HS treatment.

There were 41 patients in this experiment, including 23 males and 18 females, aged 39-68. The average age was 50.7. The primary disease in this group was II-phase hypertentive disease. 22 patients had hypertentive disease and hypertentive nephrosis, 9 had cerebral infraction, 13 had coronary heart disease; 19 patients had nephrotic syndrome. DSP was given, 10 tablets/medication, 3 times/day and the medication lasted for 4 weeks. t statistic testing was used for comparison before and after treatment.

Results

After the normal 28 days of medication, HS symptoms such as nausea, lack of energy, breath holding, anxiety, etc. related to coronary heart disease, cerebral infraction, and kidney disease disappeared gradually. Blood pressure was lowered, and blood circulation improved. TC, TG, Apo-B dropped, and HDLC and Apo-A1 rose. All levels of hemorheology markers dropped. Renal Blood flow increased, and renal function improved. Urine protein decreased, and cardiac improved. See Tables 6-1, 6-2, 6-3.

TABLE 6-1

Change in blood lipoproteins and apoproteins before and after HS (x ± s)

|  | TC (mmol/L) | TG (mmol/L) | HDLC (mmol/L) | Apo-A1 (g/L) | Apo-B (g/L) |
| --- | --- | --- | --- | --- | --- |
| Before treatment | 8.07 ± 1.45 | 2.41 ± 1.32 | 1.21 ± 0.29 | 1.27 ± 0.18 | 1.58 ± 0.46 |
| After treatment | 6.26 ± 1.53 | 2.03 ± 1.46 | 1.37 ± 0.31 | 1.48 ± 0.19 | 1.06 ± 0.45 |
| P value | <0.01 | <0.01 | <0.01 | <0.01 | <0.01 |

TABLE 6-2

Change in blood flow before and after HS (x ± s)

| Types | Before treatment | After treatment | P value |
| --- | --- | --- | --- |
| Whole blood viscosity (high-density) | 7.94 ± 1.28 | 5.06 ± 1.19 | <0.01 |
| Whole blood viscosity (low-density) | 11.87 ± 1.69 | 8.07 ± 1.25 | <0.01 |
| Plasma viscosity | 1.96 ± 0.37 | 1.48 ± 0.16 | <0.01 |
| Hematocrit | 46.85 ± 3.11 | 42.79 ± 3.15 | <0.01 |
| Aggregation index of red blood cells | 2.08 ± 0.14 | 1.39 ± 0.13 | <0.01 |

TABLE 6-3

Change in blood pressure, heart rate and cardiac function before and after HS

|  | SBP(kPa) | | DBP(kPa) | | Heartbeat (times/min) | | Cardiac functions E/A |
| --- | --- | --- | --- | --- | --- | --- | --- |
| Before treatment | 22.8 | 1.6 | 14.9 | 1.5 | 81.2 | 7.5 | <1 |
| After treatment | 15.9 | 1.4 | 11.2 | 1.3 | 73.9 | 6.4 | >1 |
| P value | <0.01 | | <0.01 | | <0.01 | | |

7. Treatment for Acute Myocardial Infarction (AMI)

Effects on Blood Serum Troponin in Patients with AMI

1. Subject. 56 patients with AMI, including 34 males and 22 females, aged 40-70 were selected. Patients were divided in a 1:1 ratio into two groups: 28 patients each in the treatment group and the control group. The Control group consisted of 40 healthy people tested at random, including 23 males and 17 females, aged 42-73.

2. Method of medication. Treatment group: DSP was given, 10 tablets, 3 times/day, for 2 weeks; Control group: Western medical treatment was used (i.e. absolute bed rest, oxygen intake, maintaining of the stool in a soft and smooth state). The Control group also took 10 mg Isordil orally, 3 times/d; 75 mg enteric aspirin, 1 time/d, 12.5 mg Kaibotong, 2 times/d, 5 mg glyceryl Trinitrate+polarization solution, mild titration, 1 time/d.

3. Observation method. 2 ml of blood was collected from the inferior vena cava of each patient 6 hrs, 12 hrs, 1 day, 3 days, 5 days, 7 days, 9 days, 11 days, and 13 days after patients entered the hospital. The blood was tested by one-step sandwich enzyme immunoassay.

Results (1) The blood serum TnT concentration in a normal person should be evenly distributed, and the normal value should be 0.26±0.14 ug/L. Those with values higher than 0.38 ug/L were regarded as significantly increased.

(2) Results of blood serum TnT concentration in both groups at different onset times are shown in Table 7-1. TnT concentrations in the two groups were evenly distributed. The serum TnT in the treatment group rose 3-6 hrs after onset, and reached its peak on the 47th day, maintained a high level for 9 days, then returned to normal on the 11th day. Serum TnT concentration in the Control group rose 4-6 hrs after onset, reached its peak on the 48$^{th}$ day, and maintained a high level for 10 days. It returned to normal on the 12th day.

TABLE 7-1

Results of serum TnT concentration in the two groups at different onset times (ng/L)

| Group | No | 0 h | 6 h | 12 h | 1 d | 3 d | 5 d | 7 d | 9 d | 11 d | 13 d |
| --- | --- | --- | --- | --- | --- | --- | --- | --- | --- | --- | --- |
| With treatment | 28 | 0.29 ± 0.17 | 0.58 ± 0.21 | 0.89 ± 0.36 | 3.27 ± 0.93 | 7.65 ± 1.36 | 5.39 ± 1.22 | 2.85 ± 0.81 | 0.48 ± 0.27 | 0.28 ± 0.13 | 0.22 ± 0.12 |

TABLE 7-1-continued

Results of serum TnT concentration in the two groups at different onset times (ng/L)

| Group | No | 0 h | 6 h | 12 h | 1 d | 3 d | 5 d | 7 d | 9 d | 11 d | 13 d |
|---|---|---|---|---|---|---|---|---|---|---|---|
| Control group | 28 | 0.28 ± 0.15 | 0.67 ± 0.26 | 0.95 ± 0.35 | 4.03 ± 1.12 | 9.64 ± 1.79 | 7.13 ± 1.42 | 4.28 ± 1.20 | 1.63 ± 0.68 | 0.39 ± 0.17 | 0.25 ± 0.14 |

(3) Analysis of serum TnT results in the Treatment group and the Control group is shown in Table 7-2. The peak value in the Treatment group is much lower than that of the Control group ($P<0.01$). The duration of TnT elevation and the time required to return to normal were significantly shorter than those in the Control group ($P<0.05$). No significant difference was observed in the time required to reach the peak in both groups.

TABLE 7-2

Result analysis of serum TnT in the two groups

| Group | Sample Number | Peak value (ug/L) | Time required to reach the peak(d) | Rising time (d) | Time required to return to normal value (d) |
|---|---|---|---|---|---|
| Treatment group | 28 | 8.96 ± 1.57 | 47.21 ± 2.18 | 9.37 ± 1.24 | 10.96 ± 1.39 |
| Control group | 28 | 11.02 ± 2.13 | 48.38 ± 2.75 | 10.16 ± 1.36 | 11.87 ± 1.48 |

Conclusion: DSP can improve blood circulation by dilating coronary arteries, saving cardiac muscle, minimizing the infarction area, and protecting myocardial cells. Therefore, DSP can protect cardiac muscles in the early stages of AMI. It is a convenient medication with no side effects, which is recommended in the clinical field.

8. Effects on Treatment of Cerebral Infarction Treatment of Cerebral Infarction

All cases are confirmed by CT brain scan. Patients were divided into random groups at a 2:1 ratio. The 102 patients in Group A were given DSP, 10 tablets/medication, once per 6 hrs through the nose and given additional treatments according to their level of illness. These additional treatments included dehydrating agents, anti-infectants, substances to maintain water and electrolyte balance, acupuncture, moxibustion, chirapsia, etc.) Group B received the same treatment except DSP. The medication lasted for 4 weeks in both groups.

Treatment standards. Marks were given according to the level of neurologic impairment and according to clinical efficacy standards.

Basic recovery. Level of disablement is grade 0

(1) Obvious efficacy. Functional damage marks were reduced 21 marks or more, and the level of disablement was grade 1-3.

(2) Efficacy. Functional damage marks were reduced 8-20 marks.

(3) Failure. Functional damage marks were reduced or less than 8 marks were given.

(4) Worsening. 9 or more functional damage marks were given.

Results 98 patients with a total efficacy of 96.08% were found in Group A after treatment. 37 patients with a total efficacy of 72.55% were found in Group B after treatment, according to $X^2$ statistic testing, $P<0.001$. This shows that the treatment results for Group A were much better than that of Group B. See Table 8-1.

TABLE 8-1

Comparison of results in the two groups (%)

| Group | Sample number | Basic recovery | Obvious Efficacy | Efficacy | Failure | Worsen cases | Total Efficacy |
|---|---|---|---|---|---|---|---|
| Group A | 102 | 14 (13.72) | 41 (40.20) | 43 (42.16) | 4 (3.92) | 0 (0) | 98 (96.08) |
| Group B | 51 | 5 (9.80) | 14 (27.45) | 18 (35.30) | 11 (21.57) | 3 (5.88) | 37 (72.55) |

Notes:
Total Efficacy tested by $X^2$ statistic testing in the two groups,
X2 = 18.133,
P < 0.001

The use of DSP to treat low blood supply to the brain, cerebral infarction and internal bleeding is very efficient.

9. Effects on Blood Micro-Circulation

Patients with coronary heart disease have a disorder of hemorheology not only in their systemic circulations, but also in different levels of micro-circulation. Recently, most patients with coronary heart disease have lower than half the normal renewal rate by micro-circulation standards. It shows that patients with coronary heart diseases also get microcirculation disorders. Nail wall or bulbar conjunctiva micro-circulation are used as observation start points for examining total body micro-circulation.

(1) Effects on Nail wall micro-circulation. See Table 3-6.

(2) Effects on bulbar conjunctiva micro-circulation Effects of DSP on patients with coronary heart disease, bulbar conjunctiva micro-circulation and thrombo-elasticity chart.

The effects of DSP on patients with coronary heart disease bulbar conjunctiva micro-circulation and thrombo-elasticity chart by compared with Suxiao Jiuxin Wan are discussed.

1. Sample. 120 patients are selected who have coronary heart disease and complain primarily of a congested feeling in their chests, who experience onset coronary heart disease-angina twice or more per week. They are divided into groups at random: a) 30 patients in the low-dosage DSP group. b) 30 patients in the medium-dosage DSP group. c) 30 patients in the high-dosage DSP group. d) 30 patients in the Suxiao Jiuxin Wan control group.

2. Method. DSP and Suxiao Jiuxin Wan were taken orally. The dosages are taken in the following order; 5 tablets/time, 10 tablets/time, 15 tablets/time, 10 tablets/time in the control group. No other unrelated medications are taken within 2 hrs after treatment. The bulbar conjunctiva micro-circulation and thrombo-elasticity charts are checked after 2 hrs, then rechecked for changes in different standards of bulbar conjunctiva micro-circulation at 10, 20, 30, 60, 90, 120, and 240 mins post treatment. Patients are checked for changes in thrombo-elasticity after 240 mins.

3. Standards: (1) testing of bulbar conjunctiva micro-circulation: Using a multifunctional microscope, the state of bulbar conjunctiva micro-circulation of the temporal left eye is magnified 50 times and observed. Sharp blood flow is chosen, blood capillaries and veins are recorded. The diameter and blood flow velocity of blood capillaries and veins by the PC processing system of microcirculation image (MCMP). Blood flow in capillary vessels is calculated, [blood flow volume=$\pi \times$(diameter of blood vessel/2)$^2 \times$ blood flow velocity]. All values used before treatment in both groups were counted as 100%.

(2) Testing of thrombo-elasticity. Using the thrombo-elasticity chart, physical changes in platelet aggregation and their dissolving process are observed. The main standards were reaction time(r), aggregation time(k), the maximum amplitude of thrombo-elasticity chart (ma), and thrombolic cutting-velocity rate ($\epsilon$).

Results (1) Effects on patients with coronary heart disease bulbar conjunctiva micro-circulation, see Tables 9-1, 9-2, 9-3, 9-4.

TABLE 9-1

Effects on diameter of capillary vessels in patients (M ± SD)

| | Low dosage (n = 30) | Medium dosage (n = 30) | High dosage (n = 30) | Control group (n = 30) |
|---|---|---|---|---|
| Before treatment | 100 | 100 | 100 | 100 |
| 10 mins after treatment | 104.45 ± 9.85 | 131.78 ± 9.38 | 141.27 ± 8.45 | 134.31 ± 9.32 |
| 20 mins | 114.36 ± 8.76 | 146.89 ± 9.91 | 156.72 ± 9.87 | 142.71 ± 9.65 |
| 30 mins | 119.32 ± 9.34 | 154.21 ± 9.43 | 178.56 ± 9.11* | 138.12 ± 9.88 |
| 60 mins | 121.66 ± 8.23 | 156.57 ± 8.36* | 198.34 ± 9.36* | 127.85 ± 9.13 |
| 90 mins | 103.26 ± 8.89 | 146.11 ± 9.12* | 186.46 ± 9.89* | 110.00 ± 9.00 |
| 120 mins | 109.37 ± 8.38 | 123.45 ± 9.21* | 143.78 ± 9.11* | 100.11 ± 7.89 |
| 240 mins | 101.67 ± 7.32 | 119.9 ± 6.98 | 127.72 ± 8.11 | 101.00 ± 7.93 |

Comparison with control group, *P < 0.05

TABLE 9-2

Effects on diameter of capillary vessels in patients (M ± SD)

| | Low dosage (n = 30) | Medium dosage (n=30) | High dosage (n = 30) | Control group (n = 30) |
|---|---|---|---|---|
| Before treatment | 100 | 100 | 100 | 100 |
| 10 mins After treatmen | 99.76 ± 5.36 | 90.31 ± 9.11 | 85.12 ± 8.21 | 88.67 ± 5.12 |
| 20 mins | 9.34 ± 8.56 | 87.34 ± 8.87 | 81.46 ± 8.81 | 86.71 ± 7.21 |
| 30 mins | 96.12 ± 9.56 | 81.35 ± 9.11 | 76.34 ± 9.22* | 89.56 ± 7.33 |
| 60 mins | 97.66 ± 9.21 | 79.11 ± 8.81* | 75.74 ± 9.12* | 91.56 ± 9.31 |
| 90 mins | 99.36 ± 8.81 | 89.37 ± 8.85* | 83.34 ± 7.89* | 96.45 ± 9.91 |
| 120 mins | 101.3 ± 8.21 | 95.55 ± 9.31 | 87.36 ± 8.21* | 97.12 ± 7.88 |
| 240 mins | 104.8 ± 7.32 | 98.91 ± 6.56 | 96.72 ± 8.14 | 98.00 ± 7.56 |

Comparison with control group, *P < 0.05

TABLE 9-3

Effects on blood flow velocity in capillary vessels in patients (M ± SD)

|  | Low dosage (n = 30) | Medium dosage (n = 30) | High dosage (n = 30) | Control group (n = 30) |
|---|---|---|---|---|
| Before treatment | 100 | 100 | 100 | 100 |
| 10 mins After treatment | 104.05 ± 5.36 | 124.31 ± 9.12 | 85.12 ± 8.21 | 130.33 ± 8.86 |
| 20 mins | 114.34 ± 8.81 | 136.34 ± 8.11 | 81.46 ± 8.81 | 148.71 ± 7.32 |
| 30 mins | 117.10 ± 7.34 | 148.56 ± 8.87 | 76.34 ± 9.22* | 139.66 ± 8.11 |
| 60 mins | 121.56 ± 6.78 | 136.13 ± 8.56* | 75.74 ± 9.12* | 133.34 ± 8.87 |
| 90 mins | 109.34 ± 6.69 | 129.73 ± 8.11* | 83.34 ± 7.89* | 118.21 ± 8.56 |
| 120 mins | 101.34 ± 7.67 | 118.97 ± 8.78 | 87.36 ± 8.21* | 112.34 ± 6.85 |
| 240 mins | 108.10 ± 8.95 | 110.37 ± 7.87 | 96.72 ± 8.14 | 108.87 ± 7.89 |

Comparison with control group, *$P < 0.05$

TABLE 9-4

Effects on blood flow volume in capillary vessels in patients (M ± SD)

|  | Low dosage (n = 30) | Medium dosage (n = 30) | High dosage (n = 30) | Control group (n = 30) |
|---|---|---|---|---|
| Before treatment | 100 | 100 | 100 | 100 |
| 10 mins After treatment | 119.12 ± 4.56 | 126.71 ± 8.81 | 137.67 ± 8.81 | 123.21 ± 8.56 |
| 20 mins | 121.56 ± 5.11 | 134.37 ± 8.23 | 145.45 ± 8.65 | 138.17 ± 8.38 |
| 30 mins | 127.15 ± 5.59 | 139.65 ± 8.19 | 159.76 ± 8.23* | 131.55 ± 8.23 |
| 60 mins | 128.34 ± 6.98 | 136.31 ± 8.37* | 166.89 ± 8.23* | 120.11 ± 8.17 |
| 90 mins | 119.12 ± 6.67 | 128.67 ± 8.16* | 154.21 ± 7.98* | 120.34 ± 8.36 |
| 120 mins | 101.56 ± 7.66 | 122.79 ± 8.31 | 145.56 ± 8.11* | 117.32 ± 7.56 |
| 240 mins | 106.12 ± 8.32 | 110.73 ± 7.34 | 125.70 ± 8.56 | 114.12 ± 7.13 |

Comparison with control group, *$P < 0.05$ (2) Effects on the thrombo-elasticity chart in patients with coronary heart disease. See Table 9-5.

TABLE 9-5

Effects on different markers before and after treatment

|  |  | Low dosage (n = 30) | Medium dosage (n = 30) | High dosage (n = 30) | Control group (n = 30) |
|---|---|---|---|---|---|
| Before treatment | r | 2.35 ± 1.01 | 2.56 ± 0.980 | 2.54 ± 0.897 0.897 | 2.45 ± 0.985 0.985 |
|  | k | 4.56 ± 1.31 | 4.34 ± 1.23 | 4.17 ± 1.45 | 4.17 ± 1.21 |
|  | ma | 76.3 ± 19.8 | 77.5 ± 17.3 | 46.5 ± 18.1 | 75.7 ± 19.3 |
|  | m∈ | 321.9 ± 24.7 | 344.4 ± 20.9 | 325.5 ± 21.8 | 311.5 ± 23.9 |
| After treatment | r | 3.56 ± 1.78 | 5.98 ± 1.71* | 7.32 ± 1.67* | 4.78 ± 1.43 |
|  | k | 4.88 ± 1.67 | 6.82 ± 1.88* | 8.89 ± 1.34* | 5.67 ± 1.46 |
|  | ma | 75.3 ± 16.7 | 67.3 ± 19.2* | 60.4 ± 18.4* | 74.5 ± 20.3 |
|  | m∈ | 304.8 ± 19.35 | 205.8 ± 21.4* | 154.2 ± 22.5* | 292.2 ± 25.5 |

Comparison with control group, *$P < 0.05$, normal value: r = 4.35 ± 1.089; k = 5.030 ± 1.528; ma = 57.46 ± 20.33; m∈ = 135.09 ± 25.519

Conclusion

The above experimental results show that DSP can make an improvement in bulbar conjunctiva micro-circulation and thrombo-elasticity in patients with coronary heart disease and angina.

10. Effects on Immunity of Red Blood Cells

Effects on Immunity in Red Blood Cells

This experiment uses the blood coagulation method of yeasts sensitized by complement, $C_{3b}$-causing yeast aggregation testing and Enzyme-linked Immunosorbent Assay (ELISA), to test the effects of DSP on the immunosorbent ability of red blood cells, CIC, and SIL-2R in patients with coronary heart disease.

1. Subject. 20 patients with coronary heart disease who qualify under the WHO Coronary Heart Disease Standard are selected.

2. Method.

(1) Testing of immunity of red blood cells. Blood is collected from veins. Coagulation is prevented with Heparin. Blood is washed with normal saline 3 times and made up to a 1×10⁸/ml red blood cell suspension. The immunosorbent ability of red blood cells is tested using the blood coagulation method of yeasts sensitized by complement.

(2) Testing of CIC. The blood serum was collected from patients, and $C_{3b}SYCA$ method was used to dilute samples to the following: 1:8, 1:16, 1:32, 1:64, by.

(3) Testing of solubility of IL-2R. Blood serum was collected from patients using ELISA.

Results (1) Effects on immunosorbent ability when the degree of blood clotting is 1:32. After treatment, immunosorbent ability increases to more than that before treatment (P<0.01). This shows that DSP can increase the immunosorbent ability of red blood cells in coronary heart disease, as shown in Table 10-1.

TABLE 10-1

Effects on immunosorbent ability in patients with coronary heart disease

| Group | Sample number | 1:4 (%) | 1:8 (%) | 1:16 (%) | 1:32^Δ (%) | 1:64^Δ (%) | 1:128 (%) |
|---|---|---|---|---|---|---|---|
| With treatment | 20 | 20 (100) | 20 (100) | 20 (100) | 19 (95) | 16 (90) | 8 (40) |
| Control group | 20 | 20 (100) | 20 (100) | 19 (95) | 12 (60) | 5 (25) | 0 (0) |

Notes:
^Δ p < 0.01

(2) Effects on blood serum CIC, whent the degree of blood clotting is 1:32, after treatment. Its CIC positive percentage is lower than that before treatment (P<0.01). This shows DSP can remove CIC inside the body, as shown in Table 10-2.

TABLE 10-2

Effects on circulating immunocomplex in patients with coronary heart disease

| Group | Sample number | 1:8 (%) | 1:16 (%) | 1:32^Δ (%) | 1:64^Δ (%) |
|---|---|---|---|---|---|
| With treatment | 20 | 17 (85) | 15 (75) | 8 (40) | 3 (15) |
| Control | 20 | 20 (100) | 17 (85) | 15 (75) | 12 (60) |

Notes:
^Δ p < 0.01

(3) Effects on SIL-2R in patients with coronary heart disease. The SIL-2R content is lower than that before treatment (P<0.01). This shows that DSP can lower SIL-2R level, as shown in Table 10-3.

TABLE 10-3

Effects on SIL-2Rin patients with coronary heart disease

| Group | Sample number | Content in sample |
|---|---|---|
| With treatment | 20 | 76.38 ± 72.08 |
| Control group | 20 | 150.69 ± 86.58 |

Notes:
P < 0.01

Conclusion

The above experiment shows that DSP can lower SIL-2R level, strengthen the immune system and the immunosorbent ability of red blood cells.

11. Adjustment of Vegetative Nerve

Adjustment of Vegetative Nerve in patients with Qizhi Xueyu-type coronary heart disease with angina.

This test uses "Wenger-Chongzhongchongxiong" vegetative nerve balance factor analysis to test the heart rate variation (HRV), that is, the fluctuation in the average heartbeat over, a certain period of time or over a long time period in the R-R period. Data, including effects on the sympathetic and para-sympathetic nerves can be calculated, to reflect the regulatory function of the vegetative nervous system.

1. Sample selection: Patients must have had Qizhi Xueyu-type coronary heart disease with angina. Patients were divided into two groups at random. Treatment group: DSP was given, 10 tablets/medication, 3 times/day. Control group: Isordil was given, 10 mg per dosage, 3 times/day. Each medication lasted for 1 month.

2. Standard. (1) The Vascular Nerve Balance Index was recorded before and after treatment as (y): using the "Wenger-Chongzhongchongxiong", vegetative nerve balance factor analysis. y=0±0.56 is normal. When y>+0.56 is abnormal, it shows that the function of the sympathetic nerve increases. When y<−0.56 is abnormal, it shows that the function of the para-sympathetic-nerve increases.

(2) Change in heartbeat before and after treatment (HRV). 24 hrs continuous testing is done to check the ECG change. The standard deviation (SDNN) in the R-R period in 24 hrs is found. SDNN is used to represent the change in heartbeat.

Results

After DSP treatment, the percentage of y>+0.56 dropped significantly (P<0.05), but the drop in the Isordil group before and after treatment was not significant, y>+0.56 (P>0.05). See Table 11-1. After DSP treatment, SDNN in R-R increased significantly (P<0.01), and there was no significant difference in the Isordil group before and after treatment (P>0.05). See Table 11-2. A decrease in HRV means the sympathetic nerve is excited. It is directly proportional to the symptoms in coronary heart disease and the possibility of sudden death and irregularity of heartbeat. DSP can control over-excitement of the para-sympathetic nerve and regulate the balance in the vegetative nerve.

TABLE 11-1

Change in vegetative nerve balance index before and after treatment (y)

| Group | Sample number | y >+ 0.56 Before treatment | y >+ 0.56 After treatment | y <− 0.56 Before treatment | y <− 0.56 After treatment |
|---|---|---|---|---|---|
| With treatment | 30 | 13 (43.33) | 7 (23.33) | 3 (10.00) | 2 (6.67) |
| Control group | 23 | 10 (43.48) | 9 (39.13) | 3 (13.04) | 1 (4.35) |

TABLE 11-2

Change in HRV before and after treatment

| Group | Sample number | SDNN(ms) Before treatment | SDNN(ms) After treatment | P value |
|---|---|---|---|---|
| With treatment | 30 | 4.20 ± 0.19 | 4.41 ± 0.29 | <0.01 |
| Control | 23 | 4.18 ± 0.20 | 4.23 ± 0.21 | >0.05 |

12. DSP Treatment for Liver Disease (1) Research on the Prevention of Chronic Liver Fibrosis 1. Clinical Materials.

1.1 Normal materials. According to the China Viral Hepatitis Association Classification Standards of 1990, 45 patients were confirmed to be infected with chronic active hepatitis, 20 patients with early-stage liver fibrosis. 55 were male and 10 were female.

1.2 Treatment method. Chronic active hepatitis group: Qianglining+DSP (group A), Qianglining (group B), Qianglining injection solution (made by the Jiangsu Tianqing pharmaceutical company) 80-100 ml/day for 6 weeks. 30 tablets of DSP were taken each day, for 3 months and 45 tablets of DSP were given to the early-stage liver fibrosis group each day for 3 months.

Results (1) Improvement of clinical symptoms of chronic active hepatitis B by Qianglining+DSP treatment (See Table 12-1.).

TABLE 12-1

Comparison of the improvement in symptoms by combined treatment and single Qianglining

| | Low Energy | | Indigestion | | Swollen abdomen | | Liver discomfort | |
|---|---|---|---|---|---|---|---|---|
| | Group A | Group B | Group A | Group B | Group A | Group B | Group A | Group B |
| Difference before treatment | 45 | 45 | 43 | 44 | 38 | 36 | 32 | 30 |
| Recovery after treatment (%) | 41 (91.1) | 34 (75.6) | 39 (90.7) | 37 (84.1) | 36 (94.7) | 27 (75.0) | 29 (90.6) | 25 (83.3) |
| P value | <0.05 | | >0.05 | | <0.05 | | >0.05 | |
| Mean recovery day (Mean ± SD) | 13.6 ± 2.4 | 19.1 ± 2.9 | 15.8 ± 2.6 | 17.8 ± 2.5 | 10.8 ± 1.9 | 17.4 ± 2.8 | 15.2 ± 2.3 | 16.8 ± 2.5 |
| P value | <0.05 | | >0.05 | | <0.05 | | >0.05 | |

As shown in Table 12-1: Qianglining+DSP can improve low energy situations, swollen abdomen, and other symptoms, which is different from the recovery percentage and recovery time in the control group (P<0.05).

(2) Chronic active hepatitis B recovery After Qianglining+DSP treatment (See Table 12-2.).

TABLE 12-2

Recovery of physical signs of two groups after treatment

| | Size of liver | | Size of spleen | | Yellowing of eyes | |
|---|---|---|---|---|---|---|
| | Group A | Group B | Group A | Group B | Group A | Group B |
| Abnormal number before treatment | 23 | 20 | 15 | 16 | 19 | 18 |
| Efficient number after treatment (%) | 25 (88.5) | 9 (45.0) | 7 (46.7) | 1 (6.3) | 18 (94.5) | 15 (83.3) |
| P value | >0.05 | | <0.05 | | >0.05 | |
| Mean recovery days (mean ± SD) | 33.6 ± 3.8 | 36.5 ± 4.9 | 58.9 ± 9.6 | 65 | 18.4 ± 3.3 | 29.6 ± 5.1 |
| P value | >0.05 | | >0.05 | | <0.05 | |

As shown in Table 12-2, the sizes of livers and spleens decreased and softened after compound treatment. There was an obvious difference in the percentage of patients with smaller spleens and in the recovery time compared with the control group (P<0.05). Decoloration was also obvious.

(3) Liver functions recovery in chronic active hepatitis B (See Table 12-3.).

TABLE 12-3

Liver functions recovery in the two groups before and after treatment

| | ALT | | AST | | A/G | | DBIL | |
|---|---|---|---|---|---|---|---|---|
| | Group A | Group B | Group A | Group B | Group A | Group B | Group A | Group B |
| Abnormal number before treatment | 45 | 45 | 44 | 45 | 25 | 21 | 32 | 29 |
| recovery number after treatment (%) | 43 (95.6) | 37 (82.2) | 41 (93.2) | 36 (80.0) | 18 (72.0) | 14 (66.7) | 30 (93.8) | 24 (82.8) |
| P value | <0.05 | | <0.05 | | >0.05 | | <0.05 | |
| Mean recovery number (mean ± SD) | 19.1 ± 3.4 | 28.4 ± 3.1 | 22.6 ± 4.0 | 37.8 ± 3.9 | 35.9 ± 7.2 | 39.1 ± 7.4 | 26.5 ± 3.2 | 34.7 ± 3.7 |
| P value | <0.05 | | <0.05 | | >0.05 | | <0.05 | |

As shown in Table 12-3, Qianglining+DSP can lower ALT and the serum bilirubin level and shorten the mean recovery time (P<0.05) but the change in protein ratio is not significant.

(4) Effects on liver fibrosis in chronic active hepatitis B (See Table 12-4.).

TABLE 12-4

Change in liver fibrosis indexes in the two groups after treatment

| | Glycocholic acid | | Hyaluronic acid | | Procollagen peptide III | | Laminin | |
|---|---|---|---|---|---|---|---|---|
| | Group A | Group B | Group A | Group B | Group A | Group B | Group A | Group B |
| Mean before treatment (mean ± SD) | 46.5 ± 6.2 | 48.9 ± 6.7 | 246.2 ± 20.5 | 251.8 ± 11.4 | 188.6 ± 9.7 | 169.9 ± 9.5 | 385.7 ± 21.1 | 391.6 ± 24.5 |
| Mean after treatment (mean ± SD) | 20.1 ± 3.1 | 42.6 ± 5.4 | 138.9 ± 11.4 | 218.4 ± 10.8 | 89.7 ± 7.1 | 152.4 ± 9.2 | 142.3 ± 10.6 | 298.2 ± 16.9 |
| P value | <0.01 | | <0.05 | | <0.05 | | <0.01 | |

As shown in Table 12-4, liver fibrosis standards drop significantly after therapeutic alliance (P<0.05).

(5) Change in early stage liver fibrosis markers (See Table 12-5.).

TABLE 12-5

Change in early stage liver fibrosis markers

| | Glycocholic acid | Hyaluronic acid | III Procollagen peptide | Laminin |
|---|---|---|---|---|
| Mean before treatment (mean ± SD) | 62.8 ± 7.4 | 389.6 ± 21.4 | 294.8 ± 18.9 | 517.7 ± 24.8 |
| Mean after treatment (mean ± SD) | 37.1 ± 62 | 287.5 ± 16.1 | 135.6 ± 9.8 | 282.5 ± 10.2 |
| P value | <0.05 | >0.05 | <0.05 | <0.05 |

As shown in Table 12-5, DSP can lower levels of liver fibrosis markers so that the levels of Glycocholic acid, Procollagen peptide III and Laminin are much lower than those before treatment (P<0.05).

(2) 47 Cases of DSP Treatment of Active Liver Fibrosis

1. Clinical data. There were 93 cases of active liver fibrosis caused by viral hepatitis from March 1996 to March 1998. They were divided into two groups, at random: 47 patients in the DSP group and 46 patients in the control group.

2. Treatment Method. The two groups were given traditional liver treatments: medical glucose, carnine, conbined energy agent, vitamin K1, vitamin C, B and human blood products, etc. DSP was given to the DSP group, 10 tablets/medication, 3 times/day.

4. Observation: Hyulronic Acid (HA), III Procollagen peptide (PIIIP), III Procollagen IV (IV-C), Laminin (LN), γ-spherical protein, and aminotransferase (ALT).

TABLE 12-6

| | Obervable changes | | | | | | | | |
|---|---|---|---|---|---|---|---|---|---|
| | PIIIP deviation | | | IV-C deviation | | | HA deviation | | |
| | B/F treatment | A/F treatment | % | B/F treatment | A/F treatment | % | B/F treatment | A/F treatment | % |
| DSP group | 36 | 111* | 75 | 38 | 13* | 65.8 | 36 | 9** | 75 |
| Ctrl. Group | 34 | 26 | 29 | 37 | 29 | 21.6 | 35 | 29 | 17.1 |

TABLE 12-6-continued

| | Obervable changes | | | | | | | |
|---|---|---|---|---|---|---|---|---|
| | PIIIP deviation | | | IV-C deviation | | | HA deviation | |
| | LN deviation | | | ALT deviation | | | γ-spherical protein deviation | |
| DSP group | 41 | 12* | 70.7 | 47 | 2^Δ | 95.7 | 47 | 17^ΔΔ 63.8 |
| Ctrl. group | 39 | 26 | 33.3 | 45 | 7 | 84.8 | 45 | 38 15.6 |

Notes:
*P < 0.05,
*P < 0.01,
P > 0.05,
ΔP < 0.025.

Conclusion

DSP can control clinical liver fibrosis efficiently.

(3) Treatment of Hepatocirrhosis at the Stage of Losing Compensation.

1. Method. 28 patients with hepatocirrhosis at the stage of losing compensation, 14 patients were in the Observation group, and they were given DSP in addition to the ordinary liver protections and diuretic medications, 15 tablets/each medication, 3 times/day, for 2 weeks. 14 patients were in the Control group, and the treatment was the same as the Observation group, without DSP.

Results

See Table 12-7.

TABLE 12-7

Treatment of hepatocirrhosis at the stage of losing compensation

| Group | Sample number | Obvious Efficacy (%) | Efficacy (%) | Failure (%) | Total Efficacy (%) |
|---|---|---|---|---|---|
| Observation group | 14 | 7 (50.00) | 6 (44.29) | 1 (7.14) | 13 (94.29) |
| Control group | 14 | 3 (21.43) | 5 (35.72) | 6 (44.29) | 8 (57.15) |

Notes:
Statistically calculated, P < 0.05, there is a significant difference.

Conclusion

There is significant improvement in the treatment of hepatocirrhosis at the stage of losing compensation when DSP is added as a medication. DSP does not have side effects and is helpful—hepatocirrhosis at the stage of losing compensation for treating hepatocirrhosis at the stage of losing compensation.

13. The Effectiveness of DSP Therapy in Diabetes and Related Complications (I) DSP Therapy Improves Diabetic Disease in the Elderly 40 diabetic patients were included in the clinical trial. Their diagnoses met with the diabetic diagnosis standard setup by WHO in 1985. 21 of the patients were male, aged 70.2±8.4; 19 of them were female, aged 66.8±5.6. All had suffered from diabetes for 3-25 years with an average of 16.8±6.4. 25 patients also suffered from cardiovascular disease, 18 had cerebrovascular disease, 8 had nephrosis, 12 had neuropathy, 15 had eye disease, and 6 had other complications.

Patients took DSP orally, twice per day, 10 tablets each time for 3 months. During the trial, their physical conditions were monitored by colligation monitoring meter for nail wall microcirculation, produced by Shanghai Laser Research Center.

The trial result reveal that after 3 months of taking DSP, the 40 patients' nail wall microcirculation test indexes had varying degrees of improvement. Their collective cumulative values decreased. Among the patients, those originally with serious abnormalities now had medium abnormality; those originally with medium abnormality had slight abnormalities. The differences before and after treatment were obvious. The differences are listed in the Tables 13-1 and 13-2:

TABLE 13-1

Changes in nail bed microcirculation before and after treatment (x ± s)

| | Before Treatment | After Treatment |
|---|---|---|
| Tube ansiform number (strip/mm) | 3.8 ± 1.2 | 5.2 ± 2.8* |
| Input tube branch ID (μm) | 7.2 ± 2.4 | 8.0 ± 1.6* |
| Output tube branch ID (μm) | 8.9 ± 3.2 | 10.1 ± 2.7** |
| loop top ID (μm) | 10.8 ± 3.6 | 12.0 ± 3.3 |
| Tube ansiform length (μm) | 389 ± 127 | 360 ± 89* |
| Crossing number of tube ansiform (%) | 52.7 ± 19.5 | 42.8 ± 18.2*** |
| Abnormality number of tube ansiform (%) | 22.4 ± 8.3 | 19.2 ± 7.5** |
| Blood vessel motility (movement tnumber per min) | 3.0 ± 1.5 | 2.6 ± 1.0* |
| Number of WBC (No./15 second) | 16.4 ± 8.6 | 14.0 ± 7.4* |

Compared with the Index Before Treatment: *P < 0.05 P < 0.01 *P < 0.001

TABLE 13-1

Nail nail bed microcirculation colligation scores before and after treatment (x ± s)

| | Before Treatment | After Treatment |
|---|---|---|
| Tube ansiform number (strip/mm) | 3.8 ± 1.2 | 5.2 ± 2.8* |
| Input tube branch ID (μm) | 7.2 ± 2.4 | 8.0 ± 1.6* |
| Output tube branch ID (μm) | 8.9 ± 3.2 | 10.1 ± 2.7** |
| loop top ID (μm) | 10.8 ± 3.6 | 12.0 ± 3.3 |
| Tube ansiform length (μm) | 389 ± 127 | 360 ± 89* |
| Crossing number of tube ansiform (%) | 52.7 ± 19.5 | 42.8 ± 18.2*** |
| Abnormality number of tube ansiform (%) | 22.4 ± 8.3 | 19.2 ± 7.5** |
| Blood vessel motility (movement tnumber per min) | 3.0 ± 1.5 | 2.6 ± 1.0* |
| Number of WBC (No./15 second) | 16.4 ± 8.6 | 14.0 ± 7.4* |

Compared with the Index Before Treatment:
*P < 0.05
**P < 0.01
***P < 0.001

(II) DSP Heals Diabetic Neuritis

1. Clinical Information. There were a total 36 patients, 9 of them were male, 27 of them were female. The eldest was 82 years old; the youngest was 45 years old. The patient with the longest history of suffering from the disease had it for 4 years prior to the study. The patients were selected according to the diagnosis standard on page nine of Diabetic Neuropathy of Practical Internal Medicine.

2. Treatment Method. Controlling blood glucose level in normal circumstances. 10 tablets of DSP were taken orally after meals, three times per day. When the disease showed observable improvement, patients reduced their intake of DSP to 3 tablets, 3 times per day. Each medication lasted 40 days.

3. Treatment Results. 31 patients had great improvement (clinical symptoms disappeared); 5 cases had observable improvement; none of the cases had no improvement.

Conclusion

DSP has positive healing effects on diabetic end-brush neuritis

14. The Effectiveness of DSP Therapy on Optical Fundus Vascular Diseases

Healing of Retinal Vein Occlusion by Dan Shen Pill

1. Disease Conditions. Among the 42 patients, 27 had the disease in one eye, 15 had it in both eyes. 18 had central retinal vein occlussion (CRVO), 24 had branch retinal vein occlussion (BRVO).

2. Treatment Method. (1) Patients orally ingested large amounts of DSP, i.e. 15 grains each time, 3 times per day. (2) Patients orally ingested a DSP took injections of urokinase in the conjunctiva, and orally ingested a suitable dose of hormone. When patients improved and stablized, they were further treated by laser.

3. Treatment Results: (1) Obviously improved: Patients could see objects within 5 feet or eyesight becames 1.0 or higher; (2) Improved: Eyesight improved by 2-4 lines; (3) No change: Eyesight improved or worsened by 1 line; (4) Worsens: Eyesight worsened by more than 2 lines. Obviously improved and Improved can be considered as effective.

Results

See Table 15-1.

TABLE 15-1

Comparison of Eyesight Before and After Treatment (Unit %)

| | <0.1 | | 0.1–0.5 | | 0.6–1.0 | | 1.0 | |
|---|---|---|---|---|---|---|---|---|
| | Before | After | Before | After | Before | After | Before | After |
| BRVO | 3 (18) | 1 (4) | 11 (48) | 6 (27) | 8 (35) | 10 (43) | 1 (4) | 6 (26) |
| CRVO | 10 (58) | 9 (47) | 8 (42) | 8 (42) | 1 (5) | 2 (11) | 0 (0) | 0 (0) |

The cause of retinal vein occlusion is still not very clear. Hypertention, hyperlipidemia, and arteriosclerosis are usually considered as likely causes of retinal vein occlusion. Doctor of traditional Chinese medicine believes that it is caused by stagnant blood flow. DSP can activate blood circulation and relieve congestion, improve microcirculation, relieve hydropsy, and encourage blood absorption. In so doing, it can improve eyesight. DSP can also be used to heal different kinds of optical fundus vascular diseases that are generally termed as Xueyuzheng, such as central retinal artery occlusion, hypertensive retinal arteriosclerosis, diatetic retinal lesion, central plasm optic neuropathy, central permeation optic neuropathy, ischemic optic neuropathy, optic neuritis, atrophy of the optic nerve, etc.

15. DSP's Effect on Hemorheology

The effect of DSP on hemorheology of cervical syndrome patients Patients were selected based on the diagnosis standard set up during The National Cervical Syndrome Panel Discussion in May 1984. 80 patients were randomly divided into two groups: (1) 50 patients took DSP and Qiankun guzhizengsheng Wan (Observation);

(2) 30 patients took only Qiankun guzhizengsheng Wan (Control). The Observation group took 10 grains of DSP 3 times a day and 1 grain of Qiankun guzhizengsheng Wan twice a day. The Control group took only 1 grain of Qiankun guzhizengsheng Wan twice a day. The medication for both groups lasted 2 months.

Result (1) In the Observation group, besides fibrinogen, whole blood viscosity, whole blood reduction viscosity, plasma viscosity, hematocrit and Aggregation Index of RBC all decreased. The differences before and after treatment were obvious (P<0.05 or P<0.01). Compared with the Control group, whole blood viscosity, whole blood reduction viscosity, plasma viscosity, Aggregation Index of RBC had obvious decreases (P<0.05 or P<0.01). After treatment, the Control group shared an obvious change only in the hemagglutilation index (P<0.05 or P<0.01). The results are listed in Table 16-1.

TABLE 16-1

Changes of hemorheology in the two groups after treatment (x ± s)

| Group | Treatment | Whole Blood Viscosity (mPa · s) | Whole blood reduction viscosity (mPa · s) | Plasma Viscosity (mPa · s) |
|---|---|---|---|---|
| Observation Group (50 cases) | Before | 5.66 ± 1.12 | 8.72 ± 1.46 | 2.16 ± 0.82 |
| | After | 4.98 ± 0.84$^{\Delta\Delta*}$ | 8.01 ± 1.25$^{\Delta*}$ | 1.62 ± 0.36$^{\Delta**}$ |
| Control group (30 cases) | Before | 5.42 ± 1.35 | 8.72 ± 1.52 | 2.24 ± 1.02 |
| | After | 5.48 ± 1.08 | 8.74 ± 1.43 | 2.20 ± 0.48 |

TABLE 16-1-continued

Changes of hemorheology in the two groups after treatment (x ± s)

| Group | Treatment | Fibrinogen (g/L) | hematocrit (V) | Hemagglutilation index |
|---|---|---|---|---|
| Observation Group (50 cases) | Before | 3.94 ± 0.84 | 48.12 ± 3.84 | 1.08 ± 0.14 |
| | After | 3.90 ± 0.81 | 44.70 ± 4.67$^{\Delta\Delta}$ | 0.86 ± 0.12$^{\Delta\Delta**}$ |
| Control group (30 cases) | Before | 3.98 ± 0.90 | 48.16 ± 4.85 | 1.06 ± 0.10 |
| | After | 4.02 ± 0.87 | 45.53 ± 5.78 | 0.98 ± 0.14$^{\Delta}$ |

Note: Compared with results of pretreatment, $^{\Delta}$P < 0.05, $^{\Delta\Delta}$P < 0.01; Compared with results of post treatment, *P < 0.05, **P < 0.01

16. DSP's Healing Effect on Chronic Pulmonary Heart Disease

1. Using DSP to Cure Chronic Pulmonary Heart Disease 90 cases of chronic pulmonary heart disease were selected based on the diagnosis standard set up during the National Pulmonary Heart Disease Congress in 1977. The patients were divided randomly into an Observation group and a Control group. The 60 cases in the Observation group took DSP, while the 30 cases in the Control group took persantin. Based on the objectives of: reduced inflammation, coughing cessation, dissolving of sputum, cardial and diuretic action, and cardiac function improvement, the Observation group was given 10 grains of DSP, 3 times a day. The Control group was given 50 mg of Poon Seng Ding each time, 3 times a day. Treatment lasted 1 month.

1. Treatment Standard (1) Obvious Efficacy. The symptoms such as coughing, asthma, pulmonary rales, syanosis were relieved or disappeared. The ascites and lower limbs sdema were disappeared as well. Heartbeat was under 100 times/min and cardiac function was improved above grade I-II. The urine volume per day increased by 600 ml and above, while the body weight decreased by 4%. The end-brush circulations were improved.

(2) Efficacy. Above all markers were partly improved.

(3) Inefficacy. Above all markers were not improved.

2. Results. Total efficacy rate of treatment group is 95% and that of control group 76%, the difference of which is statistically significant (P<0.05=. The result revealed that the efficacy of DSP is superior to persantin, showed as table 17-1, and that hemorheology in DSP group has more improvement than that in persantin group, showed as table 17-2.

TABLE 17-1 comparison of efficacy rates before treatment and after treatment

| Group | Case number | Obvious efficacy | Efficacy | inefficacy | Total efficacy rate |
|---|---|---|---|---|---|
| Treatmeat group | 60 | 35 (0.583) | 22 (0.367) | 3 (0.05) | 57 (0.95) |
| Control group | 30 | 14 (0.47) | 9 (0.3) | 7 (0.23) | 23 (0.76) |

TABLE 17-2

Comparison of hemorheologic markers before treatment and after treatment

| Group | Treatment group Before treatment | Treatment group After treatment | P value | Control group Before treatment | Control group After treatment | P value |
|---|---|---|---|---|---|---|
| Blood viscosity | 4.55 ± 0.84 | 3.54 ± 0.63 | <0.01 | 4.35 ± 0.81 | 3.66 ± 0.58 | <0.05 |
| Hematocrit (VOL/%) | 0.53 ± 0.05 | 0.33 ± 0.22 | <0.01 | 0.48 ± 0.05 | 0.37 ± 0.05 | <0.05 |
| Fibrinogen (g/L) | 4.33 ± 0.35 | 1.073 ± 0.145 | <0.01 | 4.22 ± 0.34 | 3.60 ± 0.23 | <0.05 |
| Aggregation rate of platelet (%) | 39.27 ± 2.137 | 21.66 ± 19.30 | <0.01 | 4.16 ± 2.32 | 32.28 ± 20.30 | <0.05 |

(2) Treatment of Acute Pulmonary Heart Diseases 70 patients with acute pulmonary heart disease were chosen according to 2nd Whole Nation Pulmonary Heart Disease Conference Standards, 1977. Both the Treatment and Control were given treatment designed to reduce inflammation, cease coughing, dissolve sputum, and act as cardial and diuretics. They were also given slow-flowing oxygen. DSP was given on an ordinary treatment basis, 10-15 tablets each, 3 times/ day for 2 weeks. 36 patients were in the control group. All treatments for the control group were the same as that of the treatment group, except DSP.

1. Treatment Standard (1) Obvious Efficacy. Pulmonary and cardiac function improved to grade II, the symptoms such as coughing, expectoration, dyspnoea, and cyanosis in the resting state were reduced or even disappeared. The liver becames smaller, and lung rales disappeared.

(2) Efficacy. Pulmonary and cardiac function improved to grade I, and the elimination of clinical symptoms was releaved (3) Failure. No improvement in or worsening of pulmonary and cardiac function.

2. Results. There was a significant difference in the efficacy of the two groups ($X^2$=4.46 and 4.95, P<0.05). Treatment group results were better than that of the Control group, as shown in Table 17-3. There were obvious changes in blood flow in the Treatment group before and after treatment compared with that of the Control group (P<0.05). The blood viscosity of the control group decreased after treatment, but there was no statistical deviation, as shown in Table 17-4.

Table 17-3 Comparison of Clinical Total Efficacy Before and after Treatment

TABLE 17-3

Comparison of clinical total efficacy before and after treatment

| Group | Sample number | Obvious Efficacy | Efficacy | Failure | Total efficacy |
|---|---|---|---|---|---|
| Treatment group | 36 | 17 (0.427) | 15 (0.417) | 4 (0.111) | 32 (0.889) |

TABLE 17-3-continued

Comparison of clinical total efficacy before and after treatment

| Group | Sample number | Obvious Efficacy | Efficacy | Failure | Total efficacy |
|---|---|---|---|---|---|
| Control group | 34 | 9 (0.265) | 14 (0.412) | 11 (0.323) | 23 (0.677) |

TABLE 17-4

| | Treatment group | | | Control group | | |
|---|---|---|---|---|---|---|
| Group | Before treatment | After treatment | P value | Before treatment | After treatment | P value |
| ηb1 (mPa · s) | 9.01 ± 1.70 | 6.11 ± 1.13 | <0.01 | 8.98 ± 1.82 | 7.91 ± 1.95 | >0.05 |
| ηbh (mPa · s) | 6.32 ± 1.21 | 5.15 ± 0.75 | <0.01 | 6.30 ± 1.42 | 5.91 ± 1.77 | >0.05 |
| ηp (mPa · s) | 1.95 ± 0.14 | 1.70 ± 0.08 | <0.01 | 1.92 ± 0.12 | 1.80 ± 0.18 | >0.05 |
| EAI | 1.57 ± 0.13 | 1.40 ± 0.08 | <0.05 | 1.60 ± 0.15 | 1.56 ± 0.20 | >0.05 |
| HCT (%) | 46.72 ± 5.41 | 40.69 ± 5.16 | <0.05 | 45.93 ± 5.32 | 43.80 ± 5.92 | >0.05 |
| ET (s) | 23.71 ± 1.77 | 20.82 ± 1.08 | <0.05 | 24.02 ± 1.94 | 23.34 ± 2.06 | >0.05 |
| ESR (mm) | 24.00 ± 11.28 | 16.60 ± 9.30 | <0.05 | 23.89 ± 12.02 | 29.90 ± 13.20 | >0.05 |
| Fb (mg%) | 301.50 ± 32.14 | 270.16 ± 20.12 | <0.05 | 299.60 ± 39.28 | 288.10 ± 40.36 | >0.05 |

(3) Treatment of Pulmonary Heart Diseases Causing Red Blood Cell Proliferation 23 patients were chosen according to 2$^{nd}$ Whole Country Conference on Lung and Heart Diseases Standards, 1977. Besides the typical symptoms, hemoglobin content was >160 g/L in males and >150 g/L in females. Red blood cell pressure was >0.60 in males and >0.55 in females.

10 tablets of DSP were taken 3 times/day. Drugs to fight infections, cease coughing and asthma, diuresis, dilate vessel, and glucocorticoid were given during treatment. After 20-56 days of treatment, (the average was 38 days treatment), there was a significant improvement in conjunctival congestion and lips, tongues, and nail bed with cyanosis. Hemoglobin content and hematocrit also decreased. After treatment (x±s), hemoglobin was −3.10±2.90, P<0.01, hematocrit was −11.80±2.90, P<0.05, show a significant difference. There were side effects during treatment.

17. Treatment of Adrenal Syndrome
Treatment Effects on Nephrotic Syndrome 80 patients with nephrotic syndrome were chosen at Wuhan Hospital from 1998-1999. All the histories, physical signs, supportive checking, and courses were recorded according to 3$^{rd}$ Whole Country Kidneys Diseases Association Conference Standards, 1992. Patients with nephrotic syndromes caused by other factors were eliminated. Patients were divided into 2 groups, at random: Control group: Treated with ordinary delta prenovis treatment and Western medications; Treatment group: DSP, 10-15 tablets, 3 times/day, for 8 weeks; no other cholesterol-lowering, anti-coagulation, anti-thrombosis, and vessel-dilation drugs with the ordinary delta prenovis treatment basis.

1. Treatment Standards. Classified according to the 2$^{nd}$ Whole Country Chinese Medicine Kidney Disease Conference Standard.

(1) Complete remission: Symptoms and physical signs disappeared. Urine protein content was <0.2 g/24 h. Renal function and blood lipoprotein content become normal. Urine red blood cell content is exceed 0-3/HP (2) Basic remission: Symptoms and physical signs disappeared. Urine protein content was <1 g/24 h. There was little Urine red blood cells~(+)

(3) Partial remission: Symptoms and physical signs improved. Experimental examination standards improved but did not reach basic retrieval standards.

(4) Failure: Symptoms and physical sign and experimental examination results did not change after 2 months on treatment.

Results (1) Table 18-1 shows that the complete reversal percentage and total efficacy in the treatment group were 55% and 90%, respectively, which was significantly higher than those in the control group: 27.5% and 65% (P<0.05). DSP, combined with other medications, can improve treatment results and reduce the percentage of reoccurrence.

TABLE 18-1

Clinical treatment result comparison in 2 groups

| | Cases | Complete Retrieval | Basic Retrieval | Partial Retrieval | Failure | Reoccur | Total efficacy |
|---|---|---|---|---|---|---|---|
| Treatment group | 40 | 22 | 10 | 4 | 4 | 3 | 90% |
| Ctrl. group | 40 | 11 | 9 | 6 | 14 | 8 | 65% |

(2) Table 18-2 shows that there are no significant difference in Urine osmotic pressure, Urine lysozime, and Urine C3 testing before and after treatment in the same group (P>0.05), treatment group and control group after treatment (P>0.05). It also shows that renal corpuscle and tubule damage is difficult to recover from in the short run. Table 18-2 shows no significant abnormality is found in the same group before and after treatment (P<0.01=and in treatment group and control group after treatment (P<0.05).

(3) Table 18-3 shows all different markers before and after treatment P<0.01. The treatment group and control group P<0.05 have significant difference, except hematocrit.

TABLE 18-2

Comparison of parts of biochemical indexes in 2 groups (x ± s)

| | | Urea protein (g/24 h) | Plasma albumin (g/l) | TG (mmol/L) | Cholesterol (mmol/L) | Blood creatinine (μmmol/L) | Blood urea nitrogen (mmol/L) | Blood immuno-albumin (g/l) | Urea osmotic pressure (mOsm/kg · H$_2$O) | Urease (mg/ml) | Urea C3 (mg/l) |
|---|---|---|---|---|---|---|---|---|---|---|---|
| Treatment group | B.T | 7.10 ± 3.67 | 23.30 ± 5.70 | 3.79 ± 1.58 | 10.83 ± 1.23 | 123.7 ± 87.35 | 9.95 ± 3.71 | 5.39 ± 1.70 | 690 ± 205 | 5.42 ± 4.23 | 1.98 ± 2.13 |
| | A.T | 0.78 ± 0.33 | 35.42 ± 0.76 | 1.77 ± 0.74 | 4.99 ± 0.92 | 80.35 ± 24.67 | 5.41 ± 2.13 | 9.00 ± 2.37 | 721 ± 315 | 5.98 ± 4.77 | 1.87 ± 2.27 |
| Control group | B.T | 6.24 ± 2.35 | 24.10 ± 5.30 | 3.32 ± 1.94 | 11.23 ± 1.35 | 127.8 ± 67.37 | 10.73 ± 4.35 | 5.91 ± 2.48 | 603 ± 298 | 6.12 ± 4.15 | 2.16 ± 2.62 |
| | A.T | 1.76 ± 0.54 | 31.47 ± 2.64 | 1.99 ± 0.92 | 6.82 ± 2.05 | 89.74 ± 51.73 | 6.90 ± 2.21 | 7.87 ± 2.19 | 674 ± 213 | 5.98 ± 4.63 | 2.24 ± 2.87 |

Keys:
B.T. = before treatment,
A.T. = after treatment

TABLE 18-3

Comparison of blood flow in 2 groups (x ± s)

| | | Whole blood viscosity (high transect) | Whole blood viscosity (low-transect) | Plasma viscosity | Red blood cell pressure | Aggregation Index of red blood cells |
|---|---|---|---|---|---|---|
| Treatment group (40 cases) | Before treatment | 7.83 ± 1.31 | 11.78 ± 1.96 | 1.96 ± 0.37 | 46.81 ± 3.05 | 2.09 ± 0.11 |
| | After treatment | 4.96 ± 1.24 | 7.91 ± 1.52 | 1.48 ± 0.17 | 42.74 ± 3.23 | 1.41 ± 0.21 |
| Control group (40 cases) | Before treatment | 7.46 ± 1.19 | 11.31 ± 2.04 | 1.89 ± 0.41 | 47.01 ± 2.99 | 2.11 ± 0.19 |
| | After treatment | 5.47 ± 1.35 | 8.27 ± 1.18 | 1.61 ± 0.26 | 44.35 ± 2.72 | 1.62 ± 0.24 |

8. Treatment of Other Diseases
(1) Treatment of Bronchitis in Children
1. Clinical materials. 78 patients were selected and divided at random into Treatment group (42 total, 25 males and 17 females), and control group (36 total, 20 males and 16 females). All patients stayed in the hospital. The youngest one was 2 months old, and the oldest one was 12 years old.
2. Treatment method. Anti-infectants was given to both groups, and DSP was given orally to the Treatment group 3 times a day. Dosage: <1 yr-old, 2 tablets each time; 1~3 yr old, 3 tablets each time; 3~8 yr-old, 5 tablets each time; 8-12 yrs old, 8 tablets each time.
3. Observation tasks. See Table 19-1.

TABLE 19-1

Clinical symptoms and experimental results in the two groups

| Group | n | Fever | Cough-ing | asthma | Lung Rales | WBC ≥ 10.0 × 10$^9$/L | pneumonia showed by chest X-ray |
|---|---|---|---|---|---|---|---|
| Treatment group | 42 | 32 | 42 | 10 | 42 | 25 | 42 |
| Control group | 36 | 22 | 36 | 8 | 36 | 20 | 36 |

4. Treatment standards. (1) Obvious efficacy: The child was free of fever and lung rales after 5 days of treatment. There was absorption of original lesion focus; (2) Efficacy: Fever and lung noise mostly disappeared after 5 days of treatment, and there was a better absorption of original lesion focus after 10 days of treatment; (3) Failure: No improvements in the above symptoms were noted, and there was no improvement in the absorption of the original lesion focus.
Results

TABLE 19-2

Treatment of pneumonia in children

| Group | Obvious Efficacy | Efficacy | Failure | Total efficacy(%) | Average days of treatment |
|---|---|---|---|---|---|
| Treatment group | 18 | 20 | 4 | 90.5 | 10.6 |
| Control group | 12 | 14 | 10 | 72.2* | 13.4** |

Notes: comparison of 2 groups: *P < 0.05, immediate significant difference; **P < 0.05, significant difference DSP combined with antibiotics can improve treatment results in infections. The DSP treatment ended fever and rales better than that of the control group. DSP raised the recovery percentage for pneumonia in children and shortened the duration of treatment without significant side effects.

(2) Effects on hemicrania 58 patients with hemicrania were selected from clinics. They all qualify under International Headache Standards classifications. 10 tablets of DSP (25 mg/tablet) were given to the Treatment group, 3 times/day. 5 mg of Flunarizine was given to the control group, once a day, orally. The medication lasted 8 weeks. Treatment results and side effects were recorded every 2 weeks. No other pain-killing medications were taken within the 6 months.

Treatment standards. Controlled: Headaches disappeared with medication, and there was no reoccurrence after treatment ended; Obvious efficacy: The seriousness of headaches is reduced, duration is shortened, and onset frequency is reduced to 75% or more; Efficacy: The level of headache is reduced, and onset frequency is reduced 50%~70%; Failure: No improvement in headaches.

The result shows that the efficacy in the treatment group is higher than that of the control group (P<0.05=. DSP can efficiently cure and prevent hemicrania. See Table 19-3.

TABLE 19-3

Comparison of DSP and Flunarizine's effects on hemicrania

|  | Controlled | Obvious Efficacy | Efficacy | Failure | Total efficacy |
|---|---|---|---|---|---|
| DSP group (30 cases) | 13 | 9 | 5 | 3 | 90.00% |
| Flunarizine (28 cases) | 5 | 7 | 7 | 9 | 67.86% |

Notes: After $X^2$ statistic testing, P < 0.05

(3) Treatment of Chronic Gastritis 35 cases of chronic gastritis, including 15 cases of superficial gastritis, 6 cases of chronic erosive gastritis, and 14 cases of chronic atrophic gastritis were selected. All had blood congestion, including 3 cases of positive pylora-bacilli positive and 5 cases of co-duodenal bulb inflammation. 10 tablets of DSP were taken 3 times a day.

Treatment standards. (1) Recovery: All symptoms disappeared, appetite improved, focus inflammation disappeared when observed by gastroscope; (2) Efficacy: Symptoms mostly disappeared, focus inflammation showed improvement when observed by gastroscope;

(3) Improvement: Symptoms were reversed, focus inflammation showed improvement when observed by gastroscope;

(4) Failure: No improvement was noted.

Results 12 cases achieved 34.3% recovery; 11 cases achieved 31.4% efficacy; 8 cases achieved 22.9% improvement; 4 cases failed (11%); and the total efficacy was 88.7%.

DSP can regulate the function of blood vessels, restrain platelet aggregation, control thrombosis, clear out stagnant blood in the gastric mucosa and cure stamoachache caused by chronic gastritis. It can efficiently eliminate the dead parts of the erosive gastric mucinitis, activate megakaryocytes, and stimulate production of new cells to improve the recovery from inflammation.

(4) Treatment of Dizziness 61 patients were divided into two groups at random. 29 patients were in the Treatment group, including 22 patients with insufficient blood supply to the cerebral artery, 7 patients with Meniere Disease, 5 patients with high blood pressure, and 2 patients with coronary heart disease. 32 patients were in the control group, including 22 patients with insufficient blood supply to the cerebral artery, 10 patients with Meniere Disease, 7 patients with high blood pressure, and 4 patients with coronary heart disease. 10 tablets of DSP were given to the Treatment group, 3-5 times/day for 3-7 days. 50 mg of lidocaine was injected into the Control group, once a day for 3-7 days.

Treatment method: (1) Obvious Efficacy: Dizziness and other companion symptoms disappeared, and there was no re-occurrence for 12 hrs after observation. (2) Efficacy: The level of dizziness and other symptoms disappeared. (3) Failure: No improvement.

Results

The total efficacy in the Treatment group and the Control group were 86% and 87.5%, respectively. No significant abnormality was found, as shown in Table 19-4. These two groups of drugs can treat fainting efficiently. Therefore, DSP can be a convenient and efficient drug to treat fainting caused by insufficient blood supply to the brain.

TABLE 19-4

Comparison of treating dizziness

|  | Treatment group | | | | | Control group | | | | |
|---|---|---|---|---|---|---|---|---|---|---|
|  | Cases | Obvious Efficacy | Efficacy | Failure | Total efficacy | Cases | Obvious Efficacy | Efficacy | Failure | Total efficacy |
| Insufficient blood supply to the brain | 23 | 14 | 8 | 1 | 22 (96%) | 22 | 12 | 8 | 2 | 20 (91%) |
| Meniere disease | 6 | 0 | 3 | 3 | 3 (50%) | 10 | 6 | 2 | 2 | 8 (80%) |
| Total | 29 | 14 | 11 | 4 | 25 (86%) | 32 | 18 | 10 | 4 | 28 (87.5%) |

Notes: after $X^2$ statistic testing, P > 0.05

(5) Treatment of Damaged Lateral Malleolus Joint

There were 53 males and 34 females in this experiment, ages 14-60. All cases were selected according to external injury and typical clinical symptoms after x-ray photography to eliminate cases of broken bone.

Treatment method: 30 tablets of ground DSP with 30 ml of 75% ethanol were mixed to a solution for external use. It was applied to the injured area 3 times a day with normal medication for 5 days.

Results

After DSP treatment, patients felt symptoms disappear and joint and ligament function recover. There were no obvious pressure pain spots. 42 patients recovered after 1 treatment, 37 patients recovered after 2 treatments, and 8 patients recovered after 3 treatments.

DSP can eliminate swelling and stagnant blood, and can kill pain. Among their active ingredient borneol can increase its absorption through the skin and maintain concentrations of the drugs at the application site, so it can efficiently and quickly treat damage of the lateral malleolus joint. It is helpful in treating broken bones, bone death and proliferation of bone.

(6) Prevention and Treatment of Plateau Hypoxia

Plateau hypoxia can lead to capillary circulation disorder, causing blood perfusing insufficiency. Plateau hypoxia also leads to high blood viscosity, increased red blood cell quantity and red blood cell aggregation, enhanced red blood cell rigidity, increased platelet aggregation, and change in pH value. All the above factors affect blood viscosity and the radius of capillaries. Platelet aggregation can increase resistance in capillaries, leading to blockage. When blood viscosity increases, the radius of capillaries also increases and leads to increased resistance and congestion. There are common properties in the blood flow of people with plateau hypoxia: "concentration" (increased red blood cell pressure), "viscosity" (increased whole blood viscosity), "aggregation" (increased aggregation of red blood cells). All the above are different at different sea levels and durations. Fore mentioned pharmaphysiologic and clinical research show that DSP can lower hematocrit, blood sedimentation and blood viscosity, so it is helpful in preventing and treating plateau hypoxia.

(7) Prevention and Treatment of Senile Dementia

Senile dementia can be classified as Alzheimer's Disease (AD), vascular dementia and combined dementia. After DSP treatment, there is statistically significant improvement in AD and vascular dementia by measurement analysis and Chinese medicine clinical observation ($p<0.05$ or $p<0.01$). DSP is helpful for treating sluggishness, reticence, forgetfulness, fatigue, and ecchymosis at a total efficacy of 40%, and sadness, anger, rashness, and irritation at a total efficacy of 85.7%.

Conclusion

To conclude, DSP can efficiently cure coronary heart disease in very low dosages. It is well packed, easily absorbed, safe and has no side effects. It relieves angina efficiently and reduces onset frequency and level of pain. It can also reduce the volume of glyceryl trinitrate used. Its total efficacy on angina and ECG efficacy are higher than that in Isordil in long-term use. It also improves cardiac function, blood dynamics, ECG, and blood flow in patients with coronary heart disease. In the treatment of unstable angina, DSP improves non-symptomatic insufficient blow flow to cardiac muscles. DSP can improve abnormal blood flow, lower blood viscosity, relieve atherosclerosis, and prevent thrombosis more efficiently than Isordil. It is an ideal drug for preventing and treating coronary heart disease, angina and atherosclerosis. It can end cardiac arrhythmia and prevent the reoccurrence of myocarditis in patients with coronary heart disease, if it is used over a long period of time.

Besides preventing damage from free radicals and atherosclerosis, treating hyperlipidemia and high viscosity syndrome, DSP can also lower blood viscosity and resistance in blood vessels to regulate reverse LVH through capillary circulation.

DSP can treat high blood pressure and efficiently regulate blood pressure. It can also increase the sensitivity of insulin, lower insulin level and improve the interior function of blood vessels, which are important steps in treating high blood pressure.

DSP can strengthen the primary immune system, increase the immunosorbent ability of red blood cells, and improve primary capillary circulation, which is helpful in acute myocardial infarction and cerebral vessel lesion.

DSP can regulate vegetative nerve balance. It can control high excitement in the sympathetic nerves to balance the vascular nerve for the prevention of coronary heart disease.

DSP can efficiently treat hepatitis B, active liver cirrhosis, chronic liver fibrosis and liver cirrhosis at the stage of losing compensation.

DSP can treat diabetes and its companion diseases.

DSP can efficiently treat ocular nerve diseases and can be applied widely to ocular diseases, such as central retinal artery occlusion, hypertensive retinal arteriosclerosis, diatetic retinal lesion, central plasm optic neuropathy, central permeation optic neuropathy, ischemic optic neuropathy, optic neuritis, atrophy of the optic nerve, etc.

DSP can treat dizziness caused by insufficient blood supply to the cerebral artery, Meniere Disease, high blood pressure, and coronary heart disease.

DSP can treat chronic and acute pulmonary heart disease, red blood cell proliferation and bronchitis in children.

DSP can treat renal syndrome and its companion diseases.

DSP can treat hemicrania, chronic gastritis, fracture and femofal head necrosis, ligament damage, broken bones, bone matrix hyperplasia, plateau hypoxia and Alzheimer's Disease.

The following methods can further explain this invention in different aspects. They are only used to explain this invention and do not put on any restrictions on it.

Example 1

| 1. Prescription dosage | |
|---|---|
| Radix Salviae Miltiorrhizae | 41.06 g |
| Radix Notoginseng | 8.03 g |
| borneol | 0.46 g |
| polyethylene glycol 6000 | 18 g |
| Makes 1000 pills | |

2. Extraction of Radix Salviae Miltiorrhizae and Radix Notoginseng

Radix Salviae Miltiorrhizae and Radix Notoginseng are put into extraction tank, added 5 times water as volume as above raw materials, decocted for 2 hours, filtered, and the first filtrate is got. The residue is added 4 times water as volume as above raw materials, decocted for 1 hour, filtered, and then the filtrate is mixed with the first filtrate. The mixed filtrate is concentrated under decompressed conditions until the solution volume (L) to raw materials weight (Kg) ratio is 0.9-1.1. 95% ethanol is gradually poured in until the concentration of ethanol is 69-71%, settled for 12 hours, and filtered. The filtrate, in which ethanol is evaporated, is concentrated to extract of the relative of 1.32-1.40.

3. Preparation of Product

The above extract is mixed with borneol and polyethylene glycol 6000. The mixture is heated to 85-90° C., melted for 20-120 mins, and then transferred to a dropping machine at 85-90° C. The melted mixture are dropped into the liquid paraffin of which the temperature is at 7-8° C. The dropping pellets are taken out and the oil is removed.

4. Characteristics of the Products

The product is a reddish brown-brownish black sphere with an even size, smooth color, scent, and bitter taste. The weight is 25 mg 115%/pill, and the diameter is 3.34±15% mm.

Example 2

| 1. Prescription dosage | |
|---|---|
| Radix Salviae Miltiorrhizae | 31.12 g |
| Radix Notoginseng | 9.21 g |

133

-continued

| 1. Prescription dosage | |
|---|---|
| borneol | 0.50 g |
| polyethylene glycol 6000 | 20 g |
| Makes 1000 pills | |

2. The extraction of red sage root and notoginseng, preparation and characteristics of the product are the same as Example 1.

Example 3

| 1. Prescription dosage | |
|---|---|
| Radix Salviae Miltiorrhizae | 59.36 g |
| Radix Notoginseng | 6.38 g |
| borneol | 0.34 g |

134

-continued

| 1. Prescription dosage | |
|---|---|
| polyethylene glycol 6000 | 21 g |
| Makes 1000 pills | |

2. The extraction of red sage root and notoginseng, preparation and characteristics of the product are the same as Example 1.

What is claimed is:

1. A pharmaceutical capsule for oral administration comprising an extract of a mixture consisting only of Radix Salviae miltiorrhizae and Panax notoginseng, wherein the weight ratio of Radix Salviae miltiorrhizae to Panax notoginseng in the mixture ranges from 3.2:1 to 10:1, wherein the extract comprises (1) Danshensu and/or a pharmaceutically acceptable salt thereof, (2) salvianolic acid B, and (3) protocatechuic aldehyde, and wherein the pharmaceutical capsule for oral administration further comprises borneol.

* * * * *